United States Patent
Kortagere et al.

(10) Patent No.: US 9,616,065 B2
(45) Date of Patent: Apr. 11, 2017

(54) COMPOSITIONS USEFUL IN TREATING BRAIN-RELATED DISEASES OR DISORDERS AND METHODS USING SAME

(71) Applicant: DREXEL UNIVERSITY, Philadelphia, PA (US)

(72) Inventors: Sandhya Kortagere, Newtown, PA (US); Ole Valente Mortensen, Narberth, PA (US); Andreia C. K. Mortensen, Narberth, PA (US); Joseph M. Salvino, Chester Springs, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 14/784,536

(22) PCT Filed: Apr. 16, 2014

(86) PCT No.: PCT/US2014/034354
§ 371 (c)(1),
(2) Date: Oct. 14, 2015

(87) PCT Pub. No.: WO2014/172453
PCT Pub. Date: Oct. 23, 2014

(65) Prior Publication Data
US 2016/0074408 A1 Mar. 17, 2016

Related U.S. Application Data

(60) Provisional application No. 61/812,401, filed on Apr. 16, 2013.

(51) Int. Cl.
| | | |
|---|---|---|
| *C07D 211/00* | (2006.01) |
| *A61K 31/53* | (2006.01) |
| *A61K 31/4439* | (2006.01) |
| *A61K 31/341* | (2006.01) |
| *A61K 31/381* | (2006.01) |
| *A61K 31/4184* | (2006.01) |
| *A61K 31/4196* | (2006.01) |
| *A61K 31/42* | (2006.01) |
| *A61K 31/425* | (2006.01) |
| *A61K 31/4406* | (2006.01) |
| *A61K 31/47* | (2006.01) |
| *A61K 31/5365* | (2006.01) |
| *A61K 45/06* | (2006.01) |
| *A61K 31/427* | (2006.01) |
| *A61K 31/4709* | (2006.01) |
| *C07D 261/14* | (2006.01) |
| *C07D 275/03* | (2006.01) |
| *C07D 401/04* | (2006.01) |
| *C07D 413/14* | (2006.01) |
| *C07D 417/12* | (2006.01) |
| *C07D 487/04* | (2006.01) |

(52) U.S. Cl.
CPC ............ *A61K 31/53* (2013.01); *A61K 31/341* (2013.01); *A61K 31/381* (2013.01); *A61K 31/4184* (2013.01); *A61K 31/4196* (2013.01); *A61K 31/42* (2013.01); *A61K 31/425* (2013.01); *A61K 31/427* (2013.01); *A61K 31/4406* (2013.01); *A61K 31/4439* (2013.01); *A61K 31/47* (2013.01); *A61K 31/4709* (2013.01); *A61K 31/5365* (2013.01); *A61K 45/06* (2013.01); *C07D 261/14* (2013.01); *C07D 275/03* (2013.01); *C07D 401/04* (2013.01); *C07D 413/14* (2013.01); *C07D 417/12* (2013.01); *C07D 487/04* (2013.01)

(58) Field of Classification Search
None
See application file for complete search history.

(56) References Cited

U.S. PATENT DOCUMENTS

| | | |
|---|---|---|
| 6,824,786 B2 | 11/2004 | Yu et al. |
| 2011/0098319 A1 | 4/2011 | Berni Canani et al. |
| 2011/0104162 A1 | 5/2011 | Carniato et al. |
| 2012/0010177 A1 | 1/2012 | Huang et al. |

FOREIGN PATENT DOCUMENTS

CA    WO 9116302 A1 * 10/1991 ............... A61K 8/46

OTHER PUBLICATIONS

International Search Report and Written Opinion for PCT International Application No. PCT/US2014/034354 issued Nov. 14, 2014.
PubChem Compound Summary for CID 51308659. Create Date May 3, 2011. [retrieved on Feb. 20, 2014] Retrieved from the Internet. <URL: https://pubchem.ncbi.nlm.nih.gov/compound/51308659?from=summary>.
Choi, et al., "Synthesis of Optically Active Amino Acid Derivatives via Dynamic Kinetic Resolution", J. Org. Chem. 74(24), 2009, 9543-9545.

* cited by examiner

*Primary Examiner* — Heide Reese
(74) *Attorney, Agent, or Firm* — Saul Ewing LLP; Kathryn Doyle; Domingos J. Silva

(57) ABSTRACT

The present invention provides compounds useful for treating or preventing a brain-related disease or disorder. The present invention further provides a method of treating or preventing a brain-related disease or disorder in a patient, the method comprising administering to the patient a pharmaceutical composition comprising at least one compound of the invention. The present invention further provides a method of modulating the activity of a monoamine transporter.

9 Claims, 31 Drawing Sheets

Fig. 3
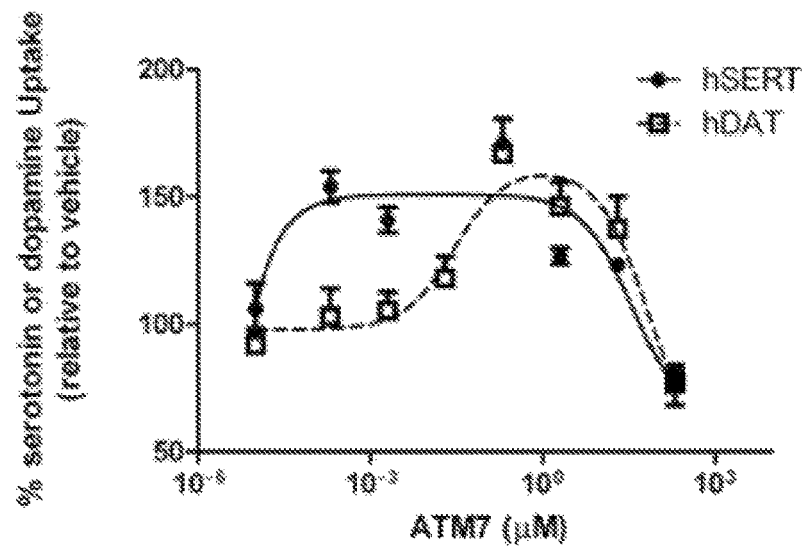
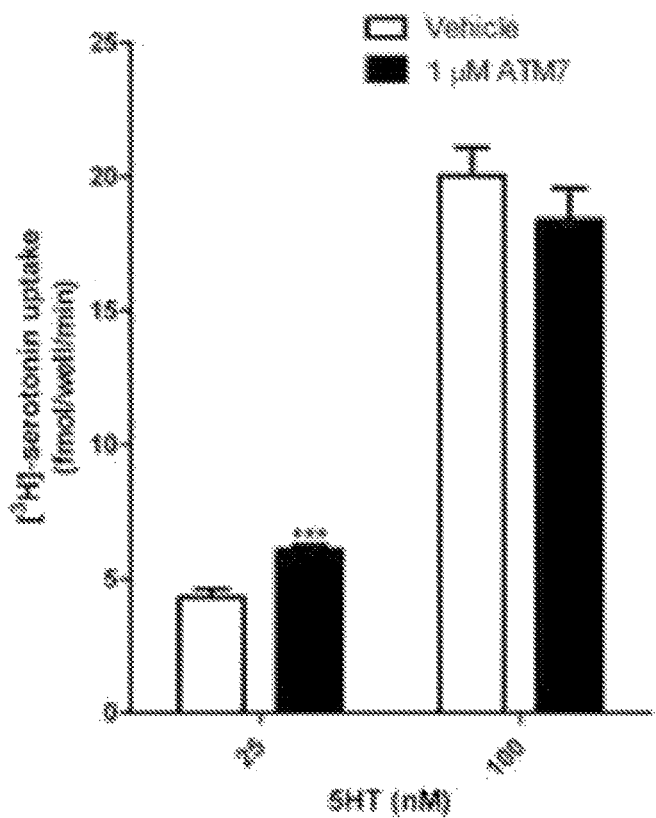

Fig. 4
A
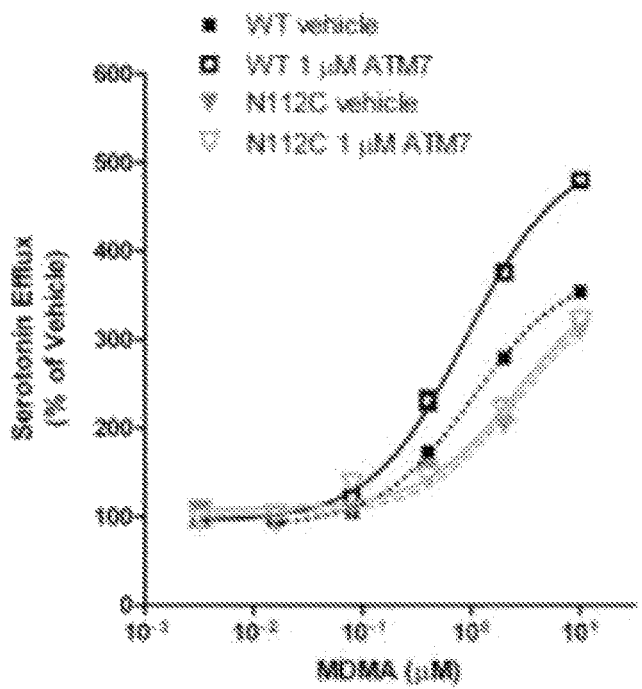
B
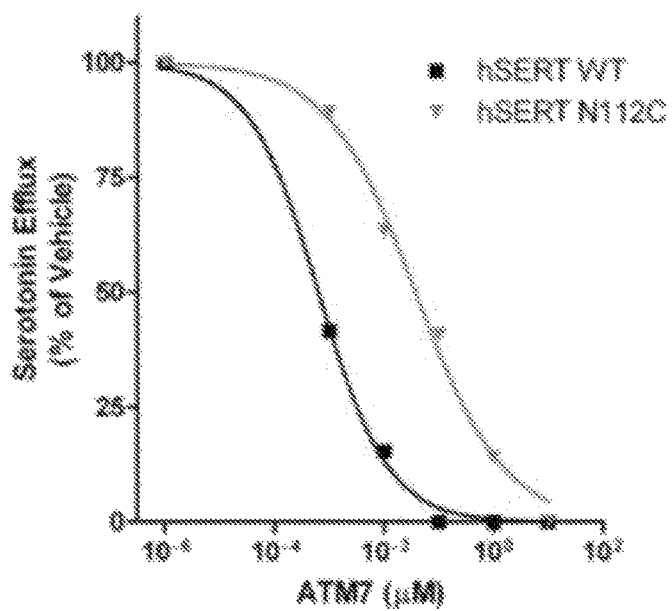

Fig. 8
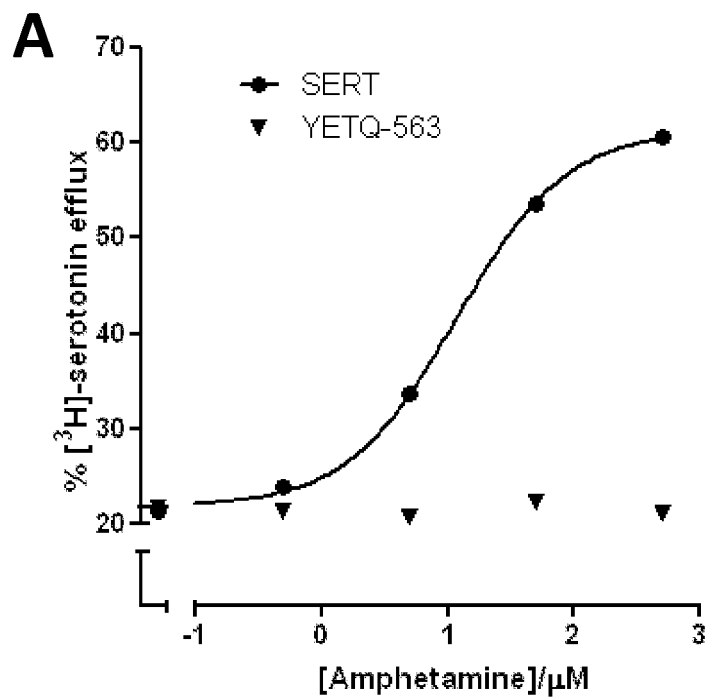
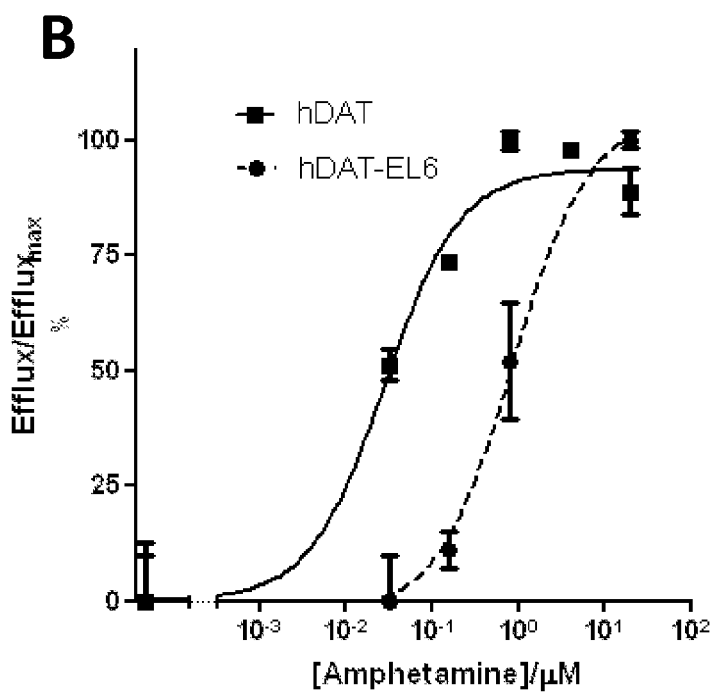

| | | | |
|---|---|---|---|
| ◯ polar | ····▸ sidechain acceptor | ◯ solvent residue | ◯◯ arene-arene |
| ◯ acidic | ◂···· sidechain donor | ◯ metal complex | ◯H arene-H |
| ◯ basic | ····▸ backbone acceptor | ···· solvent contact | ◯✢ arene-cation |
| ◯ greasy | ◂···· backbone donor | ···· metal/ion contact | |
| ⌒ proximity contour | ● ligand exposure | ◌ receptor exposure | |

KM822

ATM9 (KM409)

2-[5-({2-[(4-Fluorophenyl)amino]-2-oxoethyl}sulfanyl)-3-(4-pyridinyl)-1H-1,2,4-triazol-1-yl]-N-(3-methoxyphenyl)acetamide

| | | | |
|---|---|---|---|
| ○ polar | ⇢ sidechain acceptor | ○ solvent residue | ⬡⬡ arene-arene |
| ○ acidic | ⇠ sidechain donor | ○ metal complex | ⬡H arene-H |
| ○ basic | ⇢ backbone acceptor | ⋯ solvent contact | ⬡+ arene-cation |
| ○ greasy | ⇠ backbone donor | ⋯ metal/ion contact | |
| ◌ proximity contour | ● ligand exposure | ○ receptor exposure | |

COMPOSITIONS USEFUL IN TREATING BRAIN-RELATED DISEASES OR DISORDERS AND METHODS USING SAME

CROSS-REFERENCE TO RELATED APPLICATIONS

The present application is a 35 U.S.C. §371 national phase application from, and claims priority to, International Application No. PCT/US2014/034354, filed Apr. 16, 2014, and published under PCT Article 21(2) in English, which claims priority under 35 U.S.C. §119(e) to U.S. Provisional Application No. 61/812,401, filed Apr. 16, 2013, all of which applications are incorporated herein by reference in their entireties.

BACKGROUND OF THE INVENTION

Cocaine, amphetamine, methamphetamine, and methylenedioxy-methamphetamine (MDMA, or "ecstasy") top the list of widely abused psychostimulants. The proposed mechanism of action of these drugs is through the inhibition (in the case of cocaine) or reversal (in the case of amphetamines) of transporter function of the plasma membrane monoamine transporters (MATs), including the human dopamine transporter (hDAT) and the human serotonin transporter (hSERT).

Like most members of the solute carrier 6A family (SLC6A), serotonin (SERT), norepinephrine (NET), and dopamine (DAT) transporters are expressed on the plasma membrane, where they catalyze the uptake of their respective substrates. They clear the neurotransmitters from the extracellular space following synaptic release, and serve as important regulators of the signal amplitude and duration at the monoaminergic synapses that ultimately drive behaviors. Recently, the structures of LeuT, a bacterial homologue of MATs, in a substrate-bound occluded, substrate-free outward-open, and an apo inward-open state and also with competitive and noncompetitive inhibitors have been determined. Together with computational modeling and experimental data gathered over the past decade, these structures have dramatically facilitated the understanding of several aspects of SERT, NET, and DAT transporter function, including the molecular determinants of ligand interaction. These data have also enabled identification of important structures for ligand interaction. However, the binding pockets of cocaine to hDAT and hSERT have not been clearly established. Some studies point to either overlapping pockets or neighboring pockets separated by a set of aromatic residues called the aromatic lid near the salt bridge formed between R85 (transmembrane domain 1; TMD1) and D476 (transmembrane domain 10; TMD10) in DAT.

SERT serves as an important regulator of the signal amplitude and duration at the serotonergic synapses that ultimately drive serotonin-associated behaviors. SERT is pharmacologically interesting, being a target of several clinically relevant drugs including the classical tricyclic antidepressants, newer selective serotonin reuptake inhibitors (SSRIs), and psychostimulants including cocaine, amphetamine and MDMA.

SERT cDNAs have recently been isolated from the human parasite *Schistosoma mansoni*, and are designated as SmSERT and SmDAT. In both transporters, transport activities of their endogenous substrates were identical to their mammalian counterparts. However, in SmSERT, serotonin, but not other substrates such as amphetamine and MDMA, induced efflux in the parasite carrier. The parasite SERT also displays dramatically reduced affinity for several inhibitors, including cocaine and SSRIs.

Preliminary efforts to understand the structure and function of SERT involved homology modeling of these transporters using the crystal structures of members of the major facilitator superfamily (such as lactose permease symporter) as template (Abramson et al., 2003, Science 301:610-615; Ravna et al., 2006, Bioorg Med Chem 14:666-675). This model explained the binding mode of several substrates including S-methamphetamine and SSRIs. Further modeling efforts involved the use of the leucine transporter (LeuT) from a thermophilic bacteria, *Aquifex aeolicus* (Yamashita et al., 2005, Nature 437:215-223), which has provided a suitable template to understand the ion binding sites (Forrest et al., 2007, Proc Natl Acad Sci USA 104:12761-12766) and orthosteric and allosteric binding sites in serotonin and other monoamine transporters (Kitayama et al., 1992, Proc Natl Acad Sci USA 89:7782-7785; Sulzer et al, 2005, Prog Neurobiol 75:406-433; Beuming et al., 2008, Nat Neurosci 11:780-789; Forrest et al., 2008, Proc Natl Acad Sci USA 105:10338-10343). Adding to the initially determined structure, structures of LeuT in a substrate-free outward-open; a substrate-bound occluded; and an apo inward-open state have been determined (Krishnamurthy and Gouaux, 2012, Nature 481:469-474). Structures of LeuT in complex with competitive and noncompetitive inhibitors are also available (Rudnick, 2006, J Membr Biol 213:101-110; Singh et al., 2007, Nature 448:952-956; Zhou et al., 2007, Science 317: 1390-1393; Singh et al., 2008, Science 322:1655-1661; Zhou et al., 2009, Nat Struct Mol Biol 16:652-657). These LeuT structures were instrumental in developing homology models of SERT in both outward- and inward-open conformation and in determining the molecular interactions governing the ion binding, orthosteric, and psychostimulant binding sites (Rudnick, 2006, J Membr Biol 213:101-110; Celik et al., 2008, J Am Chem Soc 130:3853-3865; Manepalli et al., 2012, AAPS J 14:820-831). However, the binding pocket of psychostimulants to hDAT and hSERT has not been clearly established with some studies pointing to either overlapping pockets or neighboring pockets separated by a set of aromatic residues called the aromatic lid near the TM1-TM10 salt bridge formed between R85 and D476.

The hybrid structure-based (HSB) method (Kortagere and Welsh, 2006, J Comput Aided Mol Des 20:789-802) allows for screening small-molecule libraries and designing small-molecule inhibitors of therapeutically relevant targets. These include inhibitors of novel protein-protein interactions of the malarial parasite (Kortagere et al., 2010, J Chem Inf Model 50:840-849.), *Toxoplasma gondii* (Kortagere et al., 2011, J Comput Aided Mol Des 25:403-411; Kortagere, 2012, Expert Opin Drug Discov 7:1193-1206) and inhibitors that block the hexamerization of the HIV-1 capsid protein (Kortagere et al., 2012, Methods Mol Biol 929:359-375; Kortagere et al., 2012, J Virol 86:8472-8481). The HSB method was also instrumental in the design of atypical agonists of dopamine D3 receptor that bind to the receptor and modulate its function (Kuzhikandathil and Kortagere, 2012, Pharm Res 29:2264-2275). The key component of the HSB method is design of a three-dimensional pharmacophore using structural information derived from molecular dynamics (MD) simulations and known biochemical data, such as site-directed mutagenesis of key residues of the target protein. Hit molecules from the screening are subjected to several filtering schemes (Kortagere and Welsh, 2006, J Comput Aided Mol Des 20:789-802; Chekmarev et al., 2008, Chem Res Toxicol 21:1304-1314; Kortagere et al., 2008, Pharm Res 25:1836-1845; Kortagere et al., 2009;

Kortagere et al., 2012, Methods Mol Biol 929:359-375; Kortagere et al., 2012, J Virol 86:8472-8481) customized to every target. The best ranking compounds are then tested in in vitro assays.

Past studies have identified small molecule ligands that competitively inhibit the interactions of psychostimulants with receptors, transporters, ion channels or enzymes at their orthosteric site. However, these compounds have the potential to have psychostimulant properties. Thus, there is a need to design new compounds that are specific in their interaction with the transporters, efficacious in treating brain-related diseases or disorders, and free of side effects.

There is a need in the art for novel therapeutic agents that treat or prevent brain-related diseases or disorders involving aberrant monoamine signaling. The present invention fulfills this need.

BRIEF SUMMARY OF THE INVENTION

As described herein, the present invention relates to the unexpected discovery of novel compounds that modulate the activity of monoamine transporters (MATs) without interfering with their normal reuptake of endogenous neurotransmitters.

The invention includes a compound of the invention, as well as a pharmaceutical composition comprising a compound of the invention and a pharmaceutically acceptable carrier.

The invention further includes a method of treating or preventing a brain-related disease or disorder in a subject in need thereof, the method comprising administering to the subject a therapeutically effective amount of a pharmaceutical composition comprising at least one compound of the invention.

The invention further includes a method of modulating the activity of a monoamine transporter, the method comprising contacting the monoamine transporter with an effective amount of at least one compound of the invention, whereby the activity of the monoamine transporter is modulated.

The invention further includes a method of inducing a conformational change in a monoamine transporter, the method comprising contacting the monoamine transporter with an effective amount of at least one compound of the invention, whereby a conformational change is induced in the monoamine transporter.

In certain embodiments, the compound of the invention is selected from the group consisting of:
(i) a compound of Formula (I):

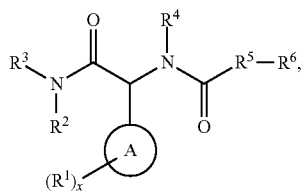

wherein in Formula (I),
ring A is a monocyclic or bicyclic aryl or a monocyclic or bicyclic heteroaryl ring, and wherein the aryl or heteroaryl ring is optionally substituted with 1-4 $R^1$ groups;
each occurrence of $R^1$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —OR', —$SR^7$, —S(=O)$R^7$, —S(=O)$_2R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —OC(=O)N($R^7$)$_2$, —NHC(=O)NH($R^7$), —NHC(=O)$R^7$, —NHC(=O)O$R^7$, —C(OH)($R^7$)$_2$, and —C($NH_2$)($R^7$)$_2$;

$R^2$ is selected from the group consisting of H, $C_1$-$C_6$ alkyl, —OR', —S(=O)$R^7$, —S(=O)$_2R^7$, —C(=O)$R^7$, —$CO_2R^7$, —CH($R^7$)$_2$, and —C(=O)N($R^7$)$_2$;

$R^3$ and $R^4$ are each independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), $C_4$-$C_{10}$ heterocyclyl, —$C_1$-$C_3$ alkyl-($C_4$-$C_{10}$ heterocyclyl), $C_6$-$C_{10}$ aryl, —$C_1$-$C_3$ alkyl-($C_6$-$C_{10}$ aryl), $C_5$-$C_{10}$ heteroaryl, and —$C_1$-$C_3$ alkyl-($C_5$-$C_{10}$ heteroaryl), wherein the alkyl, heteroalkyl, cycloalkyl, heterocyclyl, aryl and heteroaryl groups are independently optionally substituted;

$R^5$ is selected from the group consisting of $C_1$-$C_6$ alkanediyl, —($CH_2$)S(=O)$_{0-2}$($CH_2$)—, $C_3$-$C_{10}$ cycloalkanediyl, $C_4$-$C_{10}$ heterocyclediyl, $C_6$-$C_{10}$ arenediyl, and $C_5$-$C_{10}$ heteroarenediyl, wherein the alkanediyl, cycloalkanediyl, heterocyclediyl, arenediyl and heteroarenediyl groups are independently optionally substituted;

$R^6$ is selected from the group consisting of H, —OR', —S(=O)$R^7$, —S(=O)$_2R^7$, —C(=O)$R^7$, —$CO_2R^7$, —CH($R^7$)$_2$, and —C(=O)N($R^7$)$_2$;

each occurrence of $R^7$ is independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), $C_4$-$C_{10}$ heterocyclyl, —$C_1$-$C_3$ alkyl-($C_4$-$C_{10}$ heterocycle), $C_6$-$C_{10}$ aryl, —$C_1$-$C_3$ alkyl-($C_6$-$C_{10}$ aryl), $C_5$-$C_{10}$ heteroaryl, and —$C_1$-$C_3$ alkyl-($C_5$-$C_{10}$ heteroaryl), wherein the alkyl, heteroalkyl, cycloalkyl, heterocycle, aryl and heteroaryl groups are independently optionally substituted; and x is an integer from 0-4;
(ii) a compound of Formula (II):

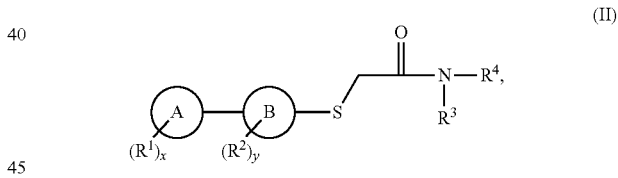

wherein in Formula (II),
ring A is a monocyclic or bicyclic aryl or a monocyclic or bicyclic heteroaryl ring, and wherein the aryl or heteroaryl ring is optionally substituted with 1-4 $R^1$ groups;
ring B is a monocyclic or bicyclic arenediyl or a monocyclic or bicyclic heteroarenediyl ring, and wherein the arenediyl or heteroarenediyl ring is optionally substituted with 1-4 $R^2$ groups;
each occurrence of $R^1$ and $R^2$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —S(=O)$_2R^5$, —($CH_2$)$_{0-2}$NHS(=O)$_2R^5$, —($CH_2$)$_{0-2}$C(=O)$R^5$, —OC(=O)$R^5$, —($CH_2$)$_{0-2}$$CO_2R^5$, —$OCO_2R^5$, —CH($R^5$)$_2$, —($CH_2$)$_{0-2}$N($R^5$)$_2$, —($CH_2$)$_{0-2}$C(=O)N($R^5$)$_2$, —OC(=O)N($R^5$)$_2$, ($CH_2$)$_{0-2}$NHC(=O)NH($R^5$), —($CH_2$)$_{0-2}$NHC(=O)$R^5$, —($CH_2$)$_{0-2}$NHC(=O)O$R^5$, —C(OH)($R^5$)$_2$, and —C($NH_2$)($R^5$)$_2$;

$R^3$ is selected from the group consisting of H, $C_1$-$C_6$ alkyl, —$OR^5$, —S(=O)$R^5$, —S(=O)$_2R^5$, —C(=O)$R^5$, —$CO_2R^5$, —CH($R^5$)$_2$, and —C(=O)N($R^5$)$_2$;

$R^4$ is selected from the group consisting of —$OR^5$, —$SR^5$, —$S(=O)R^5$, —$S(=O)_2R^5$, —$NHS(=O)_2R^5$, —$C(=O)R^5$, —$OC(=O)R^5$, —$CO_2R^5$, —$OCO_2R^5$, —$CH(R^5)_2$, —$N(R^5)_2$, —$C(=O)N(R^5)_2$, —$OC(=O)N(R^5)_2$, —$NHC(=O)NH(R^5)$, —$NHC(=O)R^5$, —$NHC(=O)OR^5$, —$C(OH)(R^5)_2$, —$C(NH_2)(R^5)_2$, $C_1$-$C_6$ alkyl, $C_3$-$C_{10}$ cycloalkyl, ($C_4$-$C_{10}$)heterocycle, ($C_6$-$C_{10}$)aryl, and ($C_5$-$C_{10}$) heteroaryl, wherein the alkyl, heteroalkyl, cycloalkyl, heterocycle, aryl and heteroaryl groups are independently optionally substituted;

each occurrence of $R^5$ is independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), ($C_4$-$C_{10}$)heterocycle, —$C_1$-$C_3$ alkyl-($C_4$-$C_{10}$ heterocycle), ($C_6$-$C_{10}$)aryl, —$C_1$-$C_3$ alkyl-($C_6$-$C_{10}$ aryl), ($C_5$-$C_{10}$)heteroaryl, and —$C_1$-$C_3$ alkyl-($C_5$-$C_{10}$ heteroaryl), wherein the alkyl, heteroalkyl, cycloalkyl, heterocycle, aryl and heteroaryl groups are independently optionally substituted; and x and y are independently an integer from 0-4;
(iii) a compound of Formula (III):

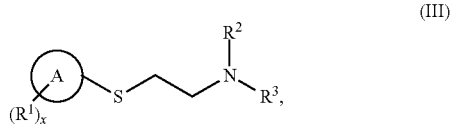

(III)

wherein in Formula (III), ring A is a monocyclic, bicyclic or tricyclic aryl or a monocyclic, bicyclic or tricyclic heteroaryl ring, and wherein the aryl or heteroaryl ring is optionally substituted with 1-4 $R^1$ groups;

each occurrence of $R^1$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^4$, —$SR^4$, —$S(=O)R^4$, —$S(=O)_2R^4$, —$NHS(=O)_2R^4$, —$C(=O)R^4$, —$OC(=O)R^4$, —$CO_2R^4$, —$OCO_2R^4$, —$CH(R^4)_2$, —$N(R^4)_2$, —$C(=O)N(R^4)_2$, —$OC(=O)N(R^4)_2$, —$NHC(=O)NH(R^4)$, —$NHC(=O)R^4$, —$NHC(=O)OR^4$, —$C(OH)(R^4)_2$, and —$C(NH_2)(R^4)_2$;

$R^2$ and $R^3$ are each independently selected from the group consisting of H, $C_1$-$C_6$ alkyl, —$OR^4$, —$S(=O)R^4$, —$S(=O)_2R^4$, —$C(=O)R^4$, —$CO_2R^4$, —$CH(R^4)_2$, and —$C(=O)N(R^4)_2$;

each occurrence of $R^4$ is independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), $C_4$-$C_{10}$ heterocycle, —$C_1$-$C_3$ alkyl-($C_4$-$C_{10}$ heterocycle), $C_6$-$C_{10}$ aryl, —$C_1$-$C_3$ alkyl-($C_6$-$C_{10}$ aryl), $C_5$-$C_{10}$ heteroaryl, and —$C_1$-$C_3$ alkyl-($C_5$-$C_{10}$ heteroaryl), wherein the alkyl, heteroalkyl, cycloalkyl, heterocycle, aryl and heteroaryl groups are independently optionally substituted; and x is an integer from 0-4;
a salt or solvate thereof, and any combinations thereof.

In certain embodiments, the at least one compound of Formula (I) is selected from the group consisting of 4-amino-$N^5$-{1-(4-hydroxy-3-methoxyphenyl)-2-[(3-methyl butyl)amino]-2-oxoethyl}-$N^5$-(3-hydroxypropyl)-1,2-thiazole-3,5-dicarboxamide; N-[2-(cyclohexylamino)-1-(3,4-dihydroxyphenyl)-2-oxoethyl]-N-(4-fluorophenyl)-2-({2-[(5-methyl-1,2-oxazol-3-yl)amino]-2-oxoethyl}sulfanyl)acetamide; N-[2-(cyclohexylamino)-2-oxo-1-(2-thienyl)ethyl]-2-({2-[(5-methyl-1,2-oxazol-3-yl)amino]-2-oxoethyl}sulfanyl)-N-(3-quinolinyl)acetamide; 4-amino-$N^5$-{2-(benzylamino)-1-[4-(dimethylamino)phenyl]-2-oxoethyl}-$N^5$-(3-pyridinylmethyl)-1,2-thiazole-3,5-dicarboxamide; N-(2-furylmethyl)-N-{1-(4-hydroxyphenyl)-2-[(3-methylbutyl)amino]-2-oxoethyl}-N'-(1,3-thiazol-2-yl)succinamide; a salt thereof, a solvate thereof, and any combinations thereof.

In certain embodiments, the at least one compound of formula (II) is selected from the group consisting of N-[4-(cyclopropylsulfamoyl)phenyl]-2-{[5-(5,6-dimethyl-1H-benzimidazol-2-yl)-2-pyridinyl]sulfanyl}acetamide, 3-hydroxy-N'-({[4-(3-methoxypropyl)-5-(4-pyridinyl)-4H-1,2,4-triazol-3-yl]sulfanyl}acetyl)benzohydrazide; N-(4-fluorophenyl)-2-((4-(2-((3-methoxyphenyl)amino)-2-oxoethyl)-5-(pyridin-4-yl)-4H-1,2,4-triazol-3-yl)thio) acetamide, a salt thereof, a solvate thereof, and any combinations thereof.

In certain embodiments, the at least one compound of Formula (III) is selected from the group consisting of N-[4-({2-[(8-ethyl-5H-[1,2,4]triazino[5,6-b]indol-3-yl)sulfanyl]ethyl}sulfamoyl)phenyl]acetamide, a salt thereof, a solvate thereof, and any combinations thereof.

In certain embodiments, the brain-related disease or disorder is at least one selected from the group consisting of attention deficit hyperactivity disorder (ADHD), schizophrenia, drug addiction, smoking addiction, eating disorders, obsessive-compulsive disorder, depression, an anxiety disorder, an affective disorder, traumatic brain injury, stroke, cognitive disorders and narcolepsy.

In certain embodiments, the subject is further administered at least one additional therapeutic agent. In other embodiments, the pharmaceutical composition is co-administered to the subject with the at least one additional therapeutic agent. In yet other embodiments, the pharmaceutical composition is administered to the subject a given period of time before or after the at least one additional therapeutic agent is administered to the subject.

In certain embodiments, the compound enhances uptake of at least one neurotransmitter in the subject. In other embodiments, the compound enhances efflux of at least one neurotransmitter in the subject. In yet other embodiments, the neurotransmitter comprises at least one selected from the group consisting of serotonin, norepinephrine, and dopamine. In yet other embodiments, the compound inhibits the binding of at least one additional agent to a monoamine transmitter. In yet other embodiments, the additional agent comprises a psychostimulant or antidepressant.

In certain embodiments, the subject is a mammal. In other embodiments, the mammal is a human.

In certain embodiments, the monoamine transporter is selected from the group consisting of a serotonin transporter, a norepinephrine transporter, a dopamine transporter, and any combinations thereof. In other embodiments, the monoamine transporter is derived from a mammal. In yet other embodiments, the monoamine transporter is in vivo.

The invention provides novel compounds with surprising biological activity, compositions comprising the same, and methods of treating or preventing brain-related diseases or disorders involving aberrant monoamine signaling. Compositions and articles defined by the invention were isolated or otherwise manufactured in connection with the examples provided below. Other features and advantages of the invention will be apparent from the detailed description, and from the claims.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIGS. 2A-2B, illustrates a three-dimensional structural model of hSERT in a top view with the extracellular region facing up. FIG. 2A is an illustration of hSERT (colored orange), with the residues lining the allosteric site shown as sticks colored by atom type (C, cyan; O, red; N, blue). The hydrogen atoms were not displayed for clarity. FIG. 2B is a cartoon representation illustrating the residues lining the allosteric site (as depicted in FIG. 2A) with the pharmacophore elements overlaid. Green circle represents a hydrophobic/aromatic element and yellow circles represent hydrogen bond donor/acceptor pair elements of the pharmacophore. Distances observed during the production phase of MD simulation between the four residues were utilized as distance constraints in the pharmacophore, as depicted by black lines.

FIG. 3, comprising FIGS. 3A-3B, illustrates the finding that ATM7 displays complex biphasic activity towards SERT and DAT uptake activity. FIG. 3A is a graph illustrating the finding that hSERT was more sensitive to ATM7 than hDAT. Following ATM7 preincubation at various concentrations for 10 min, hSERT- or hDAT-expressing cells were tested for uptake activity. FIG. 3B is a graph illustrating the finding that ATM7 was tested for its effects on hSERT uptake activity at low and high concentrations of substrate (25 and 100 nM, respectively) and displayed activity only at low concentrations (*$p<0.05$, one-way ANOVA with Dunnett's multiple-comparison test, comparing vehicle and ATM7 treatments).

FIG. 4, comprising FIGS. 4A-4B, illustrates the modulation of hSERT efflux by ATM7 through allosteric site (N112C). FIG. 4A is a graph illustrating the finding that ATM7 was tested for its effects on MDMA-elicited efflux. Only wild-type (WT) but not a mutant of the predicted ATM7 binding pocket, 112C, displayed enhanced MDMA-elicited efflux in the presence of 1 µM ATM7. FIG. 4B is a graph illustrating the finding that ATM7 was tested for its effects on basal/leak efflux. Basal/leak efflux was inhibited by ATM7 and the 112C mutant displayed lower sensitivity to ATM7 compared with WT.

FIGS. 6A-6B, illustrates a structural model of hSERT with ATM7 docked to the allosteric site. FIG. 6A is an image illustrating a structural model of hSERT represented as orange ribbons with ATM7 docked at the allosteric site shown in an orientation parallel to the membrane. FIG. 6B is a schematic representation of the interactions of ATM7 at the allosteric site. The legend illustrates the nature of interactions. This figure was generated using the LIGX module of the modeling program MOE (Molecular Operating Environment; Chemical Computing Group, Montreal, Quebec, Canada).

FIG. 8, comprising FIGS. 8A-8B, illustrates amphetamine-mediated efflux for SERT (FIG. 8A) and hDAT (FIG. 8B) for WT and mutant forms.

FIG. 10, comprising FIG. 10A is a graph illustrating assay results for compound ATM1 (KM-456). FIG. 10B is a graph illustrating assay results for compound ATM2 (KM-571). FIG. 10C is a graph illustrating assay results for compound ATM5 (KM-822). FIG. 10D is a graph illustrating assay results for compound ATM7 (KM-986).

FIGS. 11A-11B, illustrates the effect of ATM1 (KM-456) on SERT/SSRI interaction. FIG. 11A is a graph illustrating the effect of ATM1 on SERT/citalopram interaction. FIG. 11B is a graph illustrating the effect of ATM1 on SERT/fluoxetine interaction.

FIGS. 12A-12B, illustrates the effect of ATM2 (KM-571) on DAT (FIG. 12A) and NET (FIG. 12B) interaction with amphetamine. ATM2 decreases $IC_{50}$ of amphetamine for inhibiting DAT-mediated uptake.

FIGS. 13A-13B, illustrates that ATM5 (KM-822) modulates amphetamine-induced efflux. FIG. 13A is a graph illustrating that amphetamine-induced efflux is modulated by ATM5 in hDAT WT. FIG. 13B is a graph illustrating that amphetamine-induced efflux is modulated by ATM5 in N93A.

FIG. 14, comprising FIG. 14A is a graphic illustrating the interactions of ATM1 with the residues. FIG. 14B is a graphic illustrating the interactions of ATM2 with the residues. The orange colored circles indicate positions on the ligands that are optimized using other hydrogen bond donor-acceptor groups to strengthen the interactions of the ligands with hSERT. The magenta circles indicate positions on the ligands that are optimized with other mono, di or tri substituted hetero aryl groups to facilitate aromatic π-stacking and arene-cation interactions.

FIG. 16, comprising FIG. 16A is a graph illustrating results of dopamine uptake inhibition assays with cocaine demonstrating a decreased affinity for cocaine in the presence of ATM5. FIG. 16B is a graph illustrating results of dopamine uptake inhibition assays with amphetamine demonstrating a decreased affinity for amphetamine in the presence of ATM5.

FIG. 18, comprising FIG. 18A is a schematic view of the interactions of ATM5 with residues in site A1. The legend below the figure details the nature of the interactions. FIG. 18B is a scheme illustrating the design of analogues of ATM5 based on their interactions at the binding site in A1.

FIG. 19, comprising

FIGS. 28A-28C, is a set of graphs illustrating the results of hDAT, hNET, and hSERT uptake assays with transporter modulators KM-409, KM-456, and KM-822.

FIGS. 29A-29C, is a set of graphs illustrating the finding that the transporter/inhibitor interaction is affected by allosteric modulators. KM-409 and KM-456 increased $IC_{50}$ of citalopram for inhibiting SERT-mediated serotonin uptake, and KM-822 increased the $IC_{50}$ of cocaine for inhibiting DAT-mediated dopamine uptake.

FIG. 30, comprising FIG. 30A: KM-456 was shown to inhibit SERT function through interaction with extracellular gate. When the extracellular gate was mutated (E493D) the transporter was not affected by KM-456. FIG. 30B: KM-456 was shown to inhibit SERT function through a non-competitive mechanism. Both $V_{max}$ and $K_M$ of SERT was affected by KM-456.

DETAILED DESCRIPTION OF THE INVENTION

Figure 1:
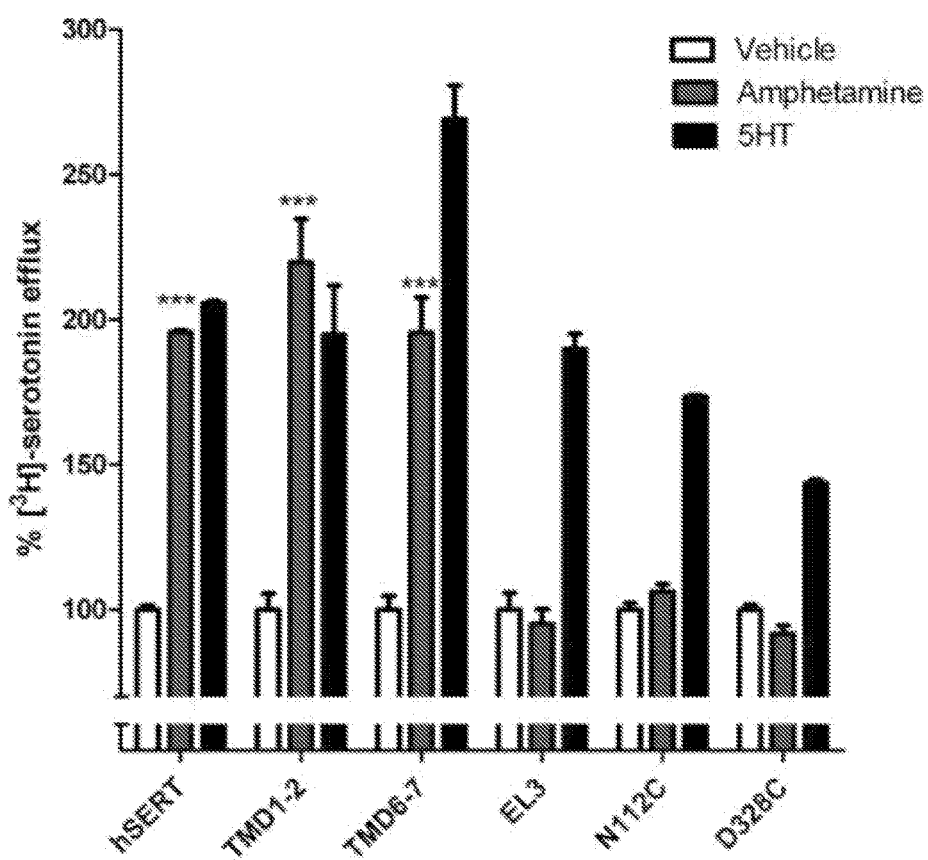
FIG. 1 is a graph illustrating the finding that chimeras reveal involvement of extracellular domains in SERT/substrate interaction. Efflux assays were performed on chimeras between human and parasite SERT and mutants of human SERT. Human SERT with TMD1-2 or TMD6-7 replaced with the corresponding parasite domains elicited amphetamine-mediated efflux. Conversely, human SERT with EL3 replaced with the corresponding parasite loop displayed no significant amphetamine-mediated efflux. Mutants within the allosteric pocket (N112C and D328C) also displayed no significant amphetamine-elicited efflux (***$p<0.001$, comparing amphetamine to vehicle in the different groups, one-way ANOVA followed by Bonferroni's multiple-comparison test).

The present invention relates to the discovery of a novel mechanism for modulating the activity of at least one monoamine transporter (MAT) without interfering with its normal reuptake of endogenous neurotransmitters. In a brain-related disease or disorder comprising altered MAT function, reuptake of the neurotransmitter associated with the MAT may be abnormal and might contribute to the pathology of the brain-related disease or disorder.

In a non-limiting aspect, allosteric transporter modulator (ATM)-induced binding is associated with a unique conformational state of the transporter. In one embodiment, MAT activity, and therefore neurotransmitter signaling, can be modulated with compounds that induce this conformational state. As disclosed herein, allosteric binding pockets were identified on human serotonin transporter (hSERT), and small molecules were designed that bind to these sites and regulate MAT function. A pharmacophore model based on the interactions of ATM compounds with MATs was designed as an input to the Hybrid Structure Based (HSB) in silico screening method, allowing the identification of novel modulators ATM5 and ATM7, which bind to the site and induce the conformational state of the MAT, thus regulating MAT function.

The present invention further relates to the discovery of a novel class of allosteric monoamine transporter modulators, which regulate MAT function. In one embodiment, the modulators or compounds of the invention bind to an allosteric binding site on the MAT and induce a conformational change in the MAT. In another embodiment, the compounds of the invention enhance uptake of a neurotransmitter. In yet another embodiment, the compounds of the invention enhance efflux of a neurotransmitter. In yet another embodiment, the compounds of the invention inhibit the binding of at least one additional compound to a MAT. Non-limiting examples of the at least one additional compound include psychostimulants and antidepressants.

The functional properties of the compounds of the invention was characterized by studying their ability to bind to allosteric binding pockets on a MAT, and induce a conformational change in the MAT. In one embodiment, the compounds of the invention are useful in treating or preventing a brain-related disease or disorder in patients in need thereof. In another embodiment, the compounds of the invention are useful in treating neurological disorders in which monoamine transporter function is aberrant.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" as used herein, when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl, as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxy cyclopentyl and 3-chloropropyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

As used herein, the term "ATM" refers to allosteric transporter modulator.

As used herein, the term "ATM1" or "K456" or "KM-456" refers to the compound N-[4-(cyclopropylsulfamoyl) phenyl]-2-{[5-(5,6-dimethyl-1H-benzimidazol-2-yl)-2-pyridinyl]sulfanyl}acetamide, or a salt or solvate thereof.

As used herein, the term "ATM2" or "K571" or "KM-571" refers to the compound 4-amino-$N^5$-{1-(4-hydroxy-3-methoxyphenyl)-2-[(3-methylbutyl)amino]-2-oxoethyl}-$N^5$-(3-hydroxypropyl)-1,2-thiazole-3,5-dicarboxamide, or a salt or solvate thereof.

As used herein, the term "ATM3" or "K761" or "KM-761" refers to the compound 3-hydroxy-N'-({[4-(3-methoxypropyl)-5-(4-pyridinyl)-4H-1,2,4-triazol-3-yl] sulfanyl}acetyl)benzohydrazide, or a salt or solvate thereof.

As used herein, the term "ATM4" or "K779" or "KM-779" refers to the compound N-[2-(cyclohexylamino)-1-(3,4-dihydroxyphenyl)-2-oxoethyl]-N-(4-fluorophenyl)-2-({2-[(5-methyl-1,2-oxazol-3-yl)amino]-2-oxoethyl}sulfanyl) acetamide, or a salt or solvate thereof.

As used herein, the term "ATM5" or "K822" or "KM-822" refers to the compound N-[4-({2-[(8-ethyl-5H-[1,2,4] triazino[5,6-b]indol-3-yl)sulfanyl]ethyl sulfamoyl)phenyl] acetamide, or a salt or solvate thereof.

As used herein, the term "ATM6" or "K836" or "KM-836" refers to the compound N-[2-(cyclohexylamino)-2-oxo-1-(2-thienyl)ethyl]-2-({2-[(5-methyl-1,2-oxazol-3-yl) amino]-2-oxoethyl}sulfanyl)-N-(3-quinolinyl)acetamide, or a salt or solvate thereof.

As used herein, the term "ATM7" or "K986" or "KM-986" refers to the compound 4-amino-$N^5$-{2-(benzylamino)-1-[4-(dimethylamino)phenyl]-2-oxoethyl}-$N^5$-(3-pyridinylmethyl)-1,2-thiazole-3,5-dicarboxamide, or a salt or solvate thereof.

As used herein, the term "ATM8" or "K987" or "KM-987" refers to the compound N-(2-furylmethyl)-N-{1-(4-hydroxyphenyl)-2-[(3-methylbutyl)amino]-2-oxoethyl}-N'-(1,3-thiazol-2-yl)succinamide, or a salt or solvate thereof.

As used herein, the term "K409" or "KM-409" refers to the compound N-(4-fluorophenyl)-2-((4-(2-((3-methoxyphenyl)amino)-2-oxoethyl)-5-(pyridin-4-yl)-4H-1,2,4-triazol-3-yl)thio)acetamide, or a salt or solvate thereof.

As used herein, the term "brain-related disease or disorder" refers to any disease or disorder that causes malfunction of the brain or any cell thereof, thus causing a physiological, psychological or neurological disease or disorder. Non-limiting examples of brain-related diseases and disorders are attention deficit hyperactivity disorder (ADHD), schizophrenia, drug addiction, smoking addiction, eating disorders (including inability to maintain medically healthy weight), obsessive-compulsive disorder, various forms of depression, anxiety disorders, affective disorders, traumatic brain injury, stroke, cognitive disorders and narcolepsy. In one embodiment, the brain-related disease or disorder comprises aberrant monoamine signaling.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a brain-related disease or disorder in a patient.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "MAT" refers to a monoamine transporter.

As used herein, the term "patient" or "subject" or "individual" refers to a human or a non-human mammal. Non-human mammals include, for example, livestock and pets, such as ovine, bovine, porcine, canine, feline and murine mammals. Preferably, the patient or subject is human.

As used herein, the term "pharmaceutical composition" refers to a mixture of at least one compound useful in the methods of the invention with a pharmaceutically acceptable carrier. The pharmaceutical composition facilitates administration of the compound to a patient. Multiple techniques of administering a compound exist in the art including, but not limited to, intravenous, oral, aerosol, parenteral, ophthalmic, pulmonary and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful in the methods of the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful in the methods of the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful in the methods of the invention, and are physiologically acceptable to the patient. Supplementary active compounds may also be incorporated into the compositions. The "pharmaceutically acceptable carrier" may further include a pharmaceutically acceptable salt of the compound useful in the methods of the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "salts" embraces addition salts of free acids that are useful within the methods of the invention. In one embodiment, the salts are pharmaceutically acceptable salts. The language "pharmaceutically acceptable salt" refers to a salt of the administered compounds prepared from pharmaceutically acceptable non-toxic acids, including inorganic acids, organic acids, solvates, hydrates, or clathrates thereof. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxy benzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluene sulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_1$-$C_6$ alkyl, —OH, $C_1$-$C_6$ alkoxy, halo, amino, acetamido and nitro. In yet another embodiment, the substituents are independently selected from the group consisting of $C_1$-$C_6$ alkyl, $C_1$-$C_6$ alkoxy, halo, acetamido, and nitro. As used herein, where a substituent is an alkyl or alkoxy group, the carbon chain may be branched, straight or cyclic, with straight being preferred.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a brain-related disease or disorder, a symptom of a brain-related disease or disorder, or the potential to develop a brain-related disease or disorder, with the purpose to cure, heal, alleviate, relieve, alter, remedy, ameliorate, improve or affect a brain-related disease or disorder, the symptoms of a brain-related disease or disorder or the potential to develop a brain-related disease or disorder. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the unexpected discovery of novel compounds that bind to and modulate at least one monoamine transporter (MAT). In one embodiment, the MAT is selected from the group consisting of a serotonin transporter, a norepinephrine transporter, a dopamine transporter, and any combinations thereof. In another embodiment, the compound of the invention is a MAT modulator.

The compounds of the invention may be used to treat or prevent brain-related diseases and disorders, such as but not limited to, attention deficit hyperactivity disorder (ADHD), schizophrenia, drug addiction, smoking addiction, eating disorders (including inability to maintain medically healthy weight), obsessive-compulsive disorder, various forms of depression, anxiety disorders, affective disorders, traumatic brain injury, stroke, cognitive disorders and/or narcolepsy. In one embodiment, the compounds of the invention are useful in treating an indication where modulating the activity of a MAT is therapeutically beneficial. In another embodiment, a MAT mediates the therapeutic effect elicited by the compounds of the invention. In yet another embodiment, a MAT does not mediate the therapeutic effect elicited by the compounds of the invention.

In one embodiment, the compounds of the present invention bind to a region of a MAT. In another embodiment, binding of a compound of the invention to a MAT prevents, inhibits, and/or reduces the ability of the MAT to bind to at least one additional therapeutic or naturally occurring agent. In yet another embodiment, the binding of a compound of the invention to a MAT enhances the ability of the MAT to bind to at least one additional therapeutic or naturally occurring agent.

The present invention includes a composition comprising at least one compound of the invention, optionally further comprising at least one additional therapeutic agent. In one embodiment, the compound of the invention is a MAT-modulating compound. In another embodiment, the additional therapeutic agent binds to and modulates a MAT. In yet another embodiment, the additional therapeutic agent is a psychostimulant agent. In yet another embodiment, the additional therapeutic agent is an antidepressant.

In one embodiment, the compounds of the invention have improved drug-like properties over compounds known in the art to bind to and modulate a MAT.

Compounds

The compounds useful in the methods of the invention may be synthesized using techniques well-known in the art of organic synthesis.

In one aspect, the compound useful in the methods of the invention has the Formula (I):

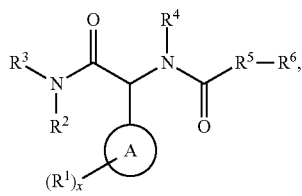

wherein in Formula (I), ring A is a monocyclic or bicyclic aryl or a monocyclic or bicyclic heteroaryl ring, and wherein the aryl or heteroaryl ring is optionally substituted with 1-4 $R^1$ groups;

each occurrence of $R^1$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —OR', —$SR^7$, —S(=O)$R^7$, —S(=O)$_2R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —OC(=O)N($R^7$)$_2$, —NHC(=O)NH($R^7$), —NHC(=O)$R^7$, —NHC(=O)O$R^7$, —C(OH)($R^7$)$_2$, and —C($NH_2$)($R^7$)$_2$;

$R^2$ is selected from the group consisting of H, $C_1$-$C_6$ alkyl, —OR', —S(=O)$R^7$, —S(=O)$_2R^7$, —C(=O)$R^7$, —$CO_2R^7$, —CH($R^7$)$_2$, and —C(=O)N($R^7$)$_2$;

$R^3$ and $R^4$ are each independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), $C_4$-$C_{10}$ heterocyclyl, —$C_1$-$C_3$ alkyl-($C_4$-$C_{10}$ heterocyclyl), $C_6$-$C_{10}$ aryl, —$C_1$-$C_3$ alkyl-($C_6$-$C_{10}$ aryl), $C_5$-$C_{10}$ heteroaryl, and —$C_1$-$C_3$ alkyl-($C_5$-$C_{10}$ heteroaryl), wherein the alkyl, heteroalkyl, cycloalkyl, heterocyclyl, aryl and heteroaryl groups are independently optionally substituted;

$R^5$ is selected from the group consisting of $C_1$-$C_6$ alkanediyl, —($CH_2$)S(=O)$_{0-2}$($CH_2$)—, $C_3$-$C_{10}$ cycloalkanediyl, $C_4$-$C_{10}$ heterocyclediyl, $C_6$-$C_{10}$ arenediyl, and $C_5$-$C_{10}$ heteroarenediyl, wherein the alkanediyl, cycloalkanediyl, heterocyclediyl, arenediyl and heteroarenediyl groups are independently optionally substituted;

$R^6$ is selected from the group consisting of H, —$O^7$, —S(=O)$R^7$, —S(=O)$_2R^7$, —C(=O)$R^7$, —$CO_2R^7$, —CH($R^7$)$_2$, and —C(=O)N($R^7$)$_2$;

each occurrence of $R^7$ is independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), $C_4$-$C_{10}$ heterocyclyl, —$C_1$-$C_3$ alkyl-($C_4$-$C_{10}$ heterocycle), $C_6$-$C_{10}$ aryl, —$C_1$-$C_3$ alkyl-($C_6$-$C_{10}$ aryl), $C_5$-$C_{10}$ heteroaryl, and —$C_1$-$C_3$ alkyl-($C_5$-$C_{10}$ heteroaryl), wherein the alkyl, heteroalkyl, cycloalkyl, heterocycle, aryl and heteroaryl groups are independently optionally substituted; and x is an integer from 0-4, or a salt or solvate thereof.

In certain embodiments, in (I) A is phenyl, thiophenyl, furyl, pyrryl, pyrazinyl, imidazolyl, pyridinyl or pyrimidinyl.

In certain embodiments, in (I) each occurrence of $R^1$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —$OR^7$, —$SR^7$, —S(=O)$R^7$, —S(=O)$_2R^7$, —NHS(=O)$_2R^7$, —CH($R^7$)$_2$, —N($R^7$)$_2$, NHC(=O)$R^7$, and —NHC(=O)O$R^7$.

In certain embodiments, in (I) $R^2$ is H, or $C_1$-$C_6$ alkyl.

In certain embodiments, in (I) $R^3$ and $R^4$ are independently selected from the group consisting of H, $C_1$-$C_6$ alkyl, $C_3$-$C_{10}$ cycloalkyl, —$C_1$-$C_3$ alkyl-($C_3$-$C_6$ cycloalkyl), $C_6$-$C_{10}$ aryl, —$C_1$-$C_3$ alkyl-($C_6$-$C_{10}$ aryl), $C_5$-$C_{10}$ heteroaryl, and —$C_1$-$C_3$ alkyl-($C_5$-$C_{10}$ heteroaryl), wherein the alkyl, cycloalkyl, aryl and heteroaryl groups are independently optionally substituted.

In certain embodiments, in (I) $R^5$ is selected from the group consisting of $C_1$-$C_6$ alkanediyl, —($CH_2$)S(=O)$_{0-2}$($CH_2$)—, $C_4$-$C_{10}$ heterocyclediyl, $C_6$-$C_{10}$ arenediyl, and $C_5$-$C_{10}$ heteroarenediyl, wherein the alkanediyl, heterocyclediyl, arenediyl and heteroarenediyl groups are independently optionally substituted.

In certain embodiments, in (I) $R^6$ is selected from the group consisting of H, —$OR^7$, —C(=O)$R^7$, —$CO_2R^7$, — and —C(=O)N($R^7$)$_2$.

In another aspect, the compound useful in the methods of the invention has the Formula (II):

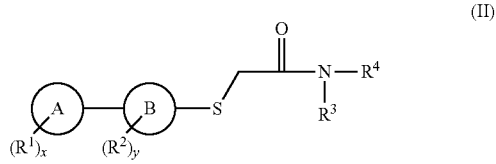

wherein in Formula (II), ring A is a monocyclic or bicyclic aryl or a monocyclic or bicyclic heteroaryl ring, and wherein the aryl or heteroaryl ring is optionally substituted with 1-4 $R^1$ groups;

ring B is a monocyclic or bicyclic arenediyl or a monocyclic or bicyclic heteroarenediyl ring, and wherein the arenediyl or heteroarenediyl ring is optionally substituted with 1-4 $R^2$ groups;

each occurrence of $R^1$ and $R^2$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —S(=O)$_2R^5$, —(CH$_2$)$_{0-2}$NHS(=O)$_2R^5$, —(CH$_2$)$_{0-2}$C(=O)$R^5$, —OC(=O)$R^5$, —(CH$_2$)$_{0-2}$CO$_2R^5$, —OCO$_2R^5$, —CH($R^5$)$_2$, —(CH$_2$)$_{0-2}$N($R^5$)$_2$, —(CH$_2$)$_{0-2}$C(=O)N($R^5$)$_2$, —OC(=O)N($R^5$)$_2$, (CH$_2$)$_{0-2}$NHC(=O)NH($R^5$), —(CH$_2$)$_{0-2}$NHC(=O)$R^5$, —(CH$_2$)$_{0-2}$NHC(=O)O$R^5$, —C(OH)($R^5$)$_2$, and —C(NH$_2$)($R^5$)$_2$;

$R^3$ is selected from the group consisting of H, $C_1$-$C_6$ alkyl, —$OR^5$, —S(=O)$R^5$, —S(=O)$_2R^5$, —C(=O)$R^5$, —CO$_2R^5$, —CH($R^5$)$_2$, and —C(=O)N($R^5$)$_2$;

$R^4$ is selected from the group consisting of —$OR^5$, —$SR^5$, —S(=O)$R^5$, —S(=O)$_2R^5$, —NHS(=O)$_2R^5$, —C(=O)$R^5$, —OC(=O)$R^5$, —CO$_2R^5$, —OCO$_2R^5$, —CH($R^5$)$_2$, —N($R^5$)$_2$, —C(=O)N($R^5$)$_2$, —OC(=O)N($R^5$)$_2$, —NHC(=O)NH($R^5$), —NHC(=O)$R^5$, —NHC(=O)O$R^5$, —C(OH)($R^5$)$_2$, —C(NH$_2$)($R^5$)$_2$, $C_1$-$C_6$ alkyl, $C_3$-$C_{10}$ cycloalkyl, ($C_4$-$C_{10}$)heterocycle, ($C_6$-$C_{10}$)aryl, and ($C_5$-$C_{10}$) heteroaryl, wherein the alkyl, heteroalkyl, cycloalkyl, heterocycle, aryl and heteroaryl groups are independently optionally substituted;

each occurrence of $R^5$ is independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), ($C_4$-$C_{10}$)heterocycle, —$C_1$-$C_3$ alkyl-($C_4$-$C_{10}$ heterocycle), ($C_6$-$C_{10}$)aryl, —$C_1$-$C_3$ alkyl-($C_6$-$C_{10}$ aryl), ($C_5$-$C_{10}$)heteroaryl, and —$C_1$-$C_3$ alkyl-($C_5$-$C_{10}$ heteroaryl), wherein the alkyl, heteroalkyl, cycloalkyl, heterocycle, aryl and heteroaryl groups are independently optionally substituted; and x and y are independently an integer from 0-4,
or a salt or solvate thereof.

In certain embodiments, in (II) ring A is benzediyl (phenylene), pyridinediyl, pyrazinediyl, triazenediyl, imidazoldiyl, oxazolediyl, or pyrrolediyl.

In certain embodiments, in (II) ring B is benzoimidazolyl, pyridinyl or phenyl.

In certain embodiments, in (II) each occurrence of $R^1$ and $R^2$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —(CH$_2$)$_{0-2}$NHS(=O)$_2R^5$, —(CH$_2$)$_{0-2}$CO$_2R^5$, —(CH$_2$)$_{0-2}$N($R^5$)$_2$, —(CH$_2$)$_{0-2}$C(=O)N($R^5$)$_2$, —OC(=O)N($R^5$)$_2$, —(CH$_2$)$_{0-2}$NHC(=O)$R^5$, and —(CH$_2$)$_{0-2}$NHC(=O)O$R^5$.

In certain embodiments, in (II) $R^3$ is H or $C_1$-$C_6$ alkyl. In certain embodiments, in (II) $R^4$ is selected from the group consisting of —$OR^5$, —NHS(=O)$_2R^5$, —NHC(=O)$R^5$, $C_1$-$C_6$ alkyl, $C_3$-$C_{10}$ cycloalkyl, $C_4$-$C_{10}$ heterocycle, $C_6$-$C_{10}$ aryl, and $C_5$-$C_{10}$ heteroaryl, wherein the alkyl, heteroalkyl, cycloalkyl, heterocycle, aryl and heteroaryl groups are independently optionally substituted.

In another aspect, the compound useful in the methods of the invention has the Formula (III):

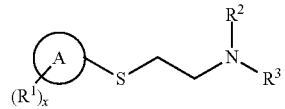

(III)

wherein in Formula (III), ring A is a monocyclic, bicyclic or tricyclic aryl or a monocyclic, bicyclic or tricyclic heteroaryl ring, and wherein the aryl or heteroaryl ring is optionally substituted with 1-4 $R^1$ groups;

each occurrence of $R^1$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^4$, —$SR^4$, —S(=O)$R^4$, —S(=O)$_2R^4$, —NHS(=O)$_2R^4$, —C(=O)$R^4$, —OC(=O)$R^4$, —CO$_2R^4$, —OCO$_2R^4$, —CH($R^4$)$_2$, —N($R^4$)$_2$, —C(=O)N($R^4$)$_2$, —OC(=O)N($R^4$)$_2$, —NHC(=O)NH($R^4$), —NHC(=O)$R^4$, —NHC(=O)O$R^4$, —C(OH)($R^4$)$_2$, and —C(NH$_2$)($R^4$)$_2$;

$R^2$ and $R^3$ are each independently selected from the group consisting of H, $C_1$-$C_6$ alkyl, —$OR^4$, —S(=O)$R^4$, —S(=O)$_2R^4$, —C(=O)$R^4$, —CO$_2R^4$, —CH($R^4$)$_2$, and —C(=O)N($R^4$)$_2$;

each occurrence of $R^4$ is independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), $C_4$-$C_{10}$ heterocycle, —$C_1$-$C_3$ alkyl-($C_4$-$C_{10}$ heterocycle), $C_6$-$C_{10}$ aryl, —$C_1$-$C_3$ alkyl-($C_6$-$C_{10}$ aryl aryl), $C_5$-$C_{10}$ heteroaryl, and —$C_1$-$C_3$ alkyl-($C_5$-$C_{10}$ heteroaryl), wherein the alkyl, heteroalkyl, cycloalkyl, heterocycle, aryl and heteroaryl groups are independently optionally substituted; and x is an integer from 0-4,
or a salt or solvate thereof.

In certain embodiments, in (III) ring A is triazinoindolyl, pyrrolopyrimidinyl, phenyl, thiophenyl, furyl, pyrryl, imidazolyl, pyrazinyl, pyridinyl or pyrimidinyl.

In certain embodiments, in (III) $R^2$ is H or $C_1$-$C_6$ alkyl.

In certain embodiments, in (III) $R^3$ is selected from the group consisting of H, —S(=O)$R^4$, —S(=O)$_2R^4$, —C(=O)$R^4$, —CO$_2R^4$, and —C(=O)N($R^4$)$_2$.

In certain embodiments, the at least one compound of Formula (I) is selected from the group consisting of:

4-amino-$N^5$-{1-(4-hydroxy-3-methoxyphenyl)-2-[(3-methylbutyl)amino]-2-oxoethyl}-$N^5$-(3-hydroxypropyl)-1,2-thiazole-3,5-dicarboxamide

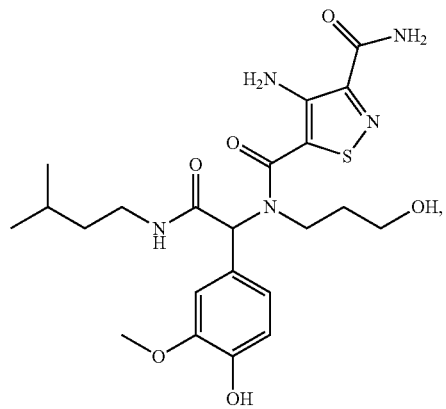 [SMILES: COc1cc(C(C(=O)NCCC(C)C)N(CCCO)C(=O)c2snc(C(N)=O)c2N)ccc1O]

N-[2-(cyclohexylamino)-1-(3,4-dihydroxyphenyl)-2-oxo-
ethyl]-N-(4-fluorophenyl)-2-({2-[(5-methyl-1,2-oxazol-
3-yl)amino]-2-oxoethyl}sulfanyl)acetamide

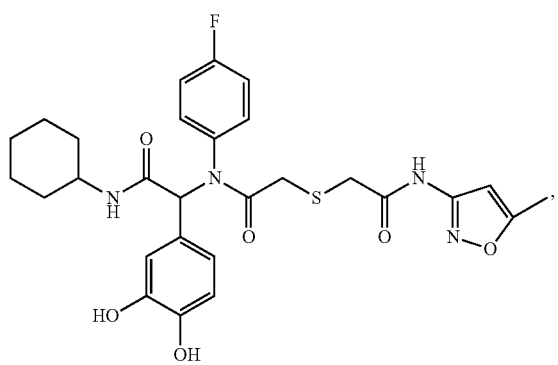 [SMILES: Cc1cc(NC(=O)CSCC(=O)N(c2ccc(F)cc2)C(C(=O)NC2CCCCC2)c2ccc(O)c(O)c2)no1]

N-[2-(cyclohexylamino)-2-oxo-1-(2-thienyl)ethyl]-2-({2-
[(5-methyl-1,2-oxazol-3-yl)amino]-2-oxoethyl}sulfanyl)-
N-(3-quinolinyl)acetamide

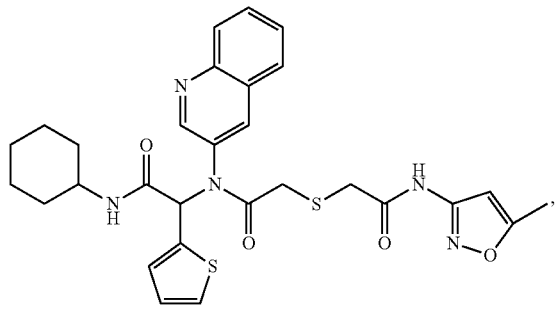 [SMILES: Cc1cc(NC(=O)CSCC(=O)N(c2cnc3ccccc3c2)C(C(=O)NC2CCCCC2)c2cccs2)no1]

4-amino-$N^5$-{2-(benzylamino)-1-[4-(dimethylamino)phe-
nyl]-2-oxoethyl}-$N^5$-(3-pyridinylmethyl)-1,2-thiazole-3,
5-dicarboxamide

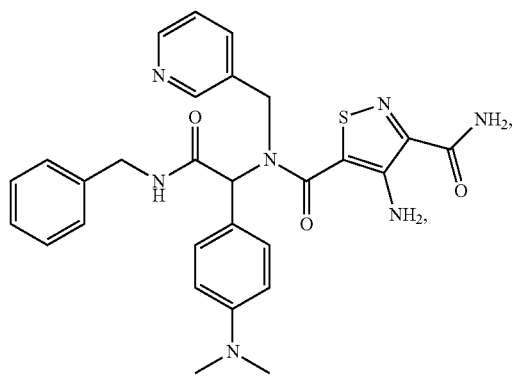 [SMILES: CN(C)c1ccc(C(C(=O)NCc2ccccc2)N(Cc2cccnc2)C(=O)c2snc(C(N)=O)c2N)cc1]

N-(2-furylmethyl)-N-{1-(4-hydroxyphenyl)-2-[(3-methyl-
butyl)amino]-2-oxoethyl}-N'-(1,3-thiazol-2-yl)succina-
mide

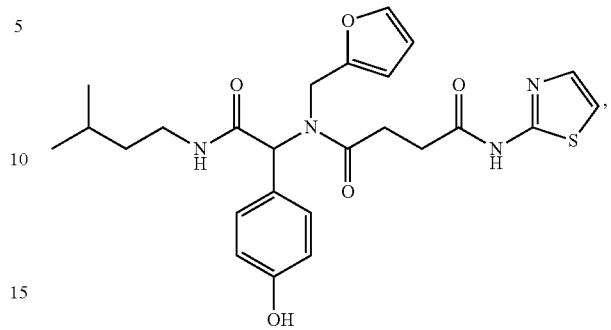

a salt thereof, a solvate thereof and any combinations thereof.

In certain embodiments, the at least one compound of Formula (II) is selected from the group consisting of:

N-[4-(cyclopropylsulfamoyl)phenyl]-2-{[5-(5,6-dimethyl-
1H-benzimidazol-2-yl)-2-pyridinyl]sulfanyl}acetamide

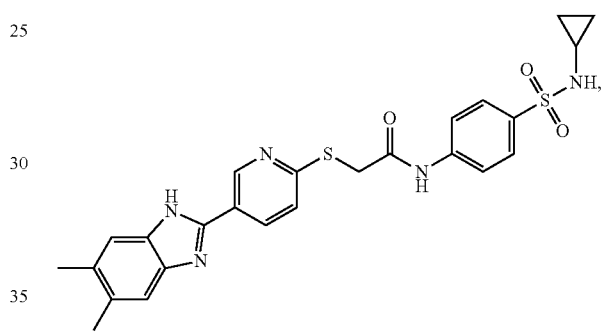

3-hydroxy-N'-({[4-(3-methoxypropyl)-5-(4-pyridinyl)-4H-
1,2,4-triazol-3-yl]sulfanyl}acetyl)benzohydrazide

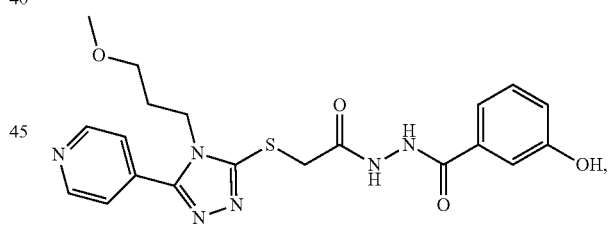

N-(4-fluorophenyl)-2-((4-(2-((3-methoxyphenyl)amino)-2-
oxoethyl)-5-(pyridin-4-yl)-4H-1,2,4-triazol-3-yl)thio)ac-
etamide

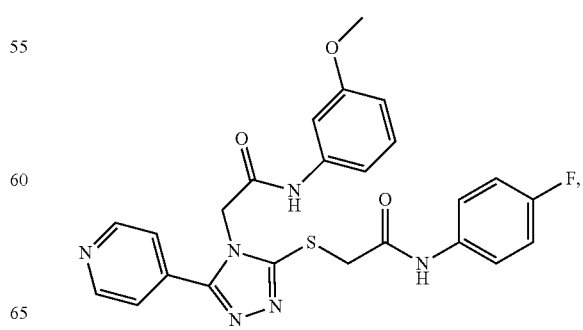

a salt thereof, a solvate thereof and any combinations thereof.

In certain embodiments, the at least one compound of Formula (III) is selected from the group consisting of:

N-[4-({2-[(8-ethyl-5H-[1,2,4]triazino[5,6-b]indol-3-yl)sulfanyl]ethyl}sulfamoyl)phenyl]acetamide

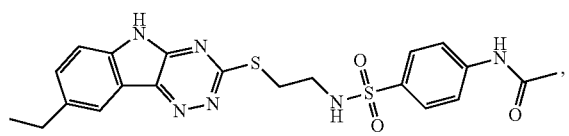 [SMILES: CCc1ccc2[nH]c3nc(SCCNS(=O)(=O)c4ccc(NC(C)=O)cc4)nnc3c2c1]

a salt thereof, a solvate thereof and any combinations thereof.

In one embodiment, the compound of the invention is selected from the group consisting of:
4-amino-$N^5$-{1-(4-hydroxy-3-methoxyphenyl)-2-[(3-methylbutyl)amino]-2-oxoethyl}-$N^5$-(3-hydroxypropyl)-1,2-thiazole-3,5-dicarboxamide,
N-[2-(cyclohexylamino)-1-(3,4-dihydroxyphenyl)-2-oxoethyl]-N-(4-fluorophenyl)-2-({2-[(5-methyl-1,2-oxazol-3-yl)amino]-2-oxoethyl}sulfanyl)acetamide,
N-[2-(cyclohexylamino)-2-oxo-1-(2-thienyl)ethyl]-2-({2-[(5-methyl-1,2-oxazol-3-yl)amino]-2-oxoethyl}sulfanyl)-N-(3-quinolinyl)acetamide,
4-amino-$N^5$-{2-(benzylamino)-1-[4-(dimethylamino)phenyl]-2-oxoethyl}-$N^5$-(3-pyridinylmethyl)-1,2-thiazole-3,5-dicarboxamide,
N-(2-furylmethyl)-N-{1-(4-hydroxyphenyl)-2-[(3-methylbutyl)amino]-2-oxoethyl}-N'-(1,3-thiazol-2-yl)succinamide,
N-[4-(Cyclopropylsulfamoyl)phenyl]-2-{[5-(5,6-dimethyl-1H-benzimidazol-2-yl)-2-pyridinyl]sulfanyl}acetamide,
3-hydroxy-N'-({[4-(3-methoxypropyl)-5-(4-pyridinyl)-4H-1,2,4-triazol-3-yl]sulfanyl}acetyl)benzohydrazide,
N-(4-fluorophenyl)-2-((4-(2-((3-methoxyphenyl)amino)-2-oxoethyl)-5-(pyridin-4-yl)-4H-1,2,4-triazol-3-yl)thio)acetamide;
N-[4-({2-[(8-ethyl-5H-[1,2,4]triazino[5,6-b]indol-3-yl)sulfanyl]ethyl}sulfamoyl)phenyl]acetamide,
a salt thereof, a solvate thereof, and any combinations thereof.

In one embodiment, the compound of the invention is not selected from the group consisting of: 4-amino-$N^5$-{1-(4-hydroxy-3-methoxyphenyl)-2-[(3-methylbutyl)amino]-2-oxoethyl}-$N^5$-(3-hydroxypropyl)-1,2-thiazole-3,5-dicarboxamide, N-[2-(cyclohexylamino)-1-(3,4-dihydroxyphenyl)-2-oxoethyl]-N-(4-fluorophenyl)-2-({2-[(5-methyl-1,2-oxazol-3-yl)amino]-2-oxoethyl}sulfanyl)acetamide, N-[2-(cyclohexylamino)-2-oxo-1-(2-thienyl)ethyl]-2-({2-[(5-methyl-1,2-oxazol-3-yl)amino]-2-oxoethyl}sulfanyl)-N-(3-quinolinyl)acetamide, 4-amino-$N^5$-{2-(benzylamino)-1-[4-(dimethylamino)phenyl]-2-oxoethyl}-$N^5$-(3-pyridinylmethyl)-1,2-thiazole-3,5-dicarboxamide, N-(2-furylmethyl)-N-{1-(4-hydroxyphenyl)-2-[(3-methylbutyl)amino]-2-oxoethyl}-N'-(1,3-thiazol-2-yl)succinamide, N-[4-(cyclopropylsulfamoyl)phenyl]-2-{[5-(5,6-dimethyl-1H-benzimidazol-2-yl)-2-pyridinyl]sulfanyl}acetamide, 3-hydroxy-N'-({[4-(3-methoxypropyl)-5-(4-pyridinyl)-4H-1,2,4-triazol-3-yl]sulfanyl}acetyl)benzohydrazide, N-(4-fluorophenyl)-2-((4-(2-((3-methoxyphenyl)amino)-2-oxoethyl)-5-(pyridin-4-yl)-4H-1,2,4-triazol-3-yl)thio)acetamide; N-[4-({2-[(8-ethyl-5H-[1,2,4]triazino[5,6-b]indol-3-yl)sulfanyl]ethyl}sulfamoyl)phenyl]acetamide, a salt thereof, a solvate thereof, and any combinations thereof.

Compositions

The invention includes a pharmaceutical composition comprising at least one pharmaceutically acceptable carrier and at least one compound of the invention. In one embodiment, the composition further comprises at least one additional therapeutic agent.

Methods

The invention includes a method of treating or preventing a brain-related disease or disorder in a patient. The method comprises administering to the patient a pharmaceutical composition comprising a therapeutically effective amount of at least one compound selected from the group consisting of:

a compound of Formula (I):

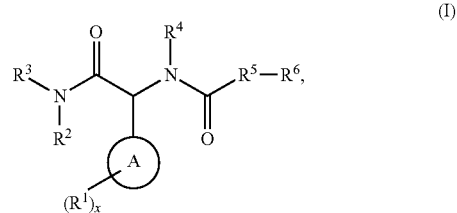

wherein in Formula (I), ring A is a monocyclic or bicyclic aryl or a monocyclic or bicyclic heteroaryl ring, and wherein the aryl or heteroaryl ring is optionally substituted with 1-4 $R^1$ groups;

each occurrence of $R^1$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —OR', —$SR^7$, —S(=O)$R^7$, —S(=O)$_2R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —OC(=O)N($R^7$)$_2$, —NHC(=O)NH($R^7$), —NHC(=O)$R^7$, —NHC(=O)O$R^7$, —C(OH)($R^7$)$_2$, and —C($NH_2$)($R^7$)$_2$;

$R^2$ is selected from the group consisting of H, $C_1$-$C_6$ alkyl, —OR', —S(=O)$R^7$, —S(=O)$_2R^7$, —C(=O)$R^7$, —$CO_2R^7$, —CH($R^7$)$_2$, and —C(=O)N($R^7$)$_2$;

$R^3$ and $R^4$ are each independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), $C_4$-$C_{10}$ heterocyclyl, —$C_1$-$C_3$ alkyl-($C_4$-$C_{10}$ heterocyclyl), $C_6$-$C_{10}$ aryl, —$C_1$-$C_3$ alkyl-($C_6$-$C_{10}$ aryl), $C_5$-$C_{10}$ heteroaryl, and —$C_1$-$C_3$ alkyl-($C_5$-$C_{10}$ heteroaryl), wherein the alkyl, heteroalkyl, cycloalkyl, heterocyclyl, aryl and heteroaryl groups are independently optionally substituted;

$R^5$ is selected from the group consisting of $C_1$-$C_6$ alkanediyl, —($CH_2$)S(=O)$_{0-2}$($CH_2$)—, $C_3$-$C_{10}$ cycloalkanediyl, $C_4$-$C_{10}$ heterocyclediyl, $C_6$-$C_{10}$ arenediyl, and $C_5$-$C_{10}$ heteroarenediyl, wherein the alkanediyl, cycloalkanediyl, heterocyclediyl, arenediyl and heteroarenediyl groups are independently optionally substituted;

$R^6$ is selected from the group consisting of H, —OR', —S(=O)$R^7$, —S(=O)$_2R^7$, —C(=O)$R^7$, —$CO_2R^7$, —CH($R^7$)$_2$, and —C(=O)N($R^7$)$_2$;

each occurrence of $R^7$ is independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), $C_4$-$C_{10}$ heterocyclyl, —$C_1$-$C_3$ alkyl-($C_4$-$C_{10}$ heterocycle), $C_6$-$C_{10}$ aryl, —$C_1$-$C_3$ alkyl-($C_6$-$C_{10}$ aryl), $C_5$-$C_{10}$ heteroaryl, and —$C_1$-$C_3$ alkyl-($C_5$-$C_{10}$ heteroaryl), wherein the alkyl, heteroalkyl, cycloalkyl, heterocycle, aryl and heteroaryl groups are independently optionally substituted; and x is an integer from 0-4;

a compound of Formula (II):

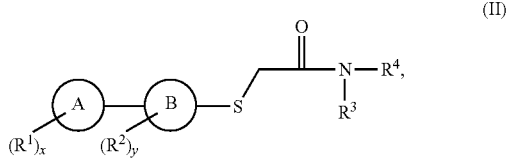

wherein in Formula (II), ring A is a monocyclic or bicyclic aryl or a monocyclic or bicyclic heteroaryl ring, and wherein the aryl or heteroaryl ring is optionally substituted with 1-4 $R^1$ groups;

ring B is a monocyclic or bicyclic arenediyl or a monocyclic or bicyclic heteroarenediyl ring, and wherein the arenediyl or heteroarenediyl ring is optionally substituted with 1-4 $R^2$ groups;

each occurrence of $R^1$ and $R^2$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —S(=O)$_2R^5$, —$(CH_2)_{0-2}$NHS(=O)$_2R^5$, —$(CH_2)_{0-2}$C(=O)$R^5$, —OC(=O)$R^5$, —$(CH_2)_{0-2}$CO$_2R^5$, —OCO$_2R^5$, —CH($R^5$)$_2$, —$(CH_2)_{0-2}$N($R^5$)$_2$, —$(CH_2)_{0-2}$C(=O)N($R^5$)$_2$, —OC(=O)N($R^5$)$_2$, —$(CH_2)_{0-2}$NHC(=O)NH($R^5$), —$(CH_2)_{0-2}$NHC(=O)$R^5$, —$(CH_2)_{0-2}$NHC(=O)O$R^5$, —C(OH)($R^5$)$_2$, and —C($NH_2$)($R^5$)$_2$;

$R^3$ is selected from the group consisting of H, $C_1$-$C_6$ alkyl, —$OR^5$, —S(=O)$R^5$, —S(=O)$_2R^5$, —C(=O)$R^5$, —CO$_2R^5$, —CH($R^5$)$_2$, and —C(=O)N($R^5$)$_2$;

$R^4$ is selected from the group consisting of —$OR^5$, —$SR^5$, —S(=O)$R^5$, —S(=O)$_2R^5$, —NHS(=O)$_2R^5$, —C(=O)$R^5$, —OC(=O)$R^5$, —CO$_2R^5$, —OCO$_2R^5$, —CH($R^5$)$_2$, —N($R^5$)$_2$, —C(=O)N($R^5$)$_2$, —OC(=O)N($R^5$)$_2$, —NHC(=O)NH($R^5$), —NHC(=O)$R^5$, —NHC(=O)O$R^5$, —C(OH)($R^5$)$_2$, —C($NH_2$)($R^5$)$_2$, $C_1$-$C_6$ alkyl, $C_3$-$C_{10}$ cycloalkyl, ($C_4$-$C_{10}$)heterocycle, ($C_6$-$C_{10}$)aryl, and ($C_5$-$C_{10}$) heteroaryl, wherein the alkyl, heteroalkyl, cycloalkyl, heterocycle, aryl and heteroaryl groups are independently optionally substituted;

each occurrence of $R^5$ is independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), ($C_4$-$C_{10}$)heterocycle, —$C_1$-$C_3$ alkyl-($C_4$-$C_{10}$ heterocycle), ($C_6$-$C_{10}$)aryl, —$C_1$-$C_3$ alkyl-($C_6$-$C_{10}$ aryl), ($C_5$-$C_{10}$)heteroaryl, and —$C_1$-$C_3$ alkyl-($C_5$-$C_{10}$ heteroaryl), wherein the alkyl, heteroalkyl, cycloalkyl, heterocycle, aryl and heteroaryl groups are independently optionally substituted; and x and y are independently an integer from 0-4;

a compound of Formula (III):

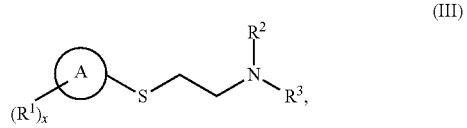

wherein in Formula (III), ring A is a monocyclic, bicyclic or tricyclic aryl or a monocyclic, bicyclic or tricyclic heteroaryl ring, and wherein the aryl or heteroaryl ring is optionally substituted with 1-4 $R^1$ groups;

each occurrence of $R^1$ is independently selected from the group consisting of —$C_1$-$C_6$ alkyl, —$C_1$-$C_6$ fluoroalkyl, —$C_1$-$C_6$ heteroalkyl, F, Cl, Br, I, —CN, —$NO_2$, —$OR^4$, —$SR^4$, —S(=O)$R^4$, —S(=O)$_2R^4$, —NHS(=O)$_2R^4$, —C(=O)$R^4$, —OC(=O)$R^4$, —CO$_2R^4$, —OCO$_2R^4$, —CH($R^4$)$_2$, —N($R^4$)$_2$, —C(=O)N($R^4$)$_2$, —OC(=O)N($R^4$)$_2$, —NHC(=O)NH($R^4$), —NHC(=O)$R^4$, —NHC(=O)O$R^4$, —C(OH)($R^4$)$_2$, and —C($NH_2$)($R^4$)$_2$;

$R^2$ and $R^3$ are each independently selected from the group consisting of H, $C_1$-$C_6$ alkyl, —$OR^4$, —S(=O)$R^4$, —S(=O)$_2R^4$, —C(=O)$R^4$, —CO$_2R^4$, —CH($R^4$)$_2$, and —C(=O)N($R^4$)$_2$;

each occurrence of $R^4$ is independently selected from the group consisting of H, $C_1$-$C_6$ alkyl, $C_1$-$C_6$ heteroalkyl, $C_3$-$C_{10}$ cycloalkyl, —$C_1$-$C_3$ alkyl-($C_3$-$C_6$ cycloalkyl), $C_4$-$C_{10}$ heterocycle, —$C_1$-$C_3$ alkyl-($C_4$-$C_{10}$ heterocycle), $C_6$-$C_{10}$ aryl, —$C_1$-$C_3$ alkyl-($C_6$-$C_{10}$ aryl), $C_5$-$C_{10}$ heteroaryl, and —$C_1$-$C_3$ alkyl-($C_5$-$C_{10}$ heteroaryl), wherein the alkyl, heteroalkyl, cycloalkyl, heterocycle, aryl and heteroaryl groups are independently optionally substituted; and x is an integer from 0-4;

a salt or solvate thereof, or any mixtures thereof.

In one embodiment, the compound of the invention is selected from the group consisting of: 4-amino-$N^5$-{1-(4-hydroxy-3-methoxyphenyl)-2-[(3-methylbutyl)amino]-2-oxoethyl}-$N^5$-(3-hydroxypropyl)-1,2-thiazole-3,5-dicarboxamide, N-[2-(cyclohexylamino)-1-(3,4-dihydroxyphenyl)-2-oxoethyl]-N-(4-fluorophenyl)-2-({2-[(5-methyl-1,2-oxazol-3-yl)amino]-2-oxoethyl}sulfanyl)acetamide, N-[2-(cyclohexylamino)-2-oxo-1-(2-thienyl)ethyl]-2-({2-[(5-methyl-1,2-oxazol-3-yl)amino]-2-oxoethyl}sulfanyl)-N-(3-quinolinyl)acetamide, 4-amino-$N^5$-{2-(benzylamino)-1-[4-(dimethylamino)phenyl]-2-oxoethyl}-$N^5$-(3-pyridinylmethyl)-1,2-thiazole-3,5-dicarboxamide, N-(2-furylmethyl)-N-{1-(4-hydroxyphenyl)-2-[(3-methylbutyl)amino]-2-oxoethyl}-N'-(1,3-thiazol-2-yl)succinamide, N-[4-(Cyclopropylsulfamoyl)phenyl]-2-{[5-(5,6-dimethyl-1H-benzimidazol-2-yl)-2-pyridinyl]sulfanyl}acetamide, 3-hydroxy-N'-({[4-(3-methoxypropyl)-5-(4-pyridinyl)-4H-1,2,4-triazol-3-yl]sulfanyl}acetyl)benzohydrazide, N-(4-fluorophenyl)-2-((4-(2-((3-methoxyphenyl)amino)-2-oxoethyl)-5-(pyridin-4-yl)-4H-1,2,4-triazol-3-yl)thio) acetamide; N-[4-({2-[(8-ethyl-5H-[1,2,4]triazino[5,6-b]indol-3-yl]sulfanyl]ethyl}sulfamoyl)phenyl]acetamide, a salt thereof, a solvate thereof, and any combinations thereof.

In one embodiment, the brain-related disease or disorder is at least one selected from the group consisting of attention deficit hyperactivity disorder (ADHD), schizophrenia, drug addiction, smoking addiction, eating disorders, obsessive-compulsive disorder, depression, an anxiety disorder, an affective disorder, traumatic brain injury, stroke, cognitive disorders and narcolepsy.

In one embodiment, the composition further comprises at least one additional therapeutic agent. In another embodiment, the pharmaceutical composition is co-administered to the patient with a second pharmaceutical composition comprising at least one additional therapeutic agent. In yet another embodiment, the pharmaceutical composition is administered to the patient a given period of time before or after a second pharmaceutical composition comprising at least one additional therapeutic agent is administered to the patient. In yet another embodiment, the patient is human.

The invention further includes a method of modulating the activity of a monoamine transporter. The method comprises contacting the monoamine transporter with an effective amount of at least one compound of the invention, whereby the activity of the monoamine transporter is modulated.

The invention further includes a method of inducing a conformational change in a monoamine transporter. The method comprises contacting the monoamine transporter with an effective amount of at least one compound of the invention, whereby a conformational change is induced in the monoamine transporter.

In one embodiment, the monoamine transporter is selected from the group consisting of a serotonin transporter, a norepinephrine transporter, a dopamine transporter, and any combinations thereof.

Combination Therapies

In one non-limiting embodiment, the compounds of the present invention are useful in the methods of present invention in combination with one or more additional compounds useful for treating a brain-related disease or disorder. These additional compounds may comprise compounds of the present invention or other compounds, e.g., commercially available compounds, known to treat, prevent, or reduce the symptoms of a brain-related disease or disorder.

In non-limiting examples, the compounds of the invention may be used in combination with one or more of the following psychostimulant agents: amphetamine, dextroamphetamine, methamphetamine and other phenylisopropylamine derivatives, cocaine, ecstacy, phencyclidine, phenmetratzine, methylphenidate, diethylpropion, pemoline, mazindol, (−)-cathione, a salt thereof and mixtures thereof.

In non-limiting examples, the compounds of the invention may be used in combination with one or more of the following antidepressants: tranylcypromine, fluoxetine, sertraline, bupropion, fluvoxamine, paroxetine, desipramine, nortriptyline, venlafaxine, phenelzine, amisulpride, moclobemide, protriptyline, amoxapine, maprotiline, isocarboxazid, dibenzepin, tianeptine, mabanazine, nialamide, pirlindole, safrazine, toloxatone, amineptine, medifoxamine, oxitriptan, rolipram, tofenacin, viloxazine (Vivalan®), a salt thereof and mixtures thereof.

A synergistic effect may be calculated, for example, using suitable methods such as, for example, the Sigmoid-$E_{max}$ equation (Holford and Scheiner, 19981, Clin. Pharmacokinet. 6: 429-453), the equation of Loewe additivity (Loewe and Muischnek, 1926, Arch. Exp. Pathol Pharmacol. 114: 313-326) and the median-effect equation (Chou and Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a brain-related disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a brain-related disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a brain-related disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a brain-related disease or disorder in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating a brain-related disease or disorder) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a brain-related disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a brain-related disease or disorder. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention will depend on the age, sex and weight of the patient, the current medical condition of the patient and the progression of the brain-related disease or disorder in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.
Materials and Methods

[$^3$H]-serotonin and [$^3$H]-dopamine were obtained from PerkinElmer (Waltham, Mass., USA). Reagents for buffers, inhibitors, and other chemicals were purchased from Sigma-RBI (St. Louis, Mo., USA). Cell culture media, fetal bovine serum (FBS), penicillin/streptomycin, and Dulbecco phosphate-buffered saline (D-PBS) were purchased from Life Technologies (Carlsbad, Calif., USA).

Mutagenesis

All single-amino-acid mutants were generated using the polymerase chain reaction-based site-directed mutagenesis QuikChange (Stratagene, La Jolla, Calif., USA) method. The templates were full-length and nontagged human SERT in pcdna3.1 under the control of the mammalian cytomegalovirus promoter. Chimeras were produced with a modified version of the QuikChange mutagenesis protocol employing the megaprimer strategy using previously developed methods (Kirsch and Joly, 1998, Nucleic Acids Res 26:1848-1850). This strategy enabled the production of chimeras in a sequence-independent manner. All clones were verified by sequencing to contain only the expected mutation.
Transport Assays COS-7, HEK293, and MDCK cells were maintained in Dulbecco modified Eagle medium (3.5 g/l glucose) supplemented with FBS (10% each) at 37° C. with 5% $CO_2$. Uptake experiments were performed 2 days after transfecting DNAs (hSERT, human dopamine transporter [hDAT], chimeras or mutants, or empty vector for background) with TransIT-LT1 (Minis Bio LLC, Madison, Wis., USA) transfection reagent and plating the cells in 24- or 96-well plates. The media was removed and the cells were washed with PBS (137 mM NaCl, 2.7 mM KCl, 4.3 mM $Na_2HPO_4$, 1.4 mM $KH_2PO_4$, pH 7.4) containing 0.1 mM $CaCl_2$, 1 mM $MgCl_2$, 10 µM clorgyline, 10 µM pargyline, 5 µM RO 41-0960, and 100 µM ascorbic acid (PBS-CM). Following washing, cells were preincubated at room temperature for 10 min in PBS-CM containing vehicle or various concentrations of experimental drugs (ATM7, 5HT, amphetamine, or MDMA, as indicated elsewhere herein).

Following preincubation of the cells, uptake was initiated by the addition of [$^3$H]-serotonin to a final concentration of 25 nM, for the serotonin transport assays. For dopamine assays, [$^3$H]-dopamine was added to the 25 nM final concentration. The uptake was allowed to continue for 10 min at room temperature and was terminated by washing with PBS-CM. Cells were solubilized in scintillation cocktail and counted on a Wallac 1450 MicroBeta liquid scintillation counter (both from PerkinElmer). To determine uptake kinetics, various concentrations of [$^3$H]-serotonin were assayed as described above. Assuming Michaelis-Menten kinetics, the data was analyzed using nonlinear regression using GraphPad Prism, version 5.03 for Windows (GraphPad Software, La Jolla, Calif., USA). $V_{max}$ and $K_M$ are given as mean±S.D. of three independent experiments. For determination of $EC_{50}$ values for experimental drugs and other compounds, the concentration curves generated were fitted to a Hill equation by nonlinear regression analysis using GraphPad Prism version 5.03 for Windows. $EC_{50}$ values are given as mean±S.E.M. of at least five independent experiments. Statistical significance between vehicle and drug treatments was assessed using Student t-test or one-way analysis of variance (ANOVA) Dunnett's multiple-comparison test ($p<0.05$).
Efflux Experiment in COS-7 Cells COS-7 cells were maintained under the same conditions as above. Efflux experiments were performed 2 days after cell transfection with hSERT or empty vector and plating of the cells in 24-well plates. Cells were washed with room temperature PBS-CM and then loaded with 50 nM [$^3$H]-serotonin for 1 h. After preloading, cells were washed twice with buffer and then incubated for 10 min with or without substrates at room temperature. After incubation, the supernatant was collected, liquid scintillation fluid added, and the samples counted (Beckman LS-6500 Multi-purpose Scintillation Counter; Beckman Coulter, Brea, Calif.). The cells were solubilized in a solution of 0.1% sodium dodecyl sulfate and 0.1 M NaOH; liquid scintillation fluid was added and tubes were counted as above. All assays were done in quadruplicate.

The percentage of [$^3$H]-serotonin efflux among different treatments was calculated by adding counts of supernatant plus cell lysis, with the supernatant counts then divided by the total and multiplied by 100 to yield the percentage of efflux. For determination of $EC_{50}$ values for experimental drugs and other compounds, the concentration curves generated were fitted to a Hill equation by nonlinear regression analysis using GraphPad Prism version 5.03 for Windows. $EC_{50}$ values are given as mean±S.E.M. of at least five independent experiments. Statistical significance between vehicle and drug treatments was assessed using one-way ANOVA Dunnett's multiple-comparison test ($p<0.05$).

MTSET Labeling Assays

COS-7 cells were transfected as described with hSERT C109A/Q332C mutant and assayed 2 days later for [2-(trimethylammonium)ethyl]methane-thiosulfonate (MTSET) sensitivity. Cells were washed with PBS-CM and incubated with substrate (5HT) or ligand (ATM7 or cocaine) in PBS-CM for 10 min at room temperature. MTSET 0.5 mM was added from a stock solution prepared in dimethyl sulfoxide. After a 10-min incubation, the cells were washed five times in PBS-CM and assayed for uptake with 50 nm [$^3$H]-serotonin for 10 min at room temperature as described elsewhere herein. Uptake was terminated by washing twice with PBS-CM.

Virtual Screen

Modeling the hSERT:

The human serotonin transporter was modeled using LeuT bound to the tricyclic antidepressant desipramine as a template in the homology modeling program Modeler (ver 9.1) (Sali et al., 1995, Proteins 23:318-326). The amino acid sequence of hSERT was obtained from Swiss-Prot database with sequence id P31645 and was aligned to the LeuT sequence derived from the crystal structure listed in Protein Databank under the pdb code 2QJU (Singh et al., 2007, Nature 448:952-956). Ten structures of SERT were modeled, among which one low-energy structure was subjected to further refinement using energy minimization and constrained MD simulation using NAMD2 (Phillips et al., 2005, J Comput Chem 26:1781-1802). All simulations were performed using Amber force field and Amber charges (Cornell et al., 1995, J Am Chem Soc 117:5179-5197).

The resulting structure was further immersed in POPC (palmitoyloleoylphosphocholine) membrane patch simulated using the Desmond membrane module of the Schrödinger suite (Bowers et al., 2006, J Chem Phys 124: 184109). An orthorhombic model membrane consisting of 103 POPC molecules and 5680 solvent molecules and 4 chloride ions to neutralize the charge was simulated. Optimal positioning of the membrane was computed using the LeuT structure in the OPM database (Orientations of Proteins in Membranes; the PPM server) (Lomize et al., 2012, Nucleic Acids Res 40:D370-D376). This database consists of a compendium of membrane protein structures whose spatial arrangements in lipid bilayers have been precomputed in order to facilitate simulation of proteins in membrane complexes. The membrane-bound hSERT structure was refined using MD simulation using the Desmond program (D.E. Shaw Research, New York, N.Y.), with a production run of 3 ns. The results were analyzed using the VMD (Visual Molecular Dynamics) trajectory analysis module (Humphrey et al., 1996, J Mol Graph 14:33-38, 27-28) to derive the nature and composition of molecular interactions of residues at the allosteric site of hSERT with membrane.

Virtual Screening:

A four-point pharmacophore consisting of residues D328, E494, K490, and Y568 was developed based on their interaction profile in the membrane-bound MD simulation. An electronic database of 3 million small molecules was screened using the HSB method with a four-point pharmacophore as input. A total of 605 hit molecules that resulted from the screening were subjected to a variety of filtering schemes for drug-like properties, the human ether-à-go-go related gene, pregnane X receptor binding, and ability to pass through the blood-brain barrier. The resulting 462 molecules were docked to the binding site consisting of residues D328, Q332, R564, K490, E493, F564, etc., using the docking program GOLD ver 4.0 (Jones et al., 1995, J Mol Biol 245:43-53).

The docked complexes were scored using Goldscore, Chemscore, and a customized scoring function (Jones et al., 1995, J Mol Biol 245:43-53; Eldridge et al., 1997, J Comput Aided Mol Des 11:425-445; Kortagere and Welsh, 2006, J Comput Aided Mol Des 20:789-802; Kortagere et al., 2009, Pharm Res 26:1001-1011). The customized scoring scheme was developed using the contact maps of the ligand atoms with that of the binding site residues. This biased scoring scheme included penalizing ligands that matched the chemical profile of psychostimulants and known inhibitors of SERT. Further, the complexes were ranked using a consensus scoring scheme as adopted in the HSB method. Finally, the 10 best ranking compounds were tested for their ability to interfere with the uptake and amphetamine-induced efflux of serotonin and dopamine at their respective transporters.

Example 1

Extracellular Domains Located Outside the Substrate Permeation Pathway are Central for SERT Function and Substrate Interaction To investigate the role of central domains formed by TMD1 and 6 within SERT, chimeras were produced between the human and parasite SERT and TMD1 and 2 or 6 and 7, respectively, were replaced in the human SERT with their parasite counterparts. In this initial screen, amphetamine-elicited efflux was used to determine changes in the interaction of SERT with exogenous substrates. SERT-mediated efflux assays are well established and recognized as a valid method for determining whether a molecule is a substrate of SERT, because efflux of previously loaded intracellular serotonin is triggered only by substrates and not by inhibitors.

Unexpectedly, it was observed that replacing any of these central TMDs had no obvious effect on the interaction between human SERT and amphetamine (FIG. 1). By employing chimeras between human and parasite SERT, the search was expanded to structures outside the above-defined translocation pathway. Exchanging extracellular loops, conversely, had an effect on amphetamine-elicited efflux. For example, the replacement of EL3 (hSERT amino acids 292-342) of human SERT with the parasite EL3 produced a chimeric transporter that displayed no significant amphetamine-elicited efflux (FIG. 1). This result led to the hypothesis that changes in extracellular loops could cause subtle allosteric changes in the arrangement of TMDs, and these allosteric changes would alter the interaction of the TMDs with substrates, each other, and the plasma membrane lipid environment.

To examine this hypothesis, structural models were employed to identify amino acids that were located in such interfaces and that could be affected by modifications to EL3. The domain at the C-terminal part of EL3 formed by EL1, EL3, and the outer parts of TMD1 and 6 were of particular interest. Several amino acids in TMD1 and 6 that were predicted by the transporter models to interact with each other were mutated. Mutations of human SERT amino acid 112 (TMD1), and 328 (TMD6) resulted in transporters that responded to 1 μM amphetamine, with no significant amphetamine-elicited efflux. This is in contrast to the substantial efflux elicited by the same concentration of amphetamine by the wild-type human SERT. Inhibition assays indicated that the mutations significantly decreased the affinity of SERT for amphetamine (Table 1). The $IC_{50}$ values for SERT, N112C, and D328C were 13.9±0.8, 29.8±2.0, and 54.8±5.8 μM, respectively.

TABLE 1

Dose response inhibition assay of hSERT mutants

| | $IC_{50}$/μM |
|---|---|
| SERT | 13.9 ± 0.8 |
| N112C | 29.8 ± 2.0* |
| D328C | 54.8 ± 5.8*** |

Mutated versions of human SERT were assayed for transport inhibition by amphetamine. (*p < 0.05 and ***p < 0.0001 One way ANOVA followed by Bonferroni's Multiple comparison test)

Example 2

Identification of Binding Pocket by Modeling and Virtual Screening

Figure 2:
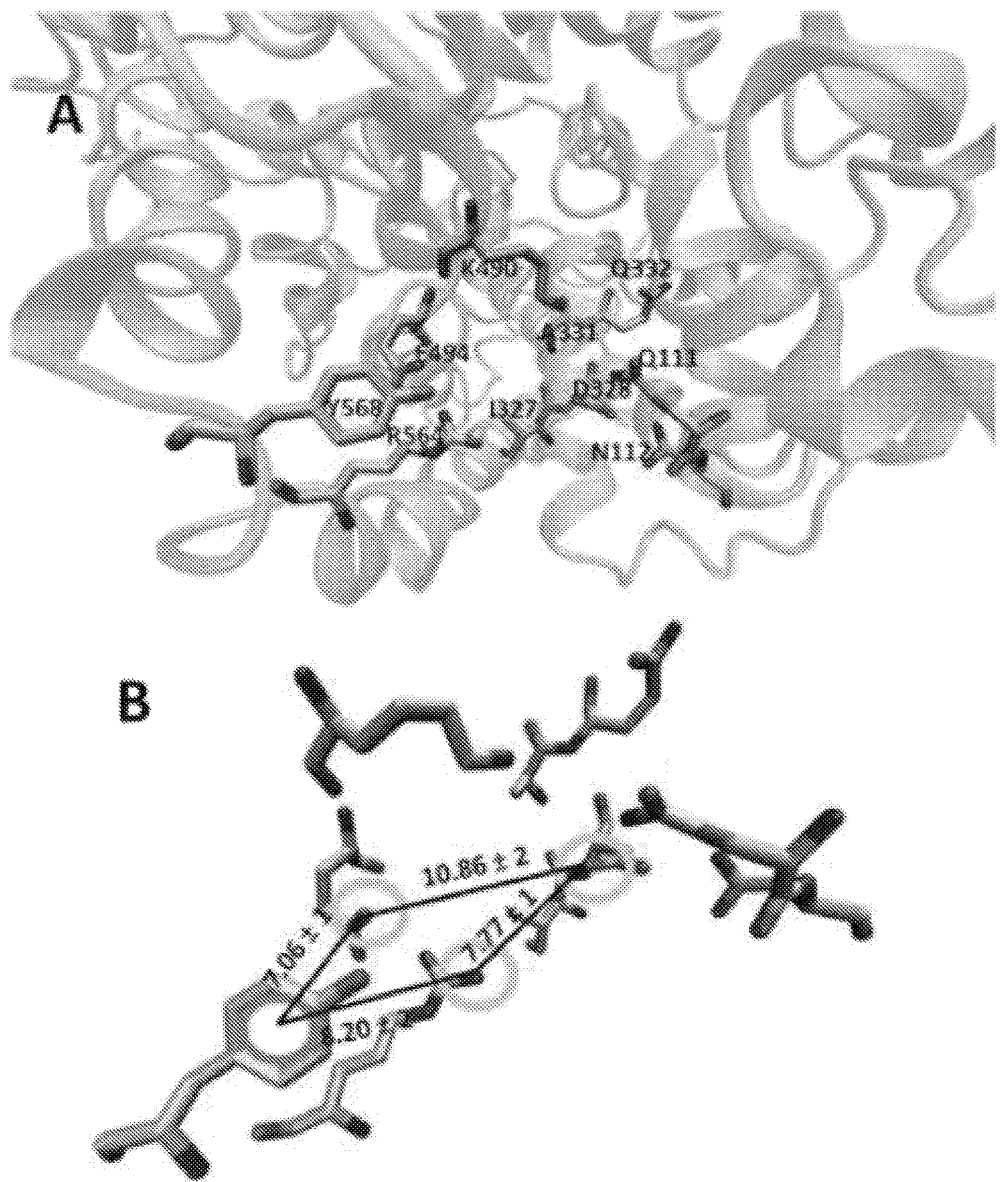
FIG. 2, comprising

The outward-facing conformation of the bacterial transporter LeuT provided an ideal target to model the outward-facing conformation of hSERT in order to understand the role of the above-identified allosteric site that is formed by the extracellular loops and that apparently modulates the functional features of hSERT. Based on the mutational analysis described above and on a structural model derived from MD simulations of hSERT in complex with membrane patches, a potential allosteric pocket was identified. This pocket is lined by residues Q111, N112, I327, D328, A331, Q332, K490, E494, and R564 (FIG. 2A). These residues form a network of hydrogen-bonded interactions with residues from EL6 that interact with the head groups of the membrane to stabilize a conformation suitable for allosteric modulation.

The residue composition of the binding pocket includes a combination of hydrophobic and polar residues that could be efficiently utilized for the screening of small-molecule modulators using the HSB method. A four-point pharmacophore was designed by combining three hydrogen bond donor/acceptor pairs with a hydrophobic/aromatic group (FIG. 2B). A small-molecule library of 3 million compounds screened using this hybrid pharmacophore resulted in the identification of 464 molecules that were further docked into the allosteric binding pocket. The docked complexes were scored using Goldscore, Chemscore, and a customized scoring scheme that was developed based on the nature of interactions of the ligand at the binding pocket. The 10 best-ranking compounds were tested in in vitro assays for their effect on uptake and efflux.

Example 3

ATM7 Enhances Serotonin Uptake

ATM7 was examined in more detail to understand its mechanism of action. In a dose-response assay, it was observed that ATM7 activated serotonin uptake very potently at nanomolar concentrations. A similar assay with the related dopamine transporter showed a similar stimulation of uptake activity, but at higher concentrations of ATM7. ATM7 displayed a bell-shaped response as ATM7 at micromolar concentrations inhibited both SERT and DAT (FIG. 3A). Performing serotonin uptake at different concentrations of serotonin, it was observed that the stimulatory effects of ATM7 were observed only at lower nanomolar concentrations (FIG. 3B); at higher concentrations there were no significant differences and ATM7 did not affect $V_{max}$. Although not wishing to be bound by any particular theory, this finding suggests a complex mechanism of action of ATM7 on SERT function and points to conformation-specific and allosteric effects.

Example 4

MDMA-Elicited Efflux is Affected by ATM7 hSERT efflux assays were initially employed to isolate the mutations that identified the binding pocket of ATM7. ATM7 could therefore be expected to have an effect on this particular activity of hSERT. To test this possibility, the effect of ATM7 on MDMA-elicited efflux assay on the wild-type human SERT and on a mutant (112C) that forms part of the predicted ATM7 binding pocket was examined. At 1 μM, ATM7 enhanced MDMA-elicited efflux in the wild-type SERT (FIG. 4A). The affinity for MDMA was not affected by ATM7, but the efficacy of eliciting release of intracellular serotonin was significantly enhanced (510%±17% in the presence of ATM7 versus 380%±10% in vehicle treated). At the same concentration, ATM7 had no effect on MDMA-elicited efflux in the 112C mutant (375%±45% in the presence of ATM7 versus 365%±40% in vehicle treated).

The effect of ATM7 on an activity defined as basal/leak efflux was examined. In the transfected COS-7 cells used in this study, the loaded serotonin was not packaged into vesicles and thus remained accessible to SERT in the cytosol and was therefore prone to random leak out of the cell through the SERT. Measuring the release of preloaded serotonin in the absence of extracellular substrate, ATM7 dose-dependently inhibited this basal/leak efflux (IC50=0.63±0.31 nM). The 112C mutant was less sensitive to ATM7 treatment and required higher concentrations of ATM7 to achieve an effect comparable to that seen with the wild-type ($IC_{50}$=37±25 nM) (FIG. 4B). This lower affinity of the 112C mutants supports the hypothesis that ATM7 mediates its effect by binding within the novel pocket identified in this study.

Example 5

ATM7 Stabilizes an Outward-Facing Confirmation of hSERT

Although not wishing to be bound by any particular theory, when taken together, the above results suggest a mechanism of action of ATM7 that stabilizes hSERT in an outward-facing conformation, enhancing initial substrate interaction and resulting in increased serotonin uptake and MDMA-elicited efflux. This hypothesis would also explain the inhibition caused by ATM7 on basal efflux as ATM7 would decrease the levels of intracellular serotonin exiting the cells by reducing the fraction of inward-facing hSERT molecules that are necessary for the basal efflux. To test this hypothesis, a mutant was of hSERT was examined, wherein the mutation monitors the conformational states of hSERT. In this mutant (Q332C), the susceptibility of the mutant transporter towards the thiol-modifying reagent MTSET was dependent on preincubation with substrate and inhibitor. A substrate such as serotonin would prevent modification, and an inhibitor such as cocaine would enhance the modification. In one embodiment, the enhanced modification by cocaine would signify that an outward conformation had been stabilized.

Figure 5:
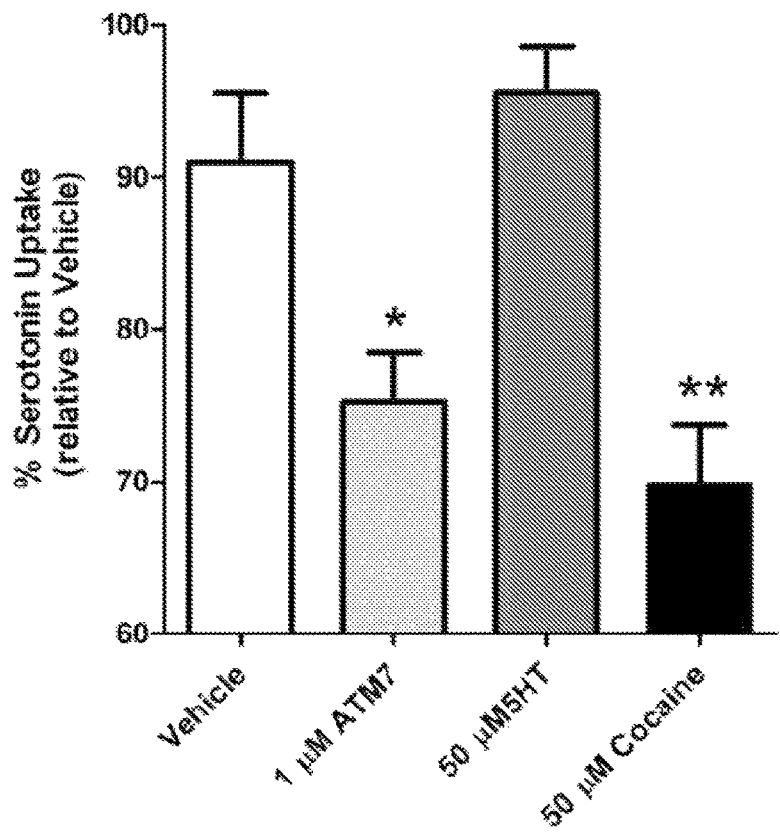
FIG. 5 illustrates the finding that ATM7 (KM-986) stabilizes outward-facing conformation. A conformationally MTSET-sensitive mutant of hSERT, Q332C, was used to test whether ATM7 affects hSERT conformations. Cells expressing the Q332C mutant were incubated with MTSET in the presence of various compounds (ATM7, serotonin (5HT), and cocaine). After washing, the remaining uptake activity was measured and compared with control (*$p<0.05$ and ** $p<0.01$, one-way ANOVA with Dunnett's multiple-comparison test, comparing vehicle and drug treatments).

The effect of ATM7 was compared with the effects of serotonin and cocaine on the reactivity of the Q332 mutant and ATM7 behaved more like cocaine than serotonin (FIG. 5B). This finding supports the hypothesis that ATM7 stabilizes hSERT in an outward-facing conformation, but through a different mechanism than cocaine, and that ATM7 does not inhibit transport activity.

Example 6

ATM7—a Novel Allosteric Modulator of hSERT Function

Described herein is the discovery of a novel allosteric modulator of hSERT function. It was observed that the interactions with exogenous compounds, including the substrates amphetamine and MDMA but also inhibitors such as cocaine and antidepressants, displayed lowered affinity in the parasite SERT. Although not wishing to be bound by any particular theory, these results suggest that the interaction of hSERT with exogenous molecules can be separated from its interaction with serotonin, and therefore could be modulated without affecting the core serotonin uptake process.

A search was conducted to identify structural determinants of these pharmacological differences. Unexpectedly, it was observed that exchanging the EL3 loop of hSERT with the corresponding parasite SERT loop had a significant effect on SERT function and on its interactions with exogenous substrates such as amphetamine. The results further demonstrated the importance of amino acids 112 and 328 within this extracellular pocket. Although not wishing to be bound by any particular theory, it is possible that these mutations cause subtle rearrangements of the SERT molecule that affect more central regions of the transporter where the direct interaction between amphetamine and SERT occurs. Because the domain formed by amino acids 112 and 328 is located well outside the core translocation pathway of hSERT, this domain could be a target for allosteric modulators of hSERT function.

Dynamic modeling based on the LeuT structure bound to a tricyclic antidepressant as a template was performed to produce a homology model of hSERT. The hSERT model was embedded in a model membrane patch and further refined using MD simulations and the trajectories analyzed for allosteric pockets. One such pocket was formed by residues found in structure-function studies (N112, D328) and also by Q332, K490, E494, and R564, among others. Although not wishing to be bound by any particular theory, MD simulations suggest that these residues could stabilize an allosteric conformation of the transporter via a network of hydrogen-bonded interactions with other residues of EL6 and the membrane head groups. Some of these residues have been implicated in functional aspects of other transporters within the SLC6 neurotransmitter transporter family. Observations from these structural studies support the hypothesis that targeting the allosteric site with small-molecule modulators could stabilize the transporter in a conformational state conducive to allosteric modulation.

Figure 6:
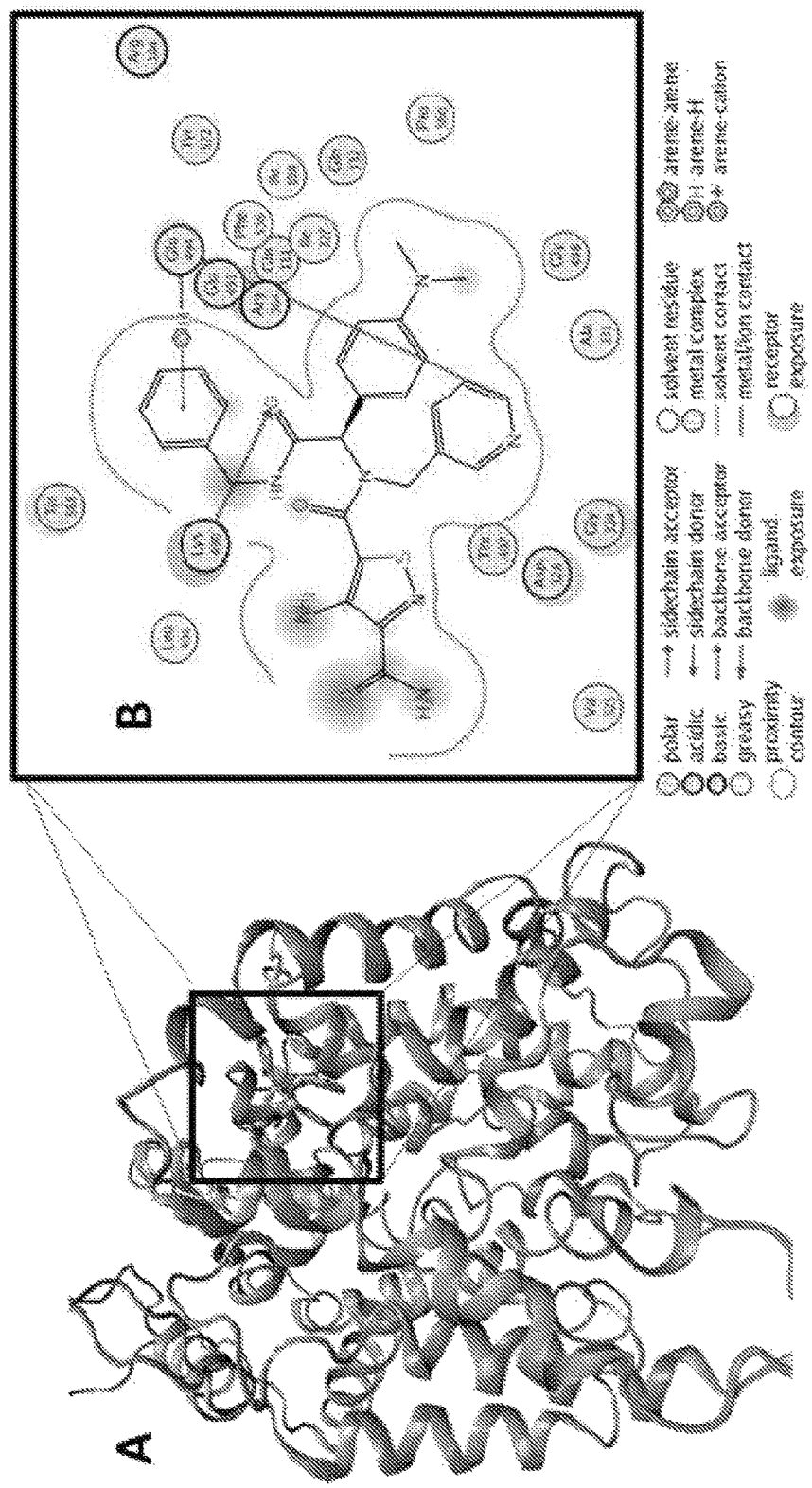
FIG. 6, comprising

To test this hypothesis, a four-point pharmacophore was designed using the residues lining the allosteric site and an in silico screen was performed using the HSB method. The 10 best-ranking compounds with distinct chemical cores that energetically stabilized this conformation of hSERT were selected. Among these compounds, ATM7 very potently at low nanomolar concentrations enhanced hSERT serotonin uptake activity. The binding mode of ATM7 is favored by hydrogen-bonded interactions with D328, E494, R564, and K490. In addition, the molecule has aromatic interactions with Y568 and cation-pi interactions with E494. Other hydrophobic interactions, such as with A331, F556, L491, I327, and P560, further stabilize the binding of ATM7 in the allosteric site (FIG. 6).

In one embodiment, the mechanism of action of ATM7 is through an allosteric interaction with a specific outward-facing conformation, and that this conformation is favored or stabilized by ATM7. The results of the experiments support this hypothesis. Although not wishing to be bound by any particular theory, it is possible that if an outward-facing conformation were stabilized by ATM7, it would cause fewer inward-facing conformations to be available to mediate the leak efflux of intracellular serotonin (FIG. 4B). Conversely, when an extracellular substrate, such as MDMA, is available on the outside ATM7, by stabilizing the outward-facing conformation, it facilitates the interaction of MDMA with hSERT, resulting in enhanced MDMA-elicited efflux (FIG. 4A). ATM7 enhanced serotonin uptake only at low concentrations of serotonin, and although not wishing to be bound by any particular theory, this result suggests that this effect also is caused by stabilization of the outward-facing conformation enhancing the access of serotonin to the transport-ready conformation (FIG. 3B). This finding also suggests that at low levels of serotonin, the rate-limiting step for the uptake process is the encounter of extracellular serotonin with the outward-facing conformation of hSERT. At low levels of serotonin, the probability for this interaction is low. These results support the hypothesis that ATM7 increases the probability of interactions between the small number of serotonin molecules and hSERT by retaining more hSERT molecules in the outward-facing conformation. At higher serotonin concentrations, the number of outward-facing hSERT molecules is no longer rate limiting, as outward-facing hSERT molecules can readily encounter serotonin molecules.

The MTSET experiments employing the conformation-sensitive Q332C mutant also support the hypothesis that ATM7 favors an outward-facing conformation. ATM7, similarly to cocaine, makes the transporter more sensitive to MTSET, but importantly this is through a mechanism different from cocaine, as ATM7 does not inhibit and lock the transporter in this outward-facing conformation but more likely stabilizes it. Q332 resides within the allosteric domain where ATM7 binds, further pointing to this importance of this region of the transporter for conformational transitions and going through significant movements during the translocation cycle. Q332 participates in a network of hydrogen-bonded interactions with main-chain and side-chain atoms connecting TMD1 and TMD6, thus providing a structural anchor to the outward-facing conformation of the transporter.

The results disclosed herein demonstrate that ATM7 represents a new class of potential psychotropic drugs because it establishes a novel allosteric mechanism for affecting hSERT activity and thereby serotonin signaling in the human brain. hSERT is centrally involved in the termination and the regulation of serotonin signaling, and therefore compounds that modify hSERT activity could have clinical interest. The mechanism by which SSRIs alleviate depression and anxiety is not clear. Extracellular serotonin levels rapidly increase with SSRI treatment, but symptoms take weeks to disappear. Although not wishing to be bound by any particular theory, it is likely that delayed neurochemical adaptations take place and that a new balance must be established within the neuronal networks controlling mood and levels of anxiety. SSRIs achieve this through an unknown mechanism that is triggered by the tuning of serotonin levels. It was hypothesized that lowering extracellular serotonin levels (the opposite of what SSRIs accomplish), also through unknown mechanisms, establishes a new, beneficial homeostatic balance among the neurotransmitter systems controlling mood and anxiety levels. ATM7 enhances serotonin uptake only at serotonin concentrations in the low nanomolar range, but this concentration is sufficient to activate serotonin receptors, which often have affinities for serotonin at about 1 nM. In one embodiment, molecules with activities like ATM7 might have clinical relevance in the treatment of depression or anxiety.

In addition to direct effects on serotonin reuptake, ATM7 has effects on the interaction of amphetamine-like molecules with hSERT. Pursuing the effects of ATM7 in animal models of amphetamine-mediated behaviors may be useful in order to determine whether ATM7 or molecules with similar activities have potential in treating amphetamine abuse or attention deficit-hyperactivity disorder.

Example 7

Exploration of Novel Allosteric Pockets on SERT, NET, and DAT

In one embodiment, the difference in interactions with psychostimulants and antidepressants between the parasite SERT and DAT compared with their mammalian counterparts suggests that the conformational changes induced during binding of endogenous substrates are similar in both parasite and human isoforms but are significantly different for the binding of other exogenous transporter ligands (Table 2). Based on these results, it was hypothesized that hSERT, hNET, and hDAT may be guided into conformations similar to that of SmSERT and SmDAT using allosteric modulators. These allosteric modulators bind and stabilize the transporter in certain conformations that may modulate the transporter function in beneficial ways including altering their interaction with psychostimulants and antidepressants without affecting uptake activity of endogenous substrates.

TABLE 2

Transport inhibition constants ($K_i$)

| Drug | $K_i$ (µM) | | | |
|---|---|---|---|---|
| | hSERT | SmSERT | hDAT | SmDAT |
| (±)MDMA | 2.7 ± 0.5 | 312.8 ± 159 | ND | ND |
| Amphetamine | 27.1 ± 3 | 393 ± 26 | 0.25 ± 0.04 | 10.0 ± 0.5 |
| Cocaine | 4.7 ± 3.4 | 35.4 ± 7.6 | 0.29 ± 0.03 | 29.4 ± 3.6 |
| Citalopram | 0.03 ± 0.01 | 0.25 ± 0.1 | 157 ± 25 | 50.5 ± 4.7 |
| Clomipramine | 0.009 ± 0.005 | 0.2 ± 0.1 | ND | ND |
| Imipramine | 0.09 ± 0.03 | 0.3 ± 0.1 | ND | ND |
| Paroxetine | 0.02 ± 0.009 | 0.1 ± 0.1 | ND | ND |
| Bupropion | ND | ND | 1.06 ± 0.22 | 242 ± 36 |

Figure 7:
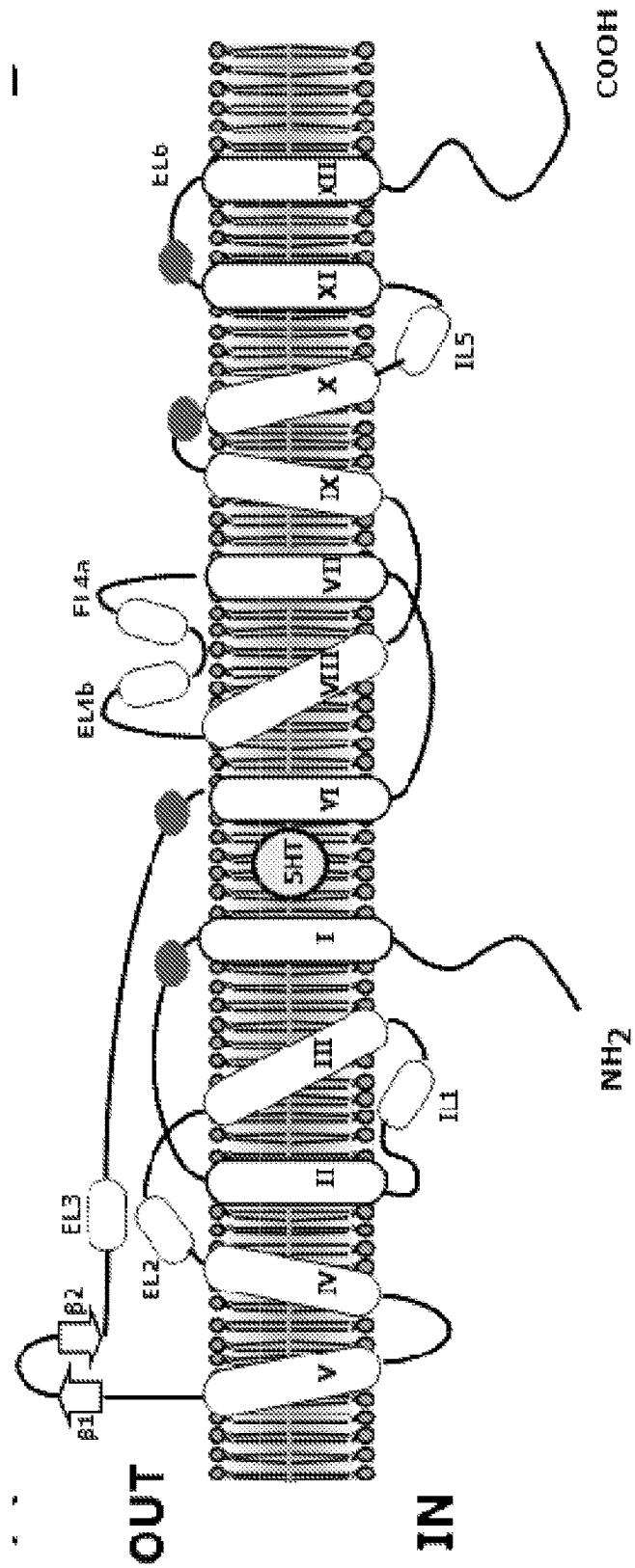
FIG. 7 is an image illustrating the transporter topology with orthosteric substrate binding site formed by TMD1 and TMD6 (in yellow as "5HT") and residues contributing to novel allosteric site (in red).

Structural domains of hSERT that modulate transporter turnover rates, substrate, and inhibitor specificity are identified and explored to enable screens for potential transporter-modulating compounds. Domains in hNET and hDAT are identified using methods for identifying similar domains in SERT as described elsewhere herein. In preliminary experiments comparing human and parasite SERT and DAT, regions in the extracellular loops outside the central translocation domain were identified that can have significant transporter-modulating effects (FIG. 7). These domains of the MATs are particularly attractive as novel drug targets as they do not interfere directly with the substrate translocation pathway and classical competitive transporter ligand binding sites, and they achieve their modulatory activities through allosteric effects. Binding pockets of hSERT accessible from the extracellular space are systematically investigated in the various structural conformations of the transporters using models based on the corresponding LeuT structures. Whether analogous domains in hNET and hDAT are similarly involved in transporter function is tested.

Chimeras Between Parasite and Human SERT

The interaction with amphetamine and on amphetamine-elicited efflux was examined using chimeras between parasite and human SERT. Unexpectedly, it was observed that replacing transmembrane domains (TMD) 1-2 or 6-7 in hSERT with its parasite counterpart had no obvious effect on amphetamine-elicited efflux by the carrier (FIG. 1). Although not wishing to be bound by any particular theory, these results suggest that the core translocation pathway is not responsible for the differences observed between the two SERTs. Other structural regions of the transporters were examined, particularly in extracellular loops (ELs) (FIG. 7). Chimeras with EL2, EL3, and EL6 replaced were functional and did not elicit amphetamine efflux. Based on these results, loop regions EL2, EL3, and EL6 were further examined to identify specific amino acid residues involved in amphetamine-elicited efflux. Based on the results from chimera EL3, residues in this region were investigated and evidence was found for a role of EL3 in combination with EL1 and outer parts of TMD1 and 6 in modulating exogenous substrate interaction. Mutation of N112 and D328 residues in hSERT in this region resulted in transporters with no significant amphetamine-elicited efflux compared with the wild-type (WT) hSERT at the amphetamine concentration tested (FIG. 1). In a dose-response experiment with MDMA, the affinity for MDMA of N112C is reduced by fivefold (FIG. 4).

In the extracellular loop 6 (EL6), the critical region was narrowed to a stretch of amino acids at positions 559-563 in mSERT. The most promising mutant, YETQ-L563V, has been assayed and dose-response curves for amphetamine-elicited efflux for WT and mutant mSERT are illustrated in FIG. 8A. No significant change in apparent affinity ($K_m$) was observed for serotonin (3.4±0.7 µM for WT and 4.7±1.3 µM for YETQ-L563V). In efflux assays, a dramatic effect was observed of the mutation compared with WT, as amphetamine and MDMA did not elicit any significant reversal of transport in the mutated SERT even at the highest testable concentration. An hDAT chimera was also produced in which the EL6 was replaced with the corresponding parasite EL6 (hDAT-EL6). Similar to what was observed with mSERT, the hDAT chimera displayed a highly reduced potency of amphetamine at eliciting efflux, as the effective concentration ($EC_{50}$) for amphetamine-evoked efflux is 720 nM, compared with 57 nM for WT DAT (FIG. 8B). Although not wishing to be bound by any particular theory, this finding strongly supports a critical and general role of EL6 in MATs in modulating substrate specificity and in supporting amphetamine-evoked efflux. Taken together, these results support the hypothesis that changes in extracellular loops cause subtle changes in the arrangement of TMDs altering the interaction between individual TMDs, between the transporter and substrates, and with the plasma-membrane lipid environment. Using these methods, molecules with novel and unique transporter-modulating properties have been successfully identified.

Modeling the Outward-Facing Three-Dimensional Structure of hSERT

Figure 9:
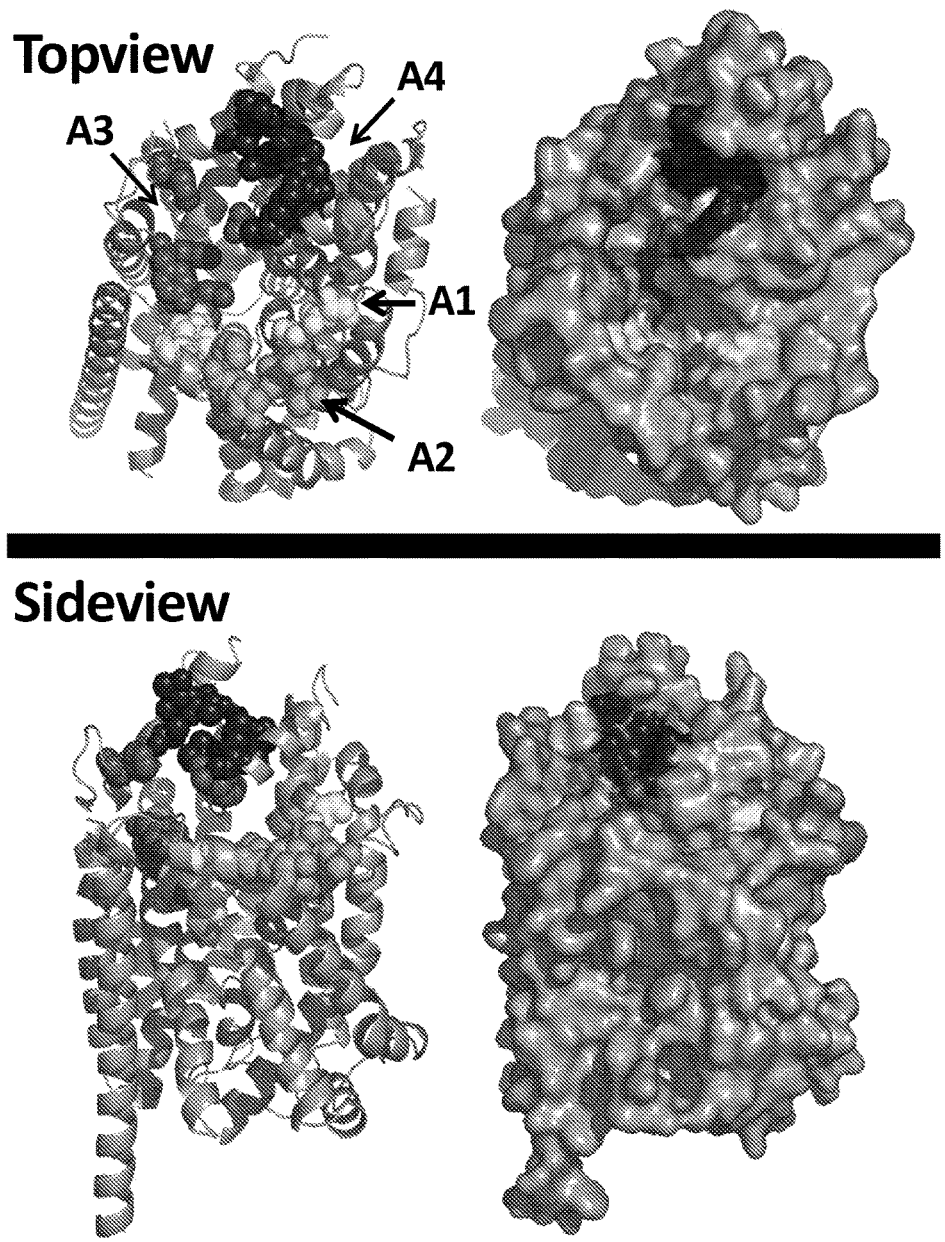
FIG. 9 is an image illustrating a structural model of SERT visualizing the allosteric pockets A1 (yellow), A2 (green), A3 (red), and A4 (blue). The original A1 site is formed by residue N112 (EL1), D328 (EL3), E494 (EL5), and R564 (EL6). A2 was identified based on the structure/function studies implicating EL6. A2 is formed by residues G324 (EL3), 1327 (EL3), and P560 (EL6). Two other pockets identified by modeling are also illustrated: A3 is formed by residue Q238 (EL2), D400 (EL4), Y487 (EL5), and E493 (EL5). A4 is formed by residues T225 (EL2), E396 (EL4), K399 (EL4), and T409 (EL4).

Using modeling methods such as those described in the Virtual Screen subheading of the methods section, structural analysis of the trajectory over the entire simulation revealed several pockets formed by amphipathic residues stabilized by interactions with the membrane (FIG. 9). These residues are distinct from the residues that form the orthosteric substrate binding pocket. One such pocket lined by residues from EL6 and EL3 (called the A1 site) was validated previously and hence was chosen for further screening studies. The initial allosteric site identified in preliminary studies (A1) is distinct from the classical inhibitor binding sites, but is linked through an intra-residue hydrogen bonding network within hSERT with a key residue D493, which is known to influence the function of the carrier. Therefore, it was hypothesized that the binding of small molecules to site A1 could significantly influence the binding of ligands within the orthosteric site. The structural information gleaned from model and structure/function studies using chimeras between parasite and human SERT described elsewhere herein has been used to identify additional potential allosteric sites that are pursued in structure/function assays as described elsewhere herein (FIG. 9).

Molecular models of hSERT in the substrate free outward open and substrate occluded conformations are modeled using the corresponding LeuT structures as templates as described elsewhere herein. Exploring different conformational states provides valuable information on dynamic changes in the respective binding pockets. This information can be employed in guiding structure-function studies as well as virtual drug screening. Significant molecular movements within the binding sites suggest that the pocket is responsive to allosteric modulation. By examining different conformational states, important information is revealed regarding what key amino acid residues within the pockets play significant roles in conformational transitions. This information guides the structure function studies described below to identify novel targets for transporter modulating compounds that display novel activities. The models are refined in a membrane-bound format using the Desmond program to obtain a production run of 30 ns as described previously. The outward-facing conformation model described elsewhere herein is also further simulated to obtain a 30-ns-long simulation trajectory for uniform comparisons. All trajectories are analyzed using VMD and in-house scripts for pocket analysis to derive information on other allosteric sites. These sites are validated using in vitro methods described elsewhere herein.

In vitro Methods

Mutagenesis:

The binding pockets are identified by the computational models using mutational and biochemical analysis. The individual amino acids are verified and replaced using conventional QuikChange (Stratagene, La Jolla, Calif.) site-directed mutagenesis methods. This method enables the production of any chimera as it is not dependent on the presence of unique restriction enzyme sites within the respective cDNAs. Based on results from hSERT, corresponding residues in hNET and hDAT are mutated. Initially, only amino acids within the identified binding pockets that are judged critical by displaying significant movement during conformational changes are tested, and therefore are also candidates for allosteric modulation. These residues are identified by calculating distances travelled by amino acids within the binding pocket during transitions between the three different conformations modeled above. Two amino acid residues in each binding pocket are initially tested.

Uptake and Efflux Assays:

Mutants are functionally tested in transfected COS-7 cells. Based on the success of the approach that identified the A1 site, the critical residues identified elsewhere herein are tested for changes in uptake kinetics and amphetamine-mediated efflux. Following this initial screen, residues displaying altered activity are tested further in uptake inhibition and ligand displacement assays. For uptake, cells are washed with PBSCM (phosphate-buffered saline with 1 mM $MgCl_2$, 0.1 mM $CaCl_2$, 100 µM ascorbic acid, 10 µM clorgyline, 100 µM pargyline, and 10 µM RO 41-0960). To initiate uptake, cells are incubated for 10 min at 25° C. with various concentrations of radiolabeled monoamine. Following uptake, cells are washed and radioactivity is counted using liquid scintillation counting. Background is determined using either mock transfected cells or inhibitors of SERT (10 µM citalopram), NET (10 µM desipramine), and DAT (100 µM cocaine). Apparent $K_m$ and $V_{max}$ are determined using nonlinear regression analysis. The interaction of WT and mutant MAT with psychostimulants and transporter inhibitors is assessed using uptake inhibition assays. Cells are transfected as described elsewhere herein, but before uptake is initiated the cells are preincubated with various concentrations of ligand for 10 min. Uptake is initiated and performed as described elsewhere herein.

For efflux experiments, transfected cells are loaded with radiolabeled serotonin or dopamine in PBSCM for 30 min. Following loading, the cells are washed extensively with PBSCM and efflux is initiated by incubating the cells with various compounds (serotonin, dopamine, amphetamine, and MDMA) for 10 min. Efflux is terminated by collecting the supernatant. Both cells and supernatant are counted by liquid scintillation counting. Efflux is calculated as ratio of supernatant over supernatant and cells.

Displacement Assays:

Transfected cells grown in 96-well plates are rinsed three times, prior to binding, with 300 µL ice-cold PBSCM per well and incubated with buffer on ice. All washing steps are carried out with an automatic plate washer. After preincubation for 15 min, buffer is aspirated and 40 µL of ice-cold PBSCM with 100 pm [$^{125}$I]RTI-55 for SERT and DAT and 10 nm [$^3$H]nisoxetine for NET and increasing concentrations of ligand are added to each well. Cells are incubated for 45 min on ice and subsequently washed with PBSCM after transferring to a 96-well glass fiber filter plate (UniFilter; PerkinElmer, Waltham, Mass.) using a PerkinElmer cell harvester. Radioactivity is counted using liquid scintillation counting.

Example 8

Discovery of Small-Molecule Modulators of SERT, NET and DAT

It has been hypothesized that allosteric pockets may be employed to modulate transporter function. Therefore, novel small molecules that can bind to the allosteric sites A1-A4 are identified and their transporter-modulating activities are examined. Molecules that enhance transporter function and alter the interaction between the transporters and their classical ligands, including psychostimulants and antidepressants, are identified. The allosteric binding pockets of hSERT, hNET, and hDAT are systematically identified that show significant movement during transitions between the different conformations and also have been verified through structure-function studies to affect transporter function. The HSB method is used to screen for allosteric modulators that bind the pockets in a conformation-dependent manner. The key component of the HSB method is design of a three-dimensional pharmacophore using structural information derived from molecular dynamics (MD) simulations and known biochemical data, such as site-directed mutagenesis of key residues of the target protein. The HSB method is described elsewhere herein under the Virtual Screening section of the methods section.

Examination of Identified Compounds for Effects on hDAT and hSERT Function

Among the 10 molecules that were tested, four compounds (ATM1 [K456], ATM2 [K571], ATM5 [K822], and ATM7 [K986]) displayed significant effects on hDAT and hSERT function in WT and mutant forms of the transporter (FIG. 10). Whereas ATM1 is a SERT-specific inhibitor, the other three compounds display unique activities of enhancing transporter function. All three compounds displayed a biphasic mode of action, enhancing transporter activity at low concentrations and inhibiting transporter function at higher concentrations (FIG. 10). ATM2 displayed higher activity towards SERT, and ATM5 displayed higher activity towards hDAT. Finally, ATM7 very potently activated serotonin uptake but also DAT activity at higher concentrations (FIG. 10). Evaluating serotonin uptake kinetics, the stimulatory effects of ATM7 were observed only at lower nanomolar concentrations of serotonin, whereas at higher concentrations there was no significant difference, and we do not observe any effect of KM-986 on $V_{max}$. This suggests a complex mechanism of action of KM-986 on SERT function and points to conformation-specific and allosteric effects.

Figure 11:
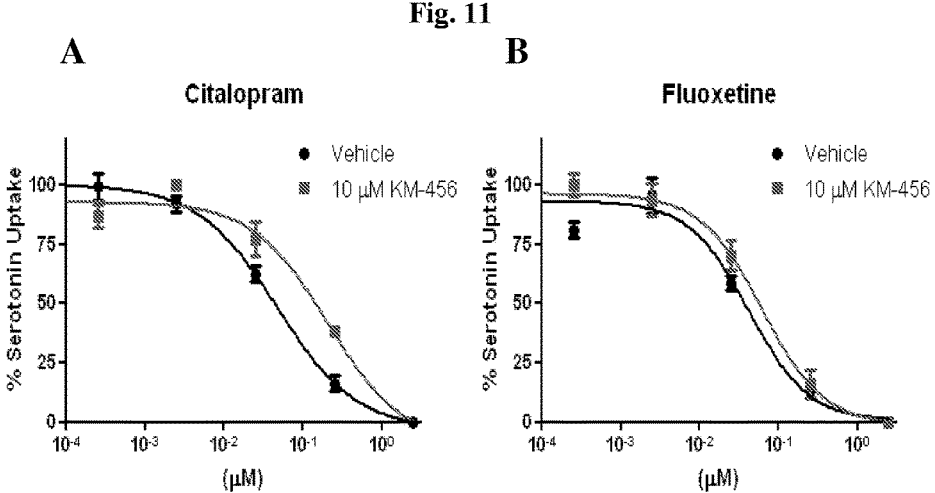
FIG. 11, comprising
Figure 12:
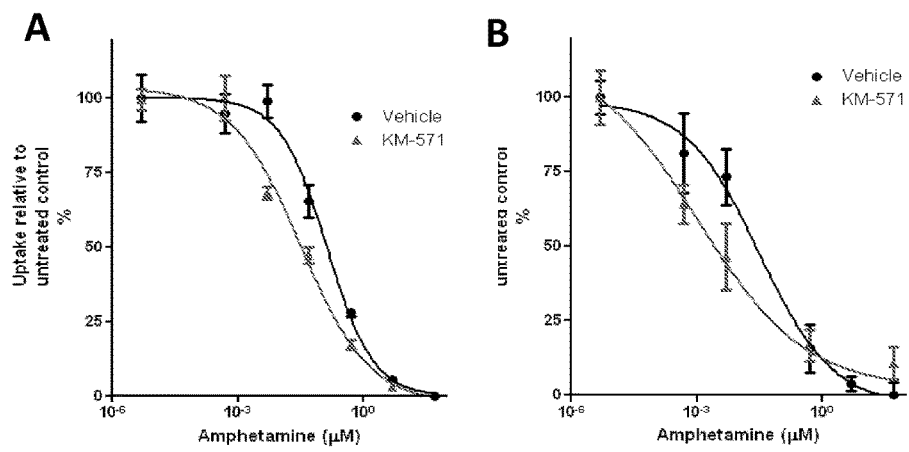
FIG. 12, comprising
Figure 13:
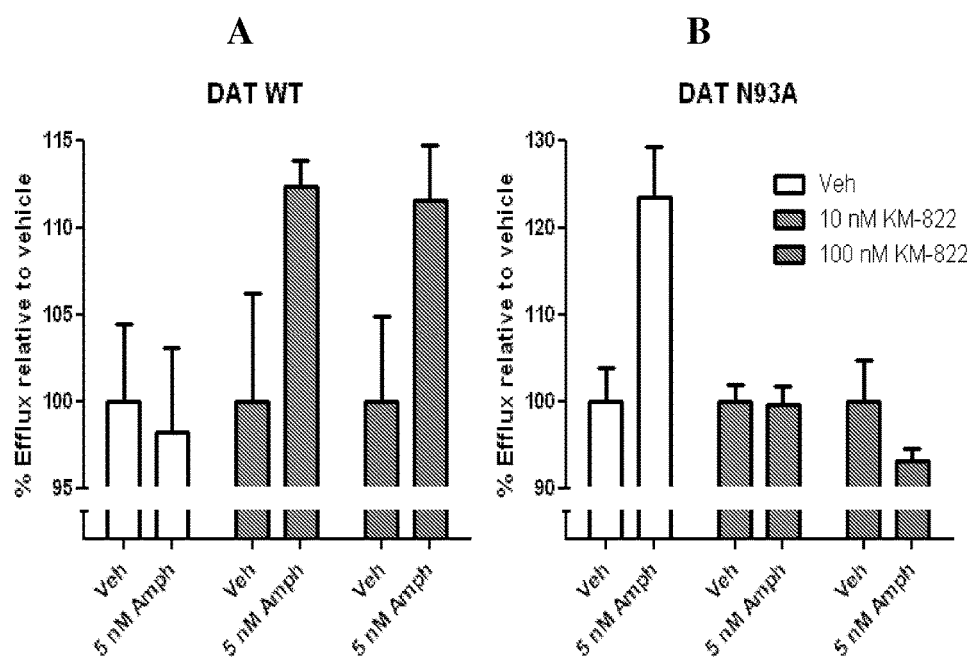
FIG. 13, comprising

It was further examined whether ATM1, ATM2, ATM5, and ATM7 alter the interaction between the transporters and exogenous ligands. ATM1 altered the interaction of SERT with SSRIs, decreasing their affinity for SERT, and interestingly the effect was stronger with citalopram than with fluoxetine (FIG. 11). Conversely, ATM2 displayed effects on DAT and NET interaction with amphetamine (FIG. 12). For both transporters, the affinity for amphetamine was enhanced in the presence of ATM2. The interaction was also fundamentally altered as the Hill coefficient of the inhibition curves is different when ATM2 is present. The third compound, ATM5, also affects the interaction of DAT with psychostimulants. In efflux assays, ATM5 potentiated amphetamine-mediated efflux in WT hDAT at low concentrations (5 nM) of amphetamine (FIG. 13).

A mutant in proximity to the A1 site (L89A; I108 in SERT) affected the binding of ATM5. This mutation resulted in increased affinity for ATM5. Although not wishing to be bound by any particular theory, this result supports the hypothesis that ATM5 interacts with the A1 site. Replacing a hydrophilic region with a hydrophobic residue in the N93A (N112 in SERT) mutant altered the effect of ATM5 by blocking amphetamine-elicited efflux in this mutant (FIG. 13). This result observed with the N93A mutant suggests that if ATM5 could be modified in a way that imitates the mutation, it may produce molecules that could disrupt the interaction between amphetamine and DAT. As described elsewhere herein, analogues of ATM5 are tested to examine whether they possess such activity. The effect of ATM7 on basal and MDMA-mediated efflux by hSERT was examined and it was observed that ATM7 potentiates MDMA-elicited efflux (FIG. 4A) but inhibits basal efflux (FIG. 4B). One of the mutants (N112C) used to identify the A1 binding pocket did not show potentiated MDMA-elicited efflux and was less sensitive to ATM7-mediated inhibition of basal efflux.

In one embodiment, the results with ATM1, ATM2, ATM5, and ATM7 strongly support the hypothesis that molecules exist that modulate transporter-ligand interaction. The methods described herein have successfully identified molecules with novel and unique transporter-modulating properties.

In Silico Screening and In Vitro Validation

In silico screening is performed for small molecules for other pockets such as A2, A3, and A4. Three-dimensional pharmacophores for each allosteric site are designed by closely monitoring the structural dynamics of core residues with residues that link to the orthosteric substrate and ligand binding sites and the membrane. In addition, preliminary biochemical studies on mutants aid in the design of the pharmacophore that is used for screening the 3 million compound library using the HSB method described under the Virtual Screening section of the methods section. Hits from the screening are filtered for blood-brain barrier (BBB) permeability and drug-like properties as implemented in the HSB method. The best-ranking molecules are validated for transporter function using in vitro methods. Analogues of hit molecules are identified in the library.

Functional assays are employed to further characterize experimental compounds and elucidate their mechanisms of action. These assays include examinations of the effect of preincubation with experimental drugs on uptake and efflux assays and interaction with exogenous ligands such as those described in Example 7.

Example 9

Figure 14A:
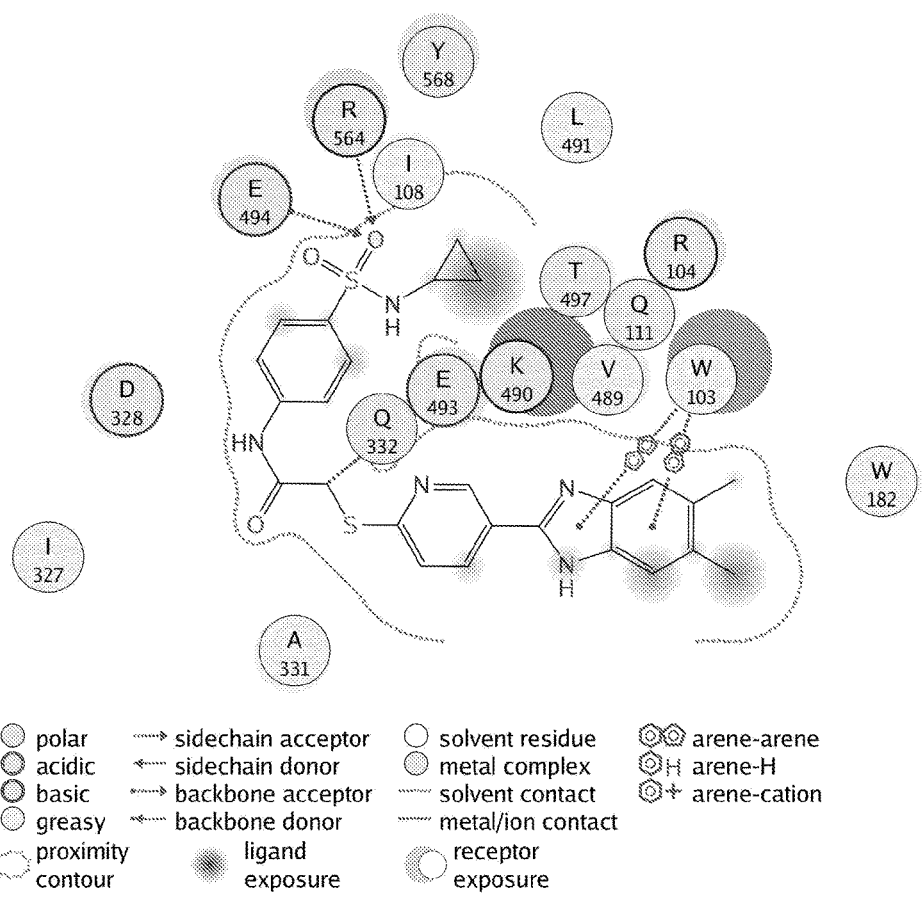
FIGS. 14A-14B, illustrates the interactions of ATM1 (KM-456) and ATM2 (KM-571) with residues forming the allosteric sites in hSERT as depicted by 2D ligand interaction diagrams generated using the LIGX module of MOE software.
Figure 14B:
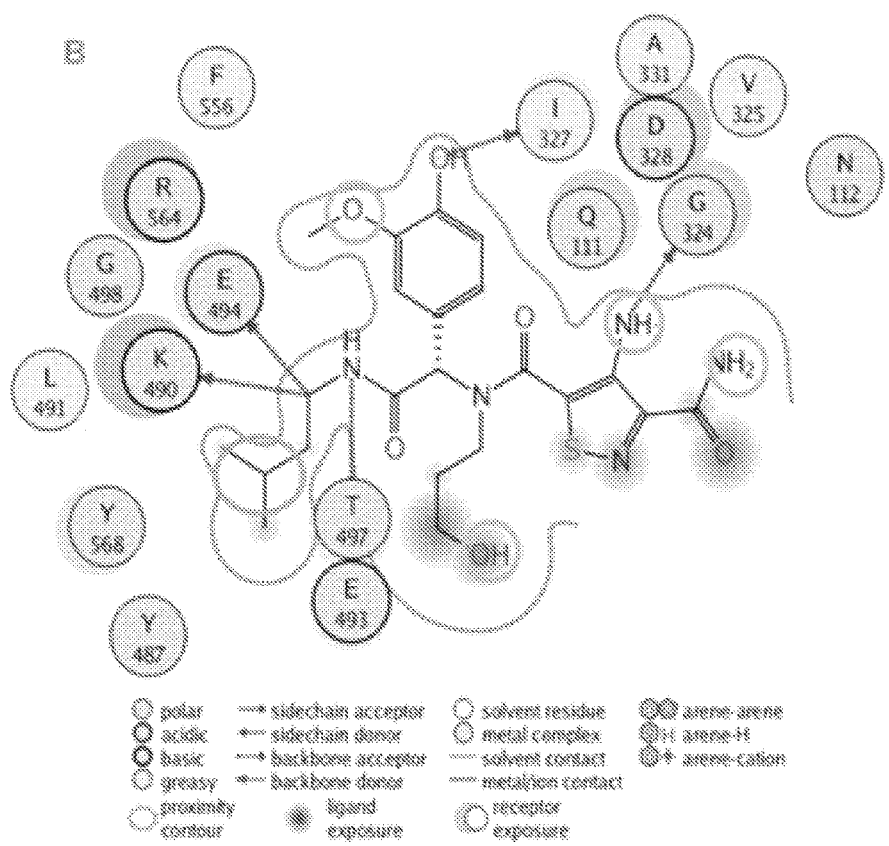

Investigation of Transporter-Modulating Mechanism of Action of Identified Molecules To take full advantage of the molecular targets within the transporters and the identified molecules for the development of more efficacious molecules, and to begin using them as tools for understanding transporter function, the mechanisms of action of the investigational compounds are elucidated. A battery of biochemical assays are employed to investigate how the functional effects of the compounds are produced. Both mutants of the transporters and analogues of experimental compounds are utilized to explore the network of interactions between the new allosteric sites, the substrate, and classical ligand binding orthosteric site. Specifically examining how the experimental molecules affect conformational states of the transporter provides important knowledge of the mechanism of action. The 10 best performing compounds identified in Example 2 are examined.
Effects of ATM5 and ATM7 in DAT and SERT Through modeling studies, allosteric pockets were identified that are connected through a network of hydrogen-bonded interactions, including interactions with the membrane and water molecules. Key residues in SERT that form the backbone of the network include residues such as N112, G324, D328, and E493. N112 is one such critical residue as it bridges residues from A1 and the ligand and substrate binding sites via a hydrogen-bonded network (FIG. 14). Mutation of the corresponding residues in DAT (N93A, N112 in SERT) greatly influenced the effects of ATM5 on functional effects of the transporter induced by psychostimulants (FIG. 13). Similar results were observed in hSERT wherein the presence of ATM7 at a concentration of 1 μM enhanced MDMA-elicited efflux in the WT SERT but had no effect on MDMA-elicited efflux in the N112C mutant (FIG. 4).

It was hypothesized that uptake activity and enhanced MDMA-elicited efflux by SERT in the presence of ATM7 may be due to a mechanism of action of ATM7 that stabilizes SERT in an outward-facing conformation, enhancing initial substrate interaction and resulting in increased serotonin uptake and MDMA-elicited efflux. It was also hypothesized that this stabilization may also reduce the levels of intracellular serotonin exiting the cells in the absence of an extracellular substrate to facilitate SERT into an inward-facing conformation, explaining the inhibition caused by KM-986 on basal efflux (FIG. 4). This hypothesis was tested using a mutation in SERT (Q332C) that monitors the conformation of SERT. It was observed that the susceptibility of the mutant Q332C towards the thiol-modifying reagent MTSET ([2-(trimethylammonium)ethyl methanethiosulfonate bromide]) was sensitive to preincubation with substrate and inhibitor.

A substrate (serotonin) would prevent modification while an inhibitor (cocaine) would enhance modification. It was hypothesized that the enhanced modification by cocaine would signify that an outward conformation had been stabilized. The effect of ATM7 was compared with the effects of serotonin and cocaine on the reactivity of the Q332 mutant and found that KM-986 behaves more like cocaine than serotonin (FIG. 5B). These results support the hypothesis that KM-986 stabilizes SERT in an outward-facing conformation, however this stabilization is different from that of cocaine as ATM7 does not inhibit transport activity.
Structure/Function and Chemical Biology Methods In order to examine the structural mechanisms behind the transporter-modulating activities of the experimental drugs, structural models of binding sites are developed by docking the transporter-modulating investigational compounds in their respective binding pockets, thus achieving a better understanding of which structural features within the transporters determine the interaction with the investigational compounds. Models are developed which contain the molecules docked in the different transporter conformational states in order to calculate binding affinities and therefore elucidate in which states the compounds most likely bind. This strategy is then used to identify specific residues within the transporters that mediate the interaction. The computational predictions are tested biochemically by site-directed mutagenesis.

The importance of the various functional groups within the investigational compounds is examined by testing analogues in order to initiate preliminary structure/activity relationship studies. To demonstrate this approach, ATM1 and ATM2 were docked to their respective binding pockets in SERT. These two molecules were chosen because of their significantly different activities toward SERT function (FIGS. 10 and 11). Both similarities and differences were observed between their interactions with SERT. Taking advantage of such similarities and differences enables the exploration of structural domains within SERT that mediate the activities of these compounds, and reveals novel functional information regarding SERT. For example, a consistent interaction between both compounds and residues K490, E494, and R564 was observed. Conversely, a specific interaction was observed between residue R104 and ATM1. This interaction with residue R104 was not observed with ATM2.

Specific interactions were observed with ATM2 and residues G324 and D327 that were not clearly observed with ATM1. These residues are mutated and their effects are tested on the interaction and efficacy of ATM1 and ATM2. A specific interaction between R104 and molecule ATM1 has been observed, and it has been demonstrated that this interaction affects the interaction of SERT with citalopram (FIG. 11).
In Vitro Validation Assays are employed to characterize experimental compounds and elucidate their mechanisms of action. These assays include examinations of the effect of preincubation of WT and mutated transporters with experimental drugs on uptake, binding, and efflux assays, as described elsewhere herein. In addition, the effects of experimental drugs on structural and conformational states of the transporter, transporter ion dependence, dissociation, and dimerization are examined.
Structural and Conformational Changes:

Mutants are used to investigate effects of the experimental drugs on conformational states of the transporter. These mutants include the hSERT mutant Q332C (Q317 in DAT) and DAT 159C. Because of the sensitivity of WT DAT and SERT to MTSET, all mutations are produced in the appropriate MTSET-insensitive background (SERT C109A or DAT C90A/C306A). Transfected cells are washed with PBSCM and incubated with varying concentrations of MTSET. After a 10-min incubation, the cells are washed in PBSCM and assayed for uptake with 250 nM of [$^3$H]5-HT or [$^3$H]5DA for 10 min, as described elsewhere herein. Uptake is then terminated by washing with PBSCM. The Y335A in DAT is used to probe whether an investigational drug interacts with the inward or outward-facing conformation by performing dose-response assays on WT and Y335A DAT and examining changes in affinity of experimental drugs.
Ion Dependence:

To examine whether experimental compounds have an effect on sodium dependence of the transporters, transport under conditions in which Na$^+$ concentration is reduced in the uptake buffer is compared to transport under conditions in which Na$^+$ is completely substituted by Li$^+$. In ion substitution experiments, Na$^+$ or Cl$^-$ ions are substituted in a HEPES-buffered saline solution with N-methyl-d-glucamine-Cl or sodium gluconate salts, respectively.
Dissociation Studies:

Preclinical research has shown that some SERT inhibitors can bind to two distinct binding sites on SERT, a primary high-affinity binding site and a low-affinity allosteric binding site. Whether experimental compounds affect the dissociation of the allosteric ligands is performed via dissociation studies on DAT and SERT. Dissociation rates are determined on membrane preparations from transiently transfected COS-1 cells. A [$^3$H](−)-2-β-carbomethoxy-3-β-(4-fluorophenyl)tropane-DAT or [$^3$H]citalopram-SERT complex is formed during a 60-min incubation at 4° C. The kinetics of dissociation are followed by adding to the complex a solution containing varying concentrations of SERT and DAT inhibitors, subsequently incubated for increasing intervals at room temperature. Dissociation curves are obtained by plotting residual binding versus time of dissociation. As the complex dissociates according to first-order kinetics, the dissociation rates, $k_r$ values, are determined.

Example 10

Investigation of In Vivo and Ex Vivo Activity of Allosteric Transporter Modulators By producing molecules that modulate MAT function, molecules that affect brain monoamine homeostasis are identified. Studies are initiated in animals and ex vivo preparations. The effect of the experimental compounds is evaluated on monoamine homeostasis and behavioral assays are employed to evaluate the behavioral outcomes of the experimental drugs as well as the efficacy and therapeutic potential of the identified compounds.

Microdialysis

To understand the effects of experimental drugs on in vivo levels of monoamines, microdialysis studies are performed in rats treated with experimental drugs. Rats weighing 200-250 g are anesthetized with inhaled isoflurane for surgery. Guide cannulae are implanted at the level of the dorsal hippocampus (5HT) (A: −3.2, L: 12.0, V: 3.0 mm, relative to the bregma) or the prefrontal cortex (DA and NE) (A: 3.2, L: 0.4, V: 4.0 mm, relative to the bregma). Experiments are performed at least 3 days after surgery in awake and freely moving rats. A dialysis probe with an outer diameter of 0.22 mm and a length of 2 mm is inserted into the guide cannula.

On the day of the experiment, the probes are perfused with Ringer's solution (147 mM NaCl, 4 mM KCl, and 2.3 mM CaCl$_2$) at a flow rate of 1 μL/min. After an initial perfusion period of 2-3 h, dialysate samples are collected every 20 min. Online quantification of NET, SERT, and DAT in the dialysate is accomplished by high-performance liquid chromatography coupled to electrochemical detection. Monoamines are separated using a cation exchange column and a mobile phase consisting of 0.1 M ammonium acetate buffer at pH 6.0, 0.05 M sodium sulfate, 50 mg/L Na$_2$EDTA, and 30% methanol (v/v). Three basal samples are collected before drug administration. The drugs are then administered, and the samples are collected for an additional 160 min. At the completion of the experiment, the rats are sacrificed, and the probes are perfused with 2% Fast Green to allow for histological verification of probe placement. Approximately 8 to 10 animals are required for each experimental setup.

Fast Scan Cyclic Voltammetry (FSCV)

To examine changes in monoamine release and uptake kinetics following treatment with novel compounds in an ex vivo model, FSCV is employed. Rats are euthanized, and brain slices containing the caudate putamen, dorsal raphe, or ventral bed nucleus of the stria terminalis (vBNST) are collected.

To verify specificity, specific inhibitors of the three transporters are employed: GBR-12909 for DAT, desipramine for NET, and citalopram for SERT. DA, NE, or 5-HT release is electrically evoked every 5 min and their levels recorded to establish baseline levels of release and maximal uptake rates ($V_{max}$). Experimental compounds are superfused with concentrations based on results obtained from methods described elsewhere herein. Changes in evoked release and uptake rates are determined using previously described methods of Michaelis-Menten-based kinetic modeling. How experimental compounds affect the ability of amphetamine, cocaine, and antidepressants to interact with DA, NE, and 5-HT transporters is examined. Slices are superfused with single concentrations of experimental compounds followed by a dose-response experiment with the various transporter ligands. Approximately 8 to 10 animals are required for each experimental setup.

Behavior

To test the effect of drugs in animal models, rats are evaluated in an open-ended screen that involves gross behavioral analysis based on the SHIRPA and Irwin screens. The assessment of each animal begins by observing undisturbed behavior in a viewing jar. Throughout this procedure, vocalization, urination, general fear, irritability, and aggression are recorded. Balance and coordination are quantified with an accelerating rota-rod, which measures the ability of the animal to remain on a rotating drum. The effects on the perception of pain are measured with the mouse hot plate test. The tertiary screening stage in this protocol is tailored to the analysis of psychiatric disorders. Anxiety is measured using previously described methods, including open-field activity, in which patterns of exploration in a brightly lit arena are recorded, as well as the elevated plus maze. Learning and memory are tested with the Morris water maze, in which rats have to locate a submerged platform using distal cues. Approximately 8 animals are required for each experimental setup.

To further test for the therapeutic and behavioral potential of experimental drugs, the lead candidate molecules are tested in relevant animal models of monoaminergic signaling. Initial screening examines the effects of experimental drugs on two different behaviors that involve monoaminergic signaling and are modulated by psychostimulants and antidepressants. These include the locomotion assay, which tests the effect of investigative molecules alone or in combination with amphetamine or cocaine in order to evaluate whether the compounds can modulate the well-established effects of amphetamine and cocaine on locomotion. Rats are tested individually in chambers equipped with light-sensitive detectors and corresponding infrared lights. Each light-beam interruption is registered as one horizontal activity count. Each dose or dose combination is injected intraperitoneally, and each rat is only used once. Rats are given injections and immediately placed in the apparatus for 8 h, with activity counted every 10 min. Timing of drug administration is based on the results from microdialysis. Microdialysis yields information regarding the time when the investigational compounds produce the strongest effects on neurotransmitter levels. Information from the initial behavioral screens described above is used to identify time points associated with the strongest behavioral effects.

The tail suspension test is used in another behavioral assay that examines monoaminergic signaling. The test is based on the principle that mice subjected to the short-term, inescapable stress of being suspended by their tails develop an immobile posture. The effects of the experimental compounds administered alone are tested. In addition, whether the compounds modulate the well-established effects of antidepressants including SSRIs and tricyclic antidepressants on this assay is tested. Rats are tested individually. Each dose or dose combination is injected intraperitoneally 30 min before the test or at other times based on the results from microdialysis and general behavioral screens as described for the locomotion assays. Each rat is used only once. The tail of the rat is attached to a tail hanger attached to a strain gauge. Movements are automatically detected with 2 levels of analysis available in the system. Direct measurements are displayed for the immobility, the energy, and the power of the motion and a second level of analysis enables access to the recorded raw data graphs and values for in depth analysis. All experiments are recorded and can be replayed at any time.

Example 11

Characterizing Allosteric Pockets on hDAT

Structural domains of hDAT that modulates transporter turnover rates, substrate and inhibitor specificity are identified and examined to enable screens for potential hDAT modulating compounds. These domains of hDAT are particularly attractive drug targets because they will not interfere directly with the dopamine translocation pathway. Although not wishing to be bound by any particular theory, these domains of hDAT more likely achieve their modulatory activities through allosteric effects. All binding pockets of hDAT that are accessible from the extracellular space are systematically investigated in the various structural conformations of hDAT using models based on the corresponding LeuT structures.

Chimeras

Chimeras produced between the parasite and the mouse SERT (Table 3) were used to examine the interaction with amphetamine and amphetamine elicited efflux. Although not wishing to be bound by any particular theory, the results from chimeras in TMD1-2 and 6-7 suggest that the core translocation pathway is not responsible for the differences we observed between the two SERTs. The results also point to the transmembrane domains (TMD) 11-12 region as important for the absence of efflux in the parasite SERT.

TABLE 3

Chimeric hSERT transporters and their functional effect

| TMD: | 1-2 | 1-3 | 1-5 | 1-6 | 1-8 | 1-12 | 4-6 | 6-7 | 6-8 | 6-10 | 9-10 | 10-12 | 11-12 |
|---|---|---|---|---|---|---|---|---|---|---|---|---|---|
| Active | + | − | − | − | − | − | + | + | − | − | − | − | + |
| Efflux | + | na | na | na | na | − | + | + | na | na | na | na | − |

The numbering signifies which transmembrane domains (TMD) in the mSERT were replaced in the corresponding domains in the SmSERT.

To further identify relevant regions of hSERT, chimeras of several of the extracellular loops were constructed. Chimeras with EL2, EL3, and EL6 replaced were functional and did not elicit amphetamine efflux. Chimera EL4 was not functional. Based on these results, some of the loop regions were further pursued. In EL6, residues were identified in this region that modulates the amphetamine-elicited efflux by SERT. The critical region was narrowed to a stretch of amino acids at positions 559-563 in mSERT. The most promising mutant, YETQ-L563V, was assayed and dose-response curves for amphetamine elicited efflux for wild type (WT) and mutant mSERT are illustrated in FIG. 8.

No significant change in apparent affinity ($K_m$) for serotonin (3.4±0.7 μM for WT and 4.7±1.3 μM for YETQ-L563V) was observed. In efflux assays, a dramatic effect of the mutation compared with WT was observed, as amphetamine and MDMA did not elicit any significant reversal of transport in the mutated SERT even at the highest testable concentration. A hDAT chimera was produced in which the EL6 was replaced with the corresponding parasite EL6 (hDAT-EL6). Similar to what was observed with mSERT, it was observed that the hDAT chimera display a highly reduced potency of amphetamine at eliciting efflux, as the effective concentration (EC50) for amphetamine-evoked efflux was 720 nM compared to 57 nM for WT DAT (FIG. 8B). This finding strongly supports the hypothesis for a critical and general role of EL6 in MATs for modulating substrate specificity and in supporting amphetamine-evoked efflux.

These studies also support the hypothesis for the presence of other allosteric sites in DAT, including residues within EL3 in combination with EL1 and outer parts of TMD1 and 6. The mutation of N112 and D328 residues in hSERT in this region resulted in transporters with less amphetamine elicited efflux compared to the WT hSERT. It is hypothesized that changes in extracellular loops may cause subtle changes in the arrangement of TMDs altering the interaction between individual TMDs, between the transporter and substrates, and with the plasma-membrane lipid environment.

Computational Methods

Figure 15:
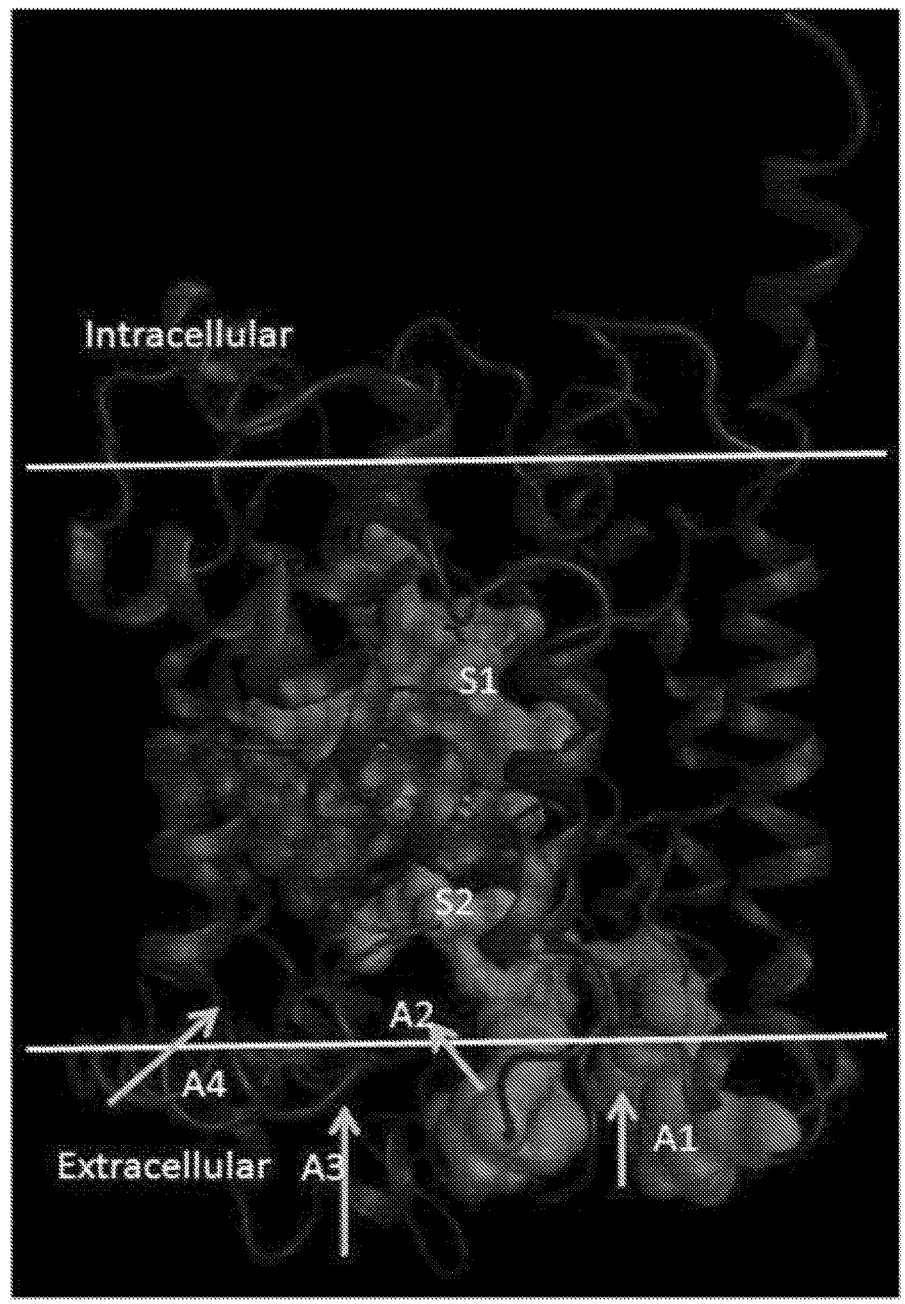
FIG. 15 is an image illustrating a structural model of hDAT represented in a ribbon model with membrane positions marked by white horizontal lines. Residues forming site O1, C2, ion binding site and allosteric site A1 are shown in surface representation and colored orange, yellow, red, and green respectively. Other potential allosteric sites are marked with arrows and labeled A2 through A4.

The human DAT was modeled using computational methods such as those described in the Virtual Screening section of the methods section. Structural analysis of the trajectory over the entire simulation revealed the formation of several pockets formed by amphipathic residues stabilized by interactions with the membrane. These residues are distinct from the residues that form the orthosteric site or O1 pocket that binds endogenous substrate or the proposed alternative cocaine binding site or C2 site as shown in FIG. 15. One such pocket lined by residues from EL6 and EL3 (the A1 site) was validated in experimental studies as described elsewhere herein and was selected for further screening studies. The allosteric site A1 is distinct from the cocaine binding site (C2), but is linked through an intra-residue hydrogen bonding network within hDAT with key residue D476, which is known to influence the binding of cocaine. Therefore, it was hypothesized that the binding of small molecules to site A1 may significantly influence the binding of cocaine or psychostimulants (FIG. 8B) but not the endogenous substrates at the orthosteric—O1 sites.

Molecular models of hDAT in both substrate occluded and inward facing form are modeled using the corresponding LeuT structures as templates using methods described elsewhere herein for hSERT. The models are refined in a membrane bound format using the Desmond program to obtain a production run of 30 ns using methods described elsewhere herein for hSERT. The outward-facing conformation model described elsewhere herein is also further simulated to obtain 30 ns long simulation trajectory for uniform comparisons. All trajectories are analyzed using VMD and in-house scripts for pocket analysis to derive information on other allosteric sites. These sites are validated using in vitro methods described elsewhere herein for hSERT. Mutagenesis and uptake and efflux assays are performed using methods such as those described in Example 7.

Example 12

Screening for Small Molecule Allosteric Modulators of hDAT

Novel small molecules that can bind to allosteric sites A1 through A4, block the binding of psychostimulants to the C2 site while not affecting the binding of the substrates to the O1 site are designed. All allosteric binding pockets of hDAT that are accessible from the extracellular space in other models described elsewhere herein for hSERT are systematically investigated in order to design allosteric modulators using the HSB method. Identified molecules are tested in functional assays. Biochemical assays that investigate the effects of molecules on conformational states of hDAT are employed because conformational changes are important for the successful identification of active molecules. Mutations at site N93A and N112C of A2 provide additional structure-activity relationship (SAR) information about ATM5 that is incorporated in the design of analogues of ATM5 that can be used to annul the dose-dependent effects of psychostimulants.

Effects of ATM5 and ATM7 on hDAT and hSERT

Figure 10A:
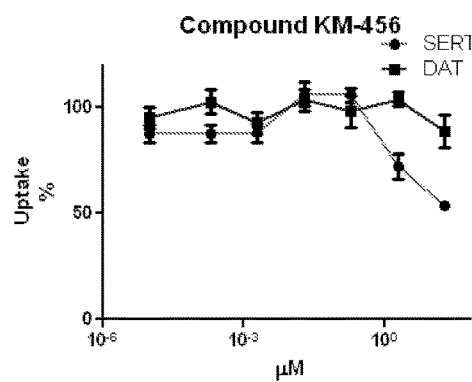
FIGS. 10A-10D, illustrates results from hDAT and hSERT uptake assays with transporter modulators.
Figure 10B:
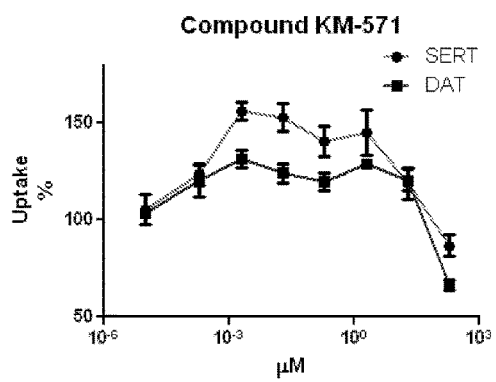
Figure 10C:
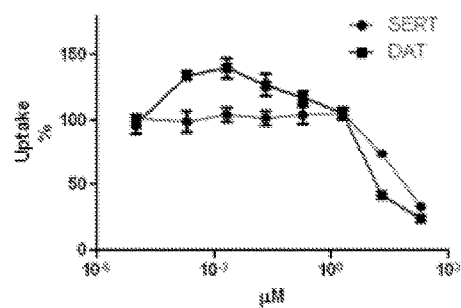
Figure 16A:
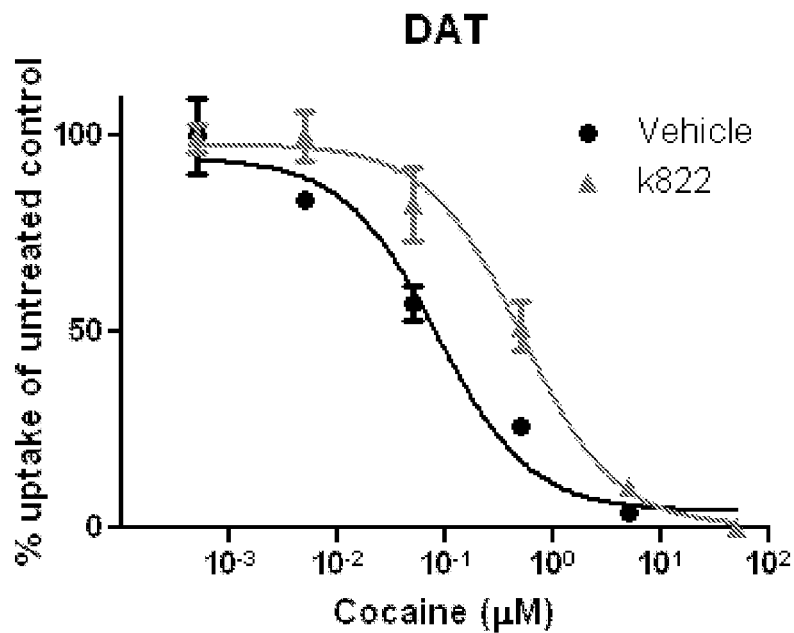
FIGS. 16A-16B, illustrates the finding that ATM5 (KM-822) affects the interaction of DAT with psycho stimulants.
Figure 16B:
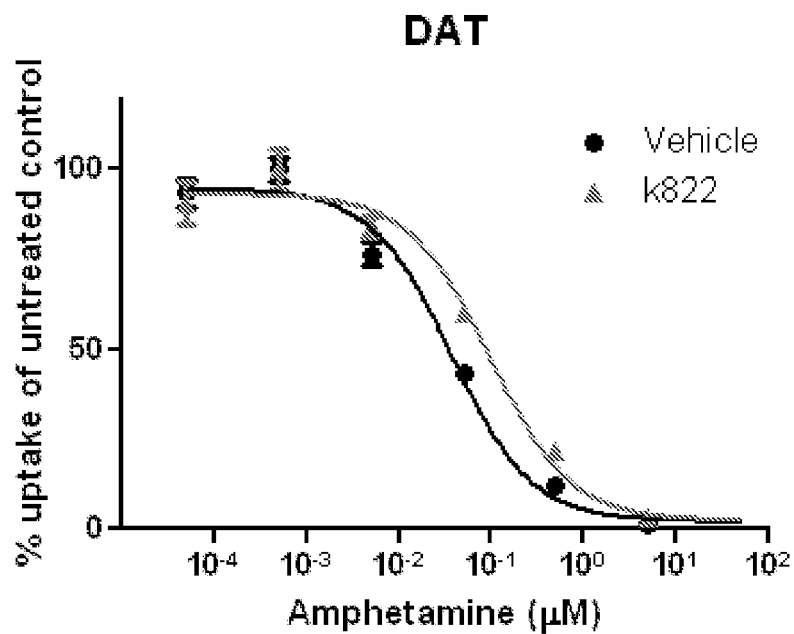

Using screening methods described under the Virtual Screening section of the methods section, 10 molecules were identified and tested for their ability to interfere with the uptake and amphetamine induced efflux of serotonin and dopamine at their respective transporters. Of these 10 compounds, ATM5 and ATM7 displayed interesting effects on hDAT and hSERT in WT and mutant forms of the transporter (FIG. 10). ATM5 displayed higher activity towards hDAT than hSERT, with a biphasic activity enhancing hDAT activity at low concentrations and inhibiting hDAT function at higher concentrations (FIG. 10C). The effects of ATM5 on a set of DAT functions were tested. Besides enhancing uptake at low concentrations of DA, ATM5 also affected the interaction of DAT with psychostimulants. In dopamine uptake inhibition assays with cocaine, a decreased affinity for cocaine was observed in the presence of ATM5 (FIG. 16A). These results validate the results from MD simulation in which A1 site could modulate the C2 site (cocaine binding site) via the hydrogen bond network. Although not wishing to be bound by any particular theory, taken together these results suggest that it is possible to develop cocaine antagonists that affect the interaction of cocaine with hDAT without affecting transport activity. These studies are extended using site-directed mutation of key residues that connect the A1 and C2 sites such as D476 in addition to designing and testing additional analogues of ATM5 that abrogate the binding of psychostimulants and not the endogenous substrates.

Figure 10D:
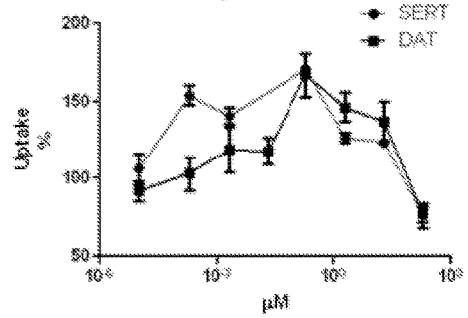

In a dose-response assay, ATM7 was observed to potently activate serotonin uptake up to 50%. In a similar assay with DAT, activation of serotonin uptake was also observed, albeit at higher concentrations of ATM7. ATM7 displayed a bell shaped response as ATM7 at higher concentrations inhibited both SERT and DAT (FIG. 10D). When evaluating serotonin uptake kinetics, it was found that the stimulatory effects of ATM7 are observed only at lower nanomolar concentrations of serotonin, whereas at higher concentrations, there was no significant difference and no effect of ATM7 on Vmax was observed. Although not wishing to be bound by any particular theory, these results suggest a complex mechanism of action of ATM7 on SERT function and points to conformation specific and allosteric effects Cooperative Effects Between Allosteric Sites It was observed that hDAT mutants from the neighboring allosteric site A2 have a strong co-operative effect on the binding of ATM5 at site A1. In dopamine uptake inhibition assays, the L89C mutant displayed increased affinity for ATM5, supporting the modulatory role of ATM5. In efflux assays, ATM5 potentiated amphetamine mediated efflux in WT hDAT at low concentrations (5 nM of amphetamine). Replacing a hydrophilic region with a hydrophobic residue at the A2 site, as in the N93A mutant, elicited a strong efflux at the same low concentrations of amphetamine. This efflux was blocked by the addition of ATM5 (FIG. 13A). Although not wishing to be bound by any particular theory, this result with the N93A mutant signifies that if ATM5 can be modified in a way that imitates the mutation it would produce molecules that can act as antagonist of amphetamine/DAT interactions. The effect of ATM7 on basal and MDMA mediated efflux by hSERT was also examined, and it was found that ATM7 potentiates MDMA-elicited efflux but inhibits basal efflux. Interestingly a mutant (N112C) within the A2 binding pocket did not show potentiated MDMA-elicited efflux and was less sensitive to ATM7-mediated inhibition of basal efflux (FIG. 4B).

Methods

In silico screening for small molecules for all the other pockets identified in Example 11 is performed using methods described under the Virtual Screening section of the methods section. Three dimensional pharmacophores are designed for each allosteric site by closely monitoring the structural dynamics of core residues with residues that link the C2 site and the membrane. The design of the pharmocophores used for screening the 3 million compounds library using the HSB method is aided by the results of biochemical studies described below. Hits from the screening are filtered for BBB permeability and drug like properties as implemented in the HSB method. The best-ranking molecules are validated for transporter function using in vitro methods such as those described in Example 8.

Structural and Conformational Changes

The hSERT mutant Q332C (Q317 in DAT) and DAT 159C are used to investigate effects of the experimental drugs on conformational states of the transporter. Because of the sensitivity of WT DAT and SERT to MTSET, all mutations are produced in the appropriate MTSET insensitive background (SERT C109A or DAT C90A/C306A). Transfected cells are washed with PBSCM and incubated with varying concentrations of MTSET added from a stock solution prepared in dimethyl sulfoxide (DMSO). After a 10 min incubation, the cells are washed five times in PBSCM and assayed for uptake with 250 nM [$^3$H]5HT or [$^3$H]5DA for 10 min at room temperature using methods such as those described in Example 9. Uptake is terminated by washing twice with PBSCM.

The Y335A mutation in DAT a useful tool to probe whether an investigational drug interacts with the inward or outward-facing conformation of the transported. This interaction is tested by performing dose response assays on WT and Y335A DAT and examining changes in affinity of experimental drugs. Ibogaine, a hallucinogenic alkaloid found in the roots of the West African shrub *Tabernanthe iboga*, is employed. This compound has been found to interact preferentially with the inward-facing conformation of DAT and SERT and can be used in uptake inhibition and ligand binding displacement assays to establish the ratio of inward- or outward-facing conformations.

Synaptosomal Assays

Biochemical synaptosome-based experiments are performed to determine how endogenously expressed DAT and SERT are modulated by the identified compounds. Dopamine and serotonin uptake and efflux are measured by using synaptosomes prepared from fresh rat striata and hippocampi, respectively. The tissue is homogenized in ice-cold Krebs-Ringer's buffer containing 0.32 M sucrose. The samples are centrifuged for 10 min at 1000 g, the pellet is discarded, and the remaining supernatant is centrifuged for an additional 15 min at 16,000 g. The resulting pellet (P2) is dissolved in uptake buffer (25 mM HEPES, 120 mM NaCl, 5 mM KCl, 1.2 mM $MgSO_4$, 1 µM pargyline, 2 mg/mL glucose, 0.2 mg/mL ascorbic acid, pH 7.5). The uptake of radiolabeled dopamine or serotonin in the presence of increasing concentrations of unlabeled dopamine or serotonin is performed for 3 min at 25° C. in uptake buffer and terminated by filtering and extensive washes with uptake buffer. Background levels are estimated in the presence of either cocaine for dopamine uptake or citalopram for serotonin uptake.

For efflux experiments, the synaptosomes are prepared as described above and loaded with [$^3$H]dopamine (10 nM), or [$^3$H]serotonin (20 nM) at 25° C. for 20 min in uptake buffer. These assays are performed in 1.5-mL Eppendorf tubes. Loading of radiolabeled substrate is terminated by addition of 1 mL of uptake buffer into the tubes and immediate centrifugation at 10,000 g at 4° C. for 3 min. After preloading, the samples are washed once and exposed to vehicle, transporter substrates, or transporter inhibitors in efflux buffer (25 mM HEPES, 120 mM NaCl, 5 mM KCl, 1.2 mM $MgSO_4$, 1 µM pargyline, 2 mg/mL glucose, 0.2 mg/mL ascorbic acid, pH 7.5) at 25° C. for 10 min. The efflux process is terminated by addition of 1 mL of ice-cold efflux buffer into the tubes. After centrifugation at 10,000 g at 4° C. for 3 min, the supernatant containing the effluxed serotonin or dopamine is collected, and the synaptosomes are washed twice and incubated in a lysis buffer for 30 min on a shaking platform at 200 rpm. The remaining synaptosomes are lysed. Both synaptosomes and supernatant are quantified by liquid scintillation counting. Efflux is calculated as ratio of supernatant over sum of supernatant and synaptosomes.

Example 13

Determining Structure-Function Relationships Between Orthosteric and Allosteric Sites Using Modulators as Probes It has been demonstrated that ATM5 and ATM7 have the ability to modulate the effects of psychostimulants even under low concentrations without interfering with the normal functioning of the transporters. The network of interactions between the allosteric and the psychostimulant binding orthosteric sites is traced and the molecular mechanisms of modulation is explored. SAR is derived using small molecule allosteric modulators and site-directed mutagenesis in an iterative mode. Studies identifying allosteric pockets that can induce conformation specific changes to the transporter are described in Example 8. Studies demonstrating ATM7 binding stabilizes the outward-facing conformation of hSERT are described in Example 8.

Computational/Medicinal Chemistry Methods

Figure 17:
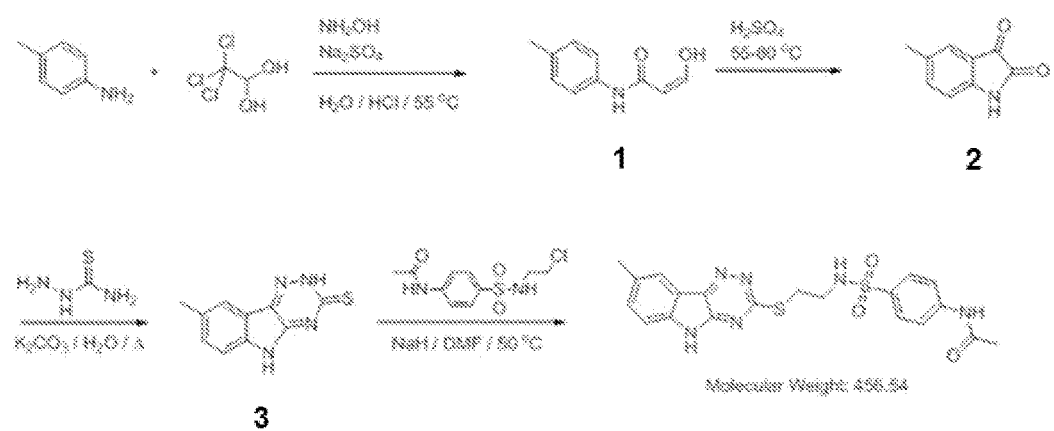
FIG. 17 is a scheme illustrating an exemplary non-limiting route to synthesize ATM5.

Analogues of ATM5 and other lead compounds that may emerge from the screening are designed. ATM5 is a novel compound possessing a triazinoindole core that is a well-known chemical core amenable for easy synthesis and lead modifications using optimal medicinal chemistry methods. ATM5 and several of its analogues are available from commercial vendors derived using combinatorial chemistry methods. Using the synthetic route such as that described in FIG. 17, ATM5 can be synthesized. Specific analogues identified during SAR studies that may not be commercially available are synthesized using this synthetic route.

The synthesis of ATM5 can be easily performed in three steps with options for integrating commercially available intermediates. The key intermediate Istatin derivative (compound 2 in FIG. 17) is derived from the hydroxyiminoacetamide compound 1. Compound 1 is readily synthesized from commercially available anilines. Numerous istatins are commercially available and serve as starting materials to explore substitution on the indole aromatic ring. Condensation of the Isatin compound 2 with thiocarbazide in the presence of $K_2CO_3$ generates the indole-3-thione ring system. Alkylation with the commercially available N-(4-(N-(2-chloroethyl)sulfamoyl)phenyl) acetamide provides ATM5. Various analogues of ATM7 are synthesized such as by using different alkylating agents or through modification of the previously described procedure.

Scaffold Modifications to Expand SAR and Improve CNS Penetration Liabilities

S-alkyltriazinoindole analogues identified through the virtual screening methods described elsewhere herein provide a unique starting point for improved probes to explore allosteric modulators of transporter function. Probe molecules that demonstrate good CNS penetration are identified in order to evaluate these probes in animal models of addiction. Characteristics of CNS penetrating compounds typically have molecule weights under 400, have polar surface areas less than 40, and in many cases contain a basic amine. Incorporation of fluorine or halogen containing aromatics are also a common feature of CNS penetrating drugs. Although not wishing to be bound by any particular theory, this may be due to the reduction of overall electron density of the aromatic ring to reduce the propensity for in vivo oxidation and subsequent elimination by metabolizing enzymes such as cytochrome P450s.

Figure 18A:
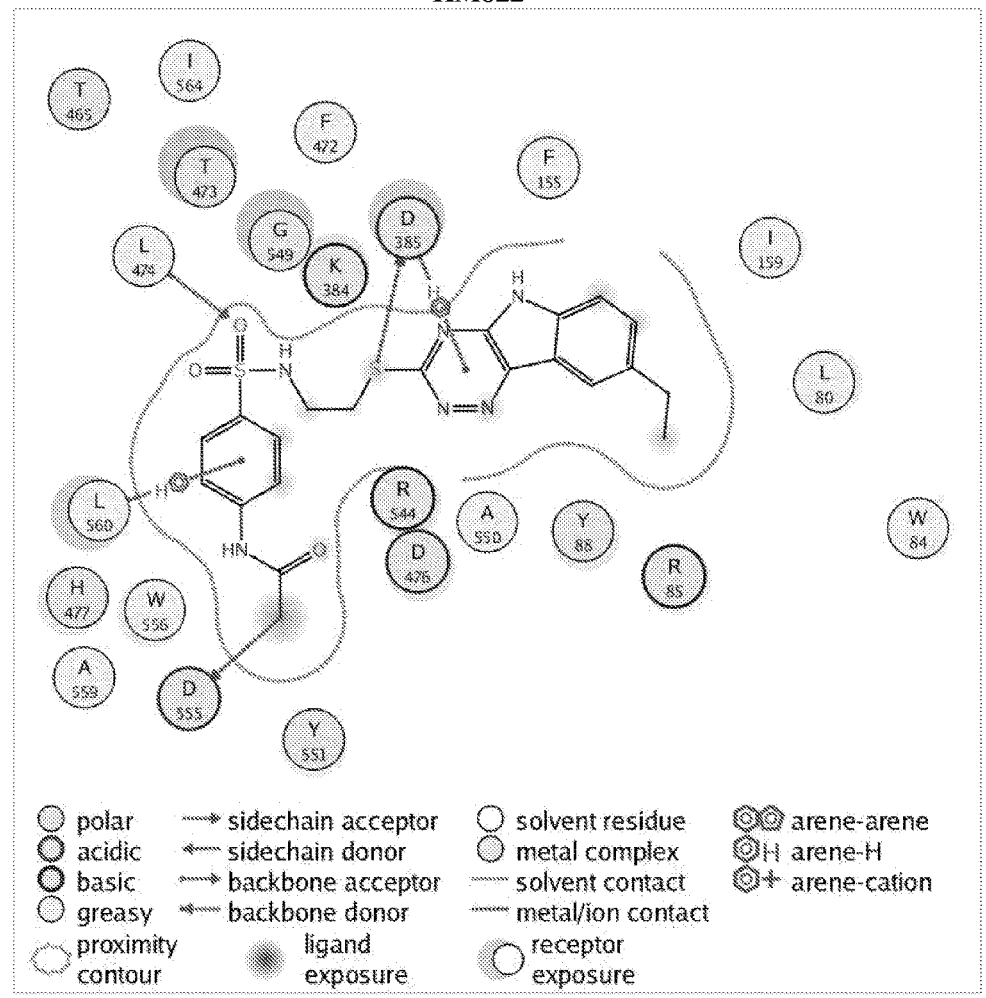
FIG. 18A-18B, illustrates the interaction between ATM5 and residues in site A1.

To increase the likelihood that the allosteric modulators identified using methods described herein ultimately demonstrate efficacy in vivo, a probe series is designed that not only meets potency and functional criteria, but also has the attributes of a CNS penetrating agent. Thus, structure-guided probe synthesis provides potency and functional efficacy in cellular assays. More than 100 analogues of ATM5 are chosen from an e-library using a focused screen with ATM5 as an input to the HSB method, such as that described in the Virtual Screening section of the methods section. The probable binding mode of ATM5 in hDAT is shown in FIG. 18A. This binding mode serves as a template to guide the rational modification of ATM5 and design its analogues. Specific features of these analogues includes reduced polarity and increased BBB permeability. Preferred modifications are identified using the focused screening procedure in HSB method which includes a rigid cut-off of log P and log D values between 2 and 4. Also, nd a replacement of the sulfonamide moiety to include other bioisosteres, such as a sulfone or esters that contribute favorably to the binding efficiency by way of strengthening the interaction with the backbone of L560 is considered.

Figure 18B:
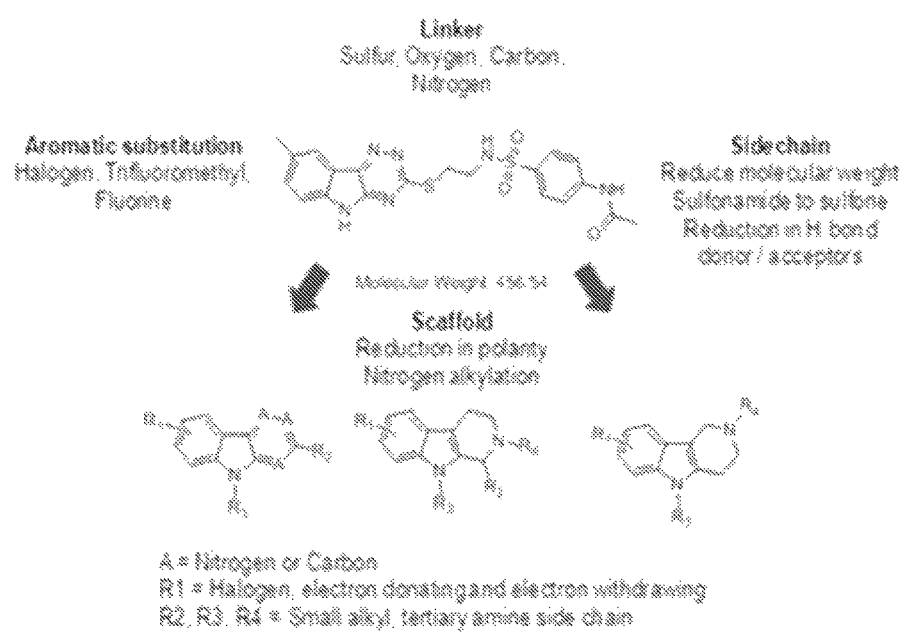
Figure 19A:
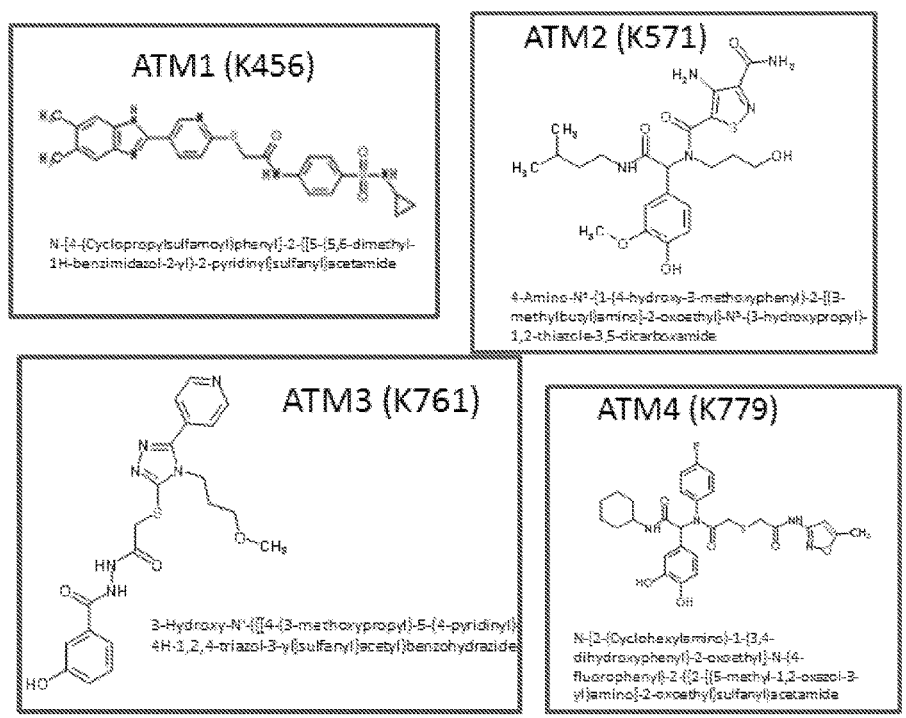
FIGS. 19A-19B, illustrates the structures of compounds identified for their ability to interfere with the uptake and amphetamine induced efflux of serotonin and dopamine at their respective transporters using methods described therein throughout.
Figure 19B:
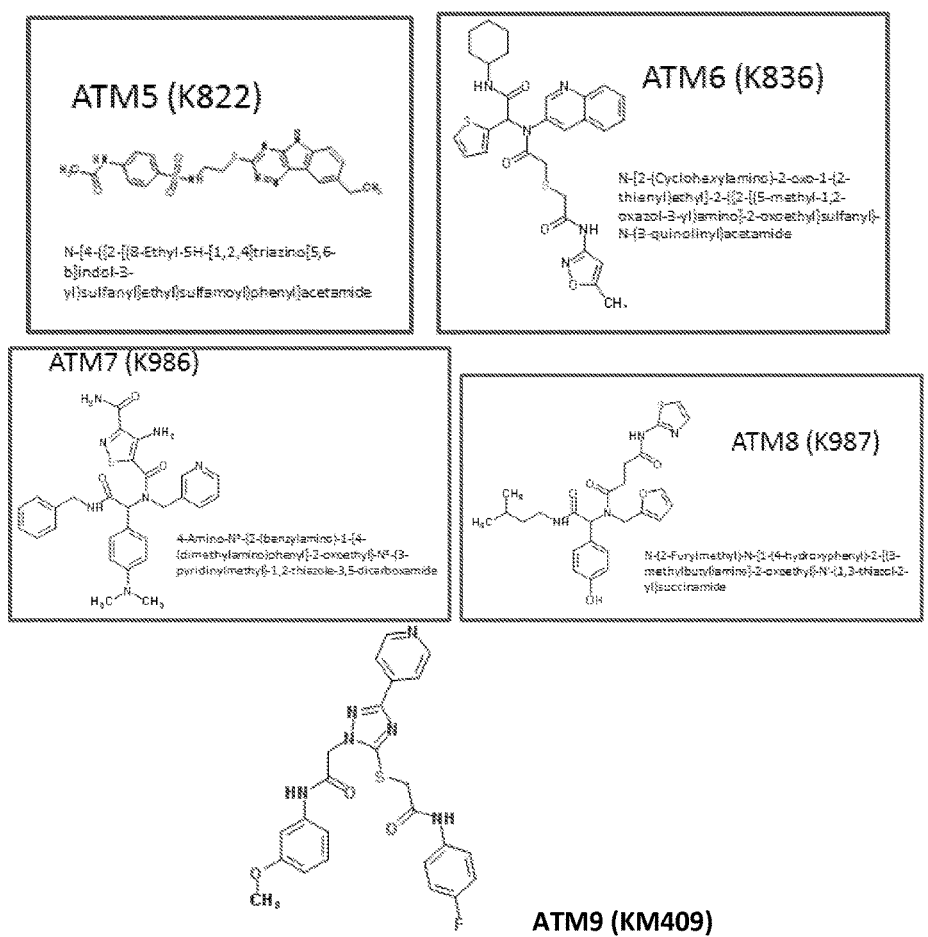
Figure 20:
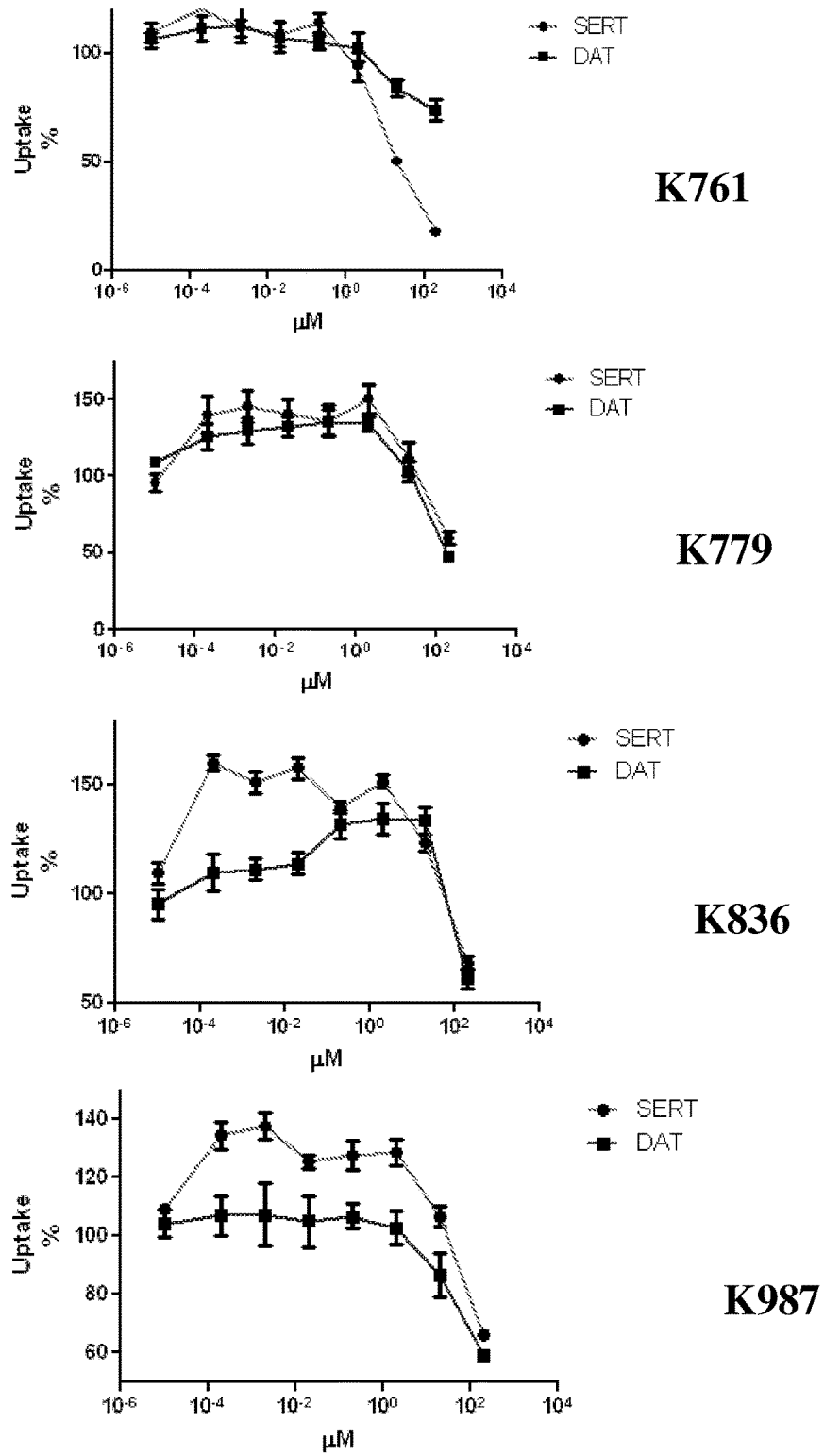
FIG. 20 is a series of graphs illustrating results from hDAT and hSERT uptake assays with transporter modulators ATM3 (K761), ATM4 (K779), ATM6 (K836), and ATM8 (K987).
Figure 21:
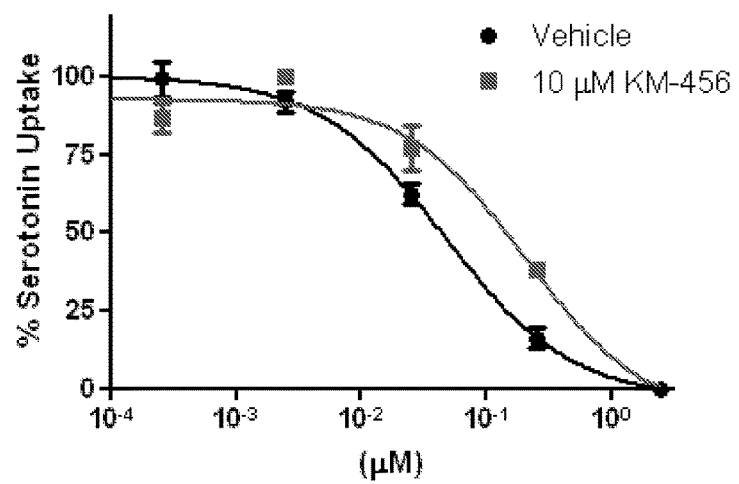
FIG. 21 is a graph illustrating the finding that the affinity for the SSRI citalopram is reduced with ATM1 (K456).
Figure 22:
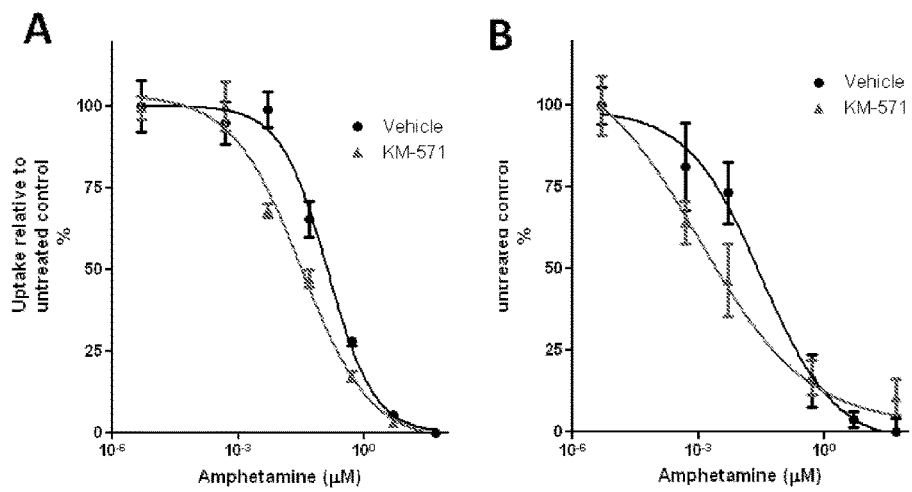
FIG. 22 is a series of graphs illustrating the finding that the affinity for amphetamine is increased with ATM2 (K571).
Figure 23:
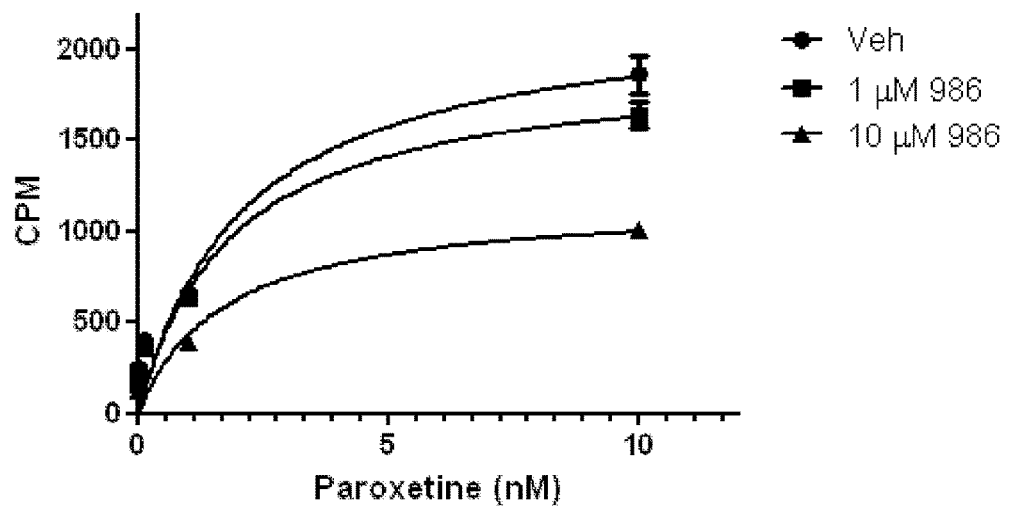
FIG. 23 is a graph illustrating the finding that paroxetine binding sites are decreased with ATM7 (K986).
Figure 24:
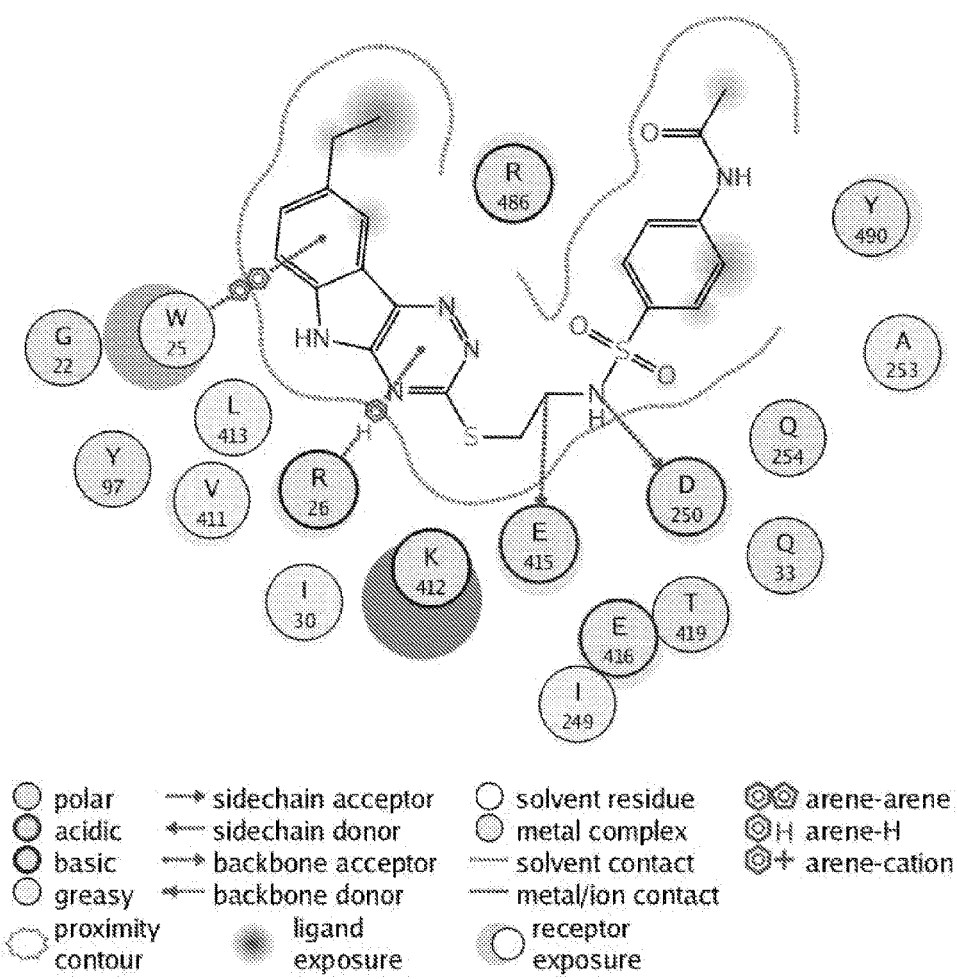
FIG. 24 is an image illustrating the interaction between ATM4 (K779) and residues in site A1.
Figure 25:
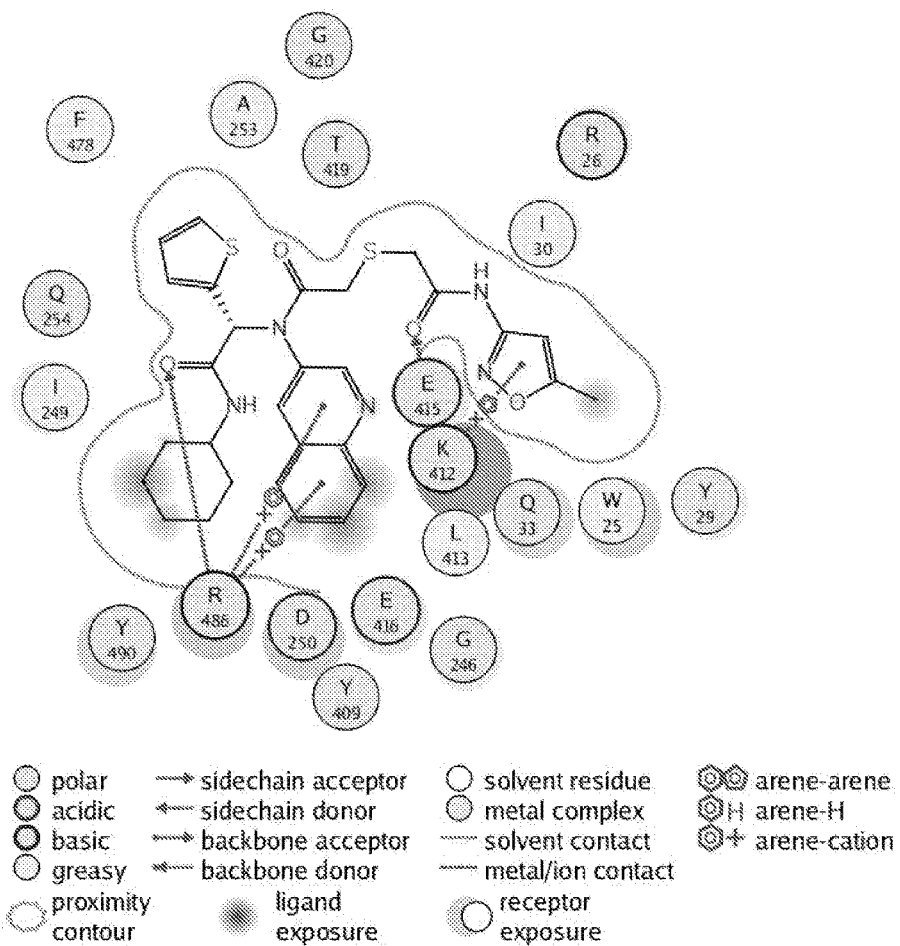
FIG. 25 is an image illustrating the interaction between ATM6 (K836) and residues in site A1.
Figure 26:
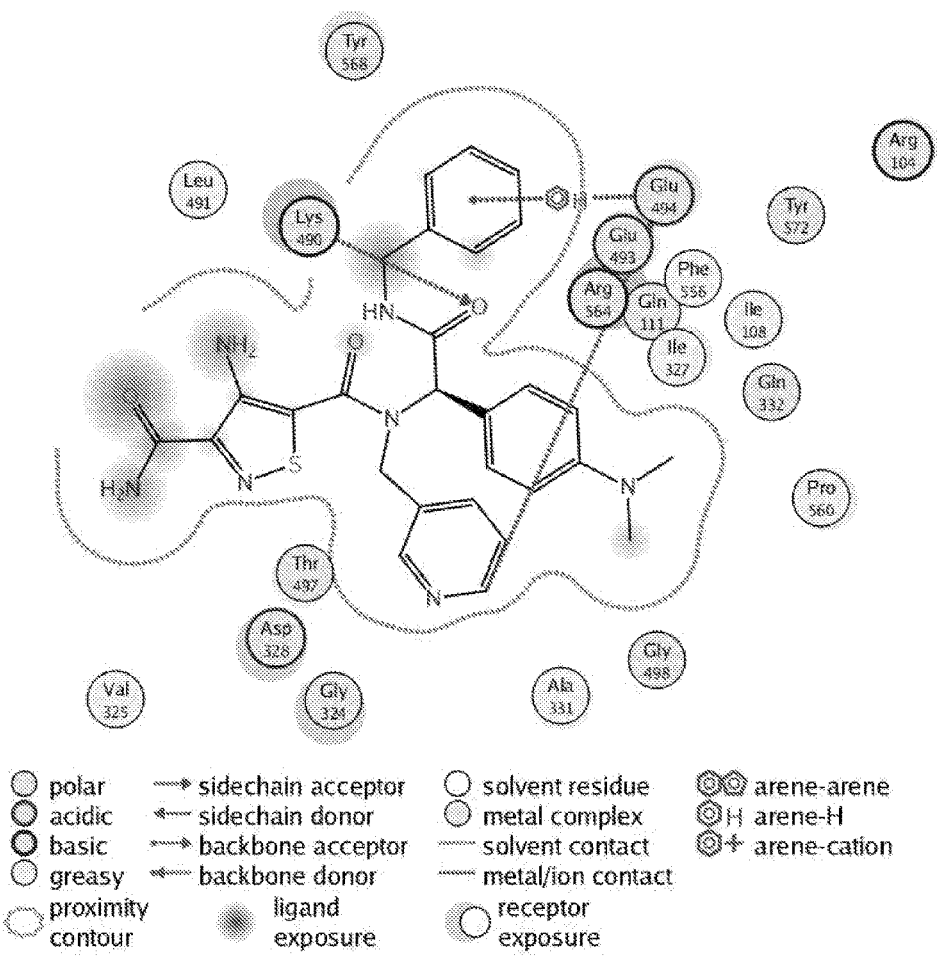
FIG. 26 is an image illustrating the interaction between ATM7 (K986) and residues in site A1.
Figure 27:
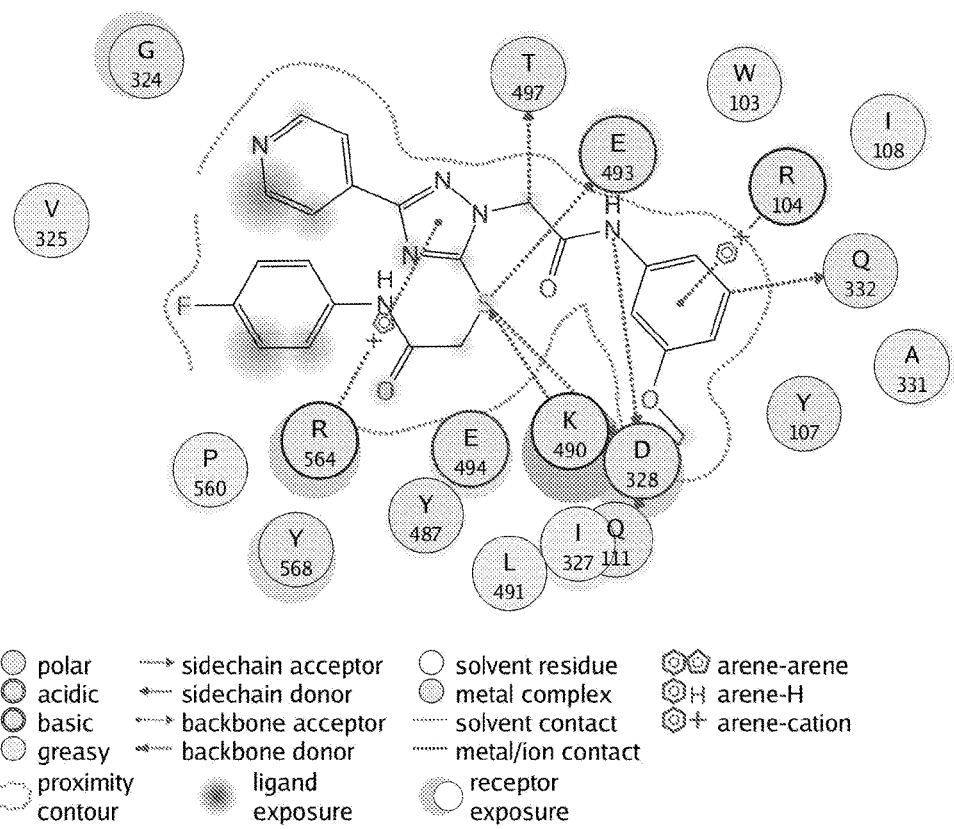
FIG. 27 is an image illustrating the interaction between KM-409 and residues in site A1.

Other functional groups that are sampled at positions R1, R2 and R3 (FIG. 18B) includes moieties that increase the interactions with the membrane and residues such as E215, E218, T465, D381, D385, that strengthen the hydrophobic interactions with V464, L222 (FIG. 18A), and that mimic the effects of N93A mutation described elsewhere herein. Specific molecules are synthesized using the procedure described above. These compounds are tested on WT and mutant forms of hDAT for functional effect on the transporter using in vitro assays such as those described in Examples 8, 11 and 12. In addition, these molecules are tested for their effect on stabilizing the outward, occluded, or inward conformation. The molecules are also tested for ion dependency and dissociation using assays such as those described in Examples 8, 11, and 12. Dimerization of SERT and DAT is examined using methods described below. Specific mutants are designed in each case and SAR of the allosteric site and its effect on the orthosteric site is derived using an iterative method of experimentation and computational modeling.

Dimerization

Whether experimental compounds affect the dimerization of the transporters DAT and SERT is explored. An assay is employed in which an inactive but surface-expressed mutant is co-expressed with WT at various ratios. A linear relationship is expected between ratio and uptake if there is no interaction between the two isoforms of the transporter proteins. For SERT it has been found that the relationship is not linear, which implies interaction between the subunits in the dimer. COS-7 cells transfected with varying ratios of binding pocket mutants and SERT-D98G or DAT-D79G plasmids are washed with PBSCM and assayed for uptake with either 150 nM [$^3$H]5HT or 300 nM [$^3$H]DA for 10 min using methods such as those described in Example 8.

Example 14

Characterizing In Vivo Efficacy and Toxicity Using Behavioral and Biochemical Methods It has been demonstrated that exposure of psychostimulants leads to behaviors that can be studied using rodent model systems. Because the studies described herein demonstrate the modulation of psychostimulant effects using allosteric modulators in in vitro biochemical studies, these compounds are examined using in vivo rodent models. These studies inform optimization of the compounds for drug like properties. The pharmacokinetics and maximum tolerated dose of compounds identified using methods described elsewhere herein are validated using rodent models. Information from pharmacokinetics (PK) and maximum tolerated dose (MTD) studies guides the dosing of these compounds for in vivo efficacy studies using behavioral models.

Pharmacokinetics (PK) and Maximum Tolerated Dose (MTD) Studies

PK and MTD studies are performed on compounds identified using methods described elsewhere herein using rodent models: All protocols are approved by the Institutional Animal Care and Use (IACUC) committee at Drexel University College of Medicine and Melior Inc. Male Sprague-Dawley rats (180-190 g, Charles River Laboratories, Wilmington, Mass.) are used. Animals are housed 2 per cage, kept on a standard 12 hr light cycle and given free access to water and standard rodent chow. Food and water are available ad libitum. Animals are not fasted for any portion of the study. Rats are acclimated to the animal care facility for seven days prior to the start of the experiment. Initial dosing is based on the EC50 values determined from functional studies to hDAT and as a rule of thumb, 10 times the EC50 value or 10 mg/kg, whichever is the lowest is utilized for the preliminary dose. Unless faced with solubility issues, sterile saline is used as vehicle with either an intraperitoneal or intravenous mode of delivery.

For the MTD studies, the doses chosen are 10, 50, 100, 150 and 300 mg/kg of the compound, which is modified based on the pilot study. The animals are monitored for body weight, food intake and scored according to Irwin parameters for general appearance, lethality, piloerection, ptosis, abdominal writhes, Exophthalmia, Lacrimation, salivation, sedation, excitation, seizures, auditory startle, straub tail, muscle tone, grasp reflex, ataxia, Righting reflex, defecation and fecal pellet count.

Statistical Analysis

Data is expressed as the average±SEM for body weight, food consumption, and each Irwin parameter. For each of these parameters, data is analyzed by two-way analysis of variance (ANOVA) followed by post-hoc Bonferroni's tests to determine statistical differences between treatment and vehicle control and time points. A p value of less than 0.05 issued to indicate statistical significance.

A separate group of animals is chosen for PK studies. A single optimal dose is used and at the designated times after dosing (5 min, 15 min., 30 min., 1 h, 2 h, 8 h, 16 h). Whole blood is collected via the retro-orbital sinus in heparinized tubes and mixed with deionized water at a 1:1 ratio for hemolyzation. Hemolyzed blood is analyzed for levels of test agent. Blood samples are extracted by a standard protocol using an acetonitrile/protein precipitation method, and levels of test agent are analyzed by liquid chromatography-mass spectrometry (LC/MS/MS). At various time points (30 min, 1 h, and 2 h) following drug administration and after the terminal bleed, brains and different brain regions are collected for analysis of brain levels of test compound.

To begin an evaluation of the efficacy and therapeutic potential of compounds identified, perform behavioral and neurochemical assays are performed. Based on the PK and MTD studies, a preferred dose is used for in vivo efficacy studies. Behavioral and neurochemical methods such as those described below provide evidence for the action of these novel modulatory agents. Microdialysis and behavior studies, such as those described in Example 10, are used to understand the effects of experimental drugs on in vivo levels of monoamines and to test the effect of drugs in animal models, respectively.

Example 15

Biological Profiling

Figure 28:
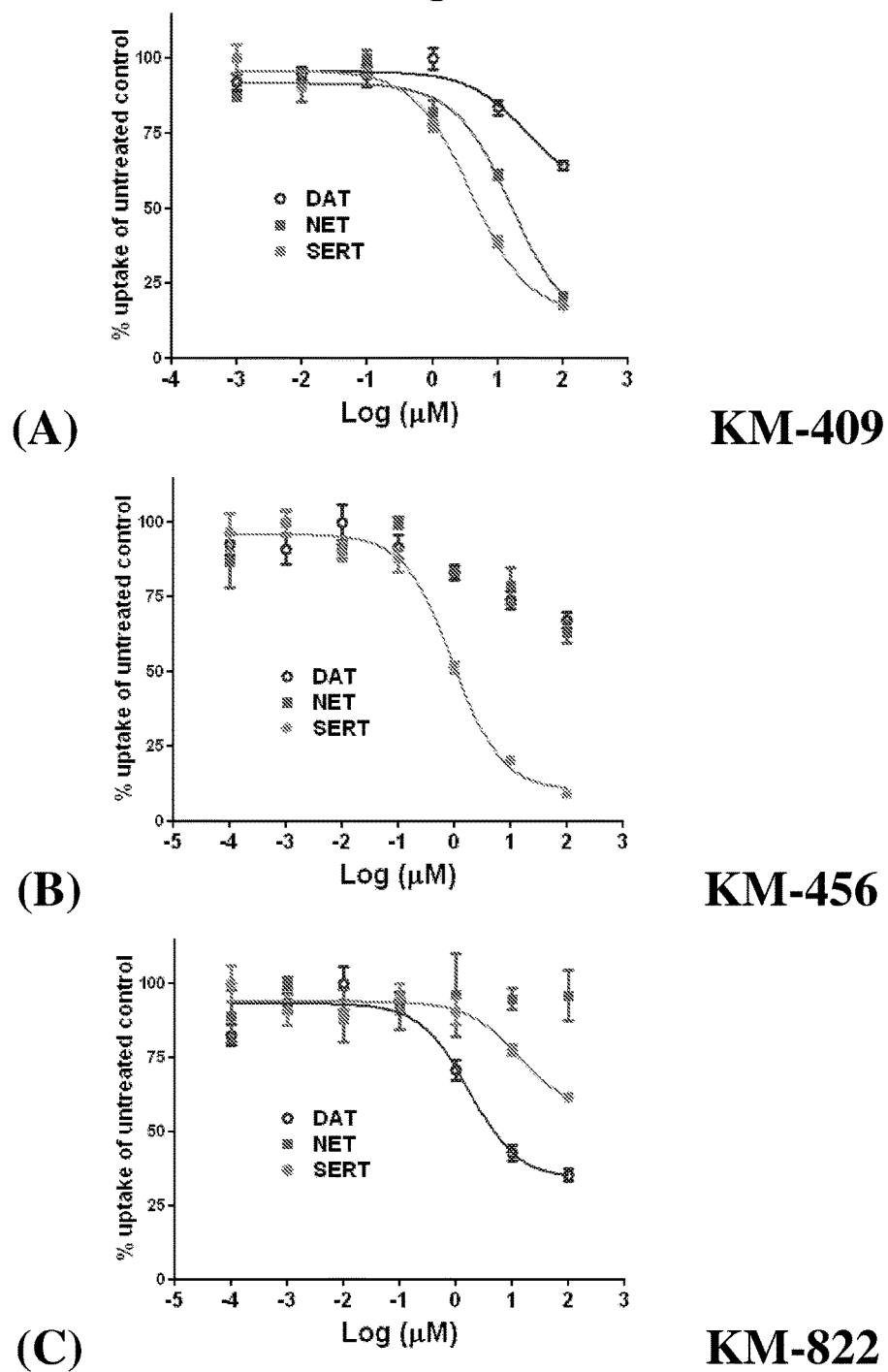
FIG. 28, comprising
Figure 29:
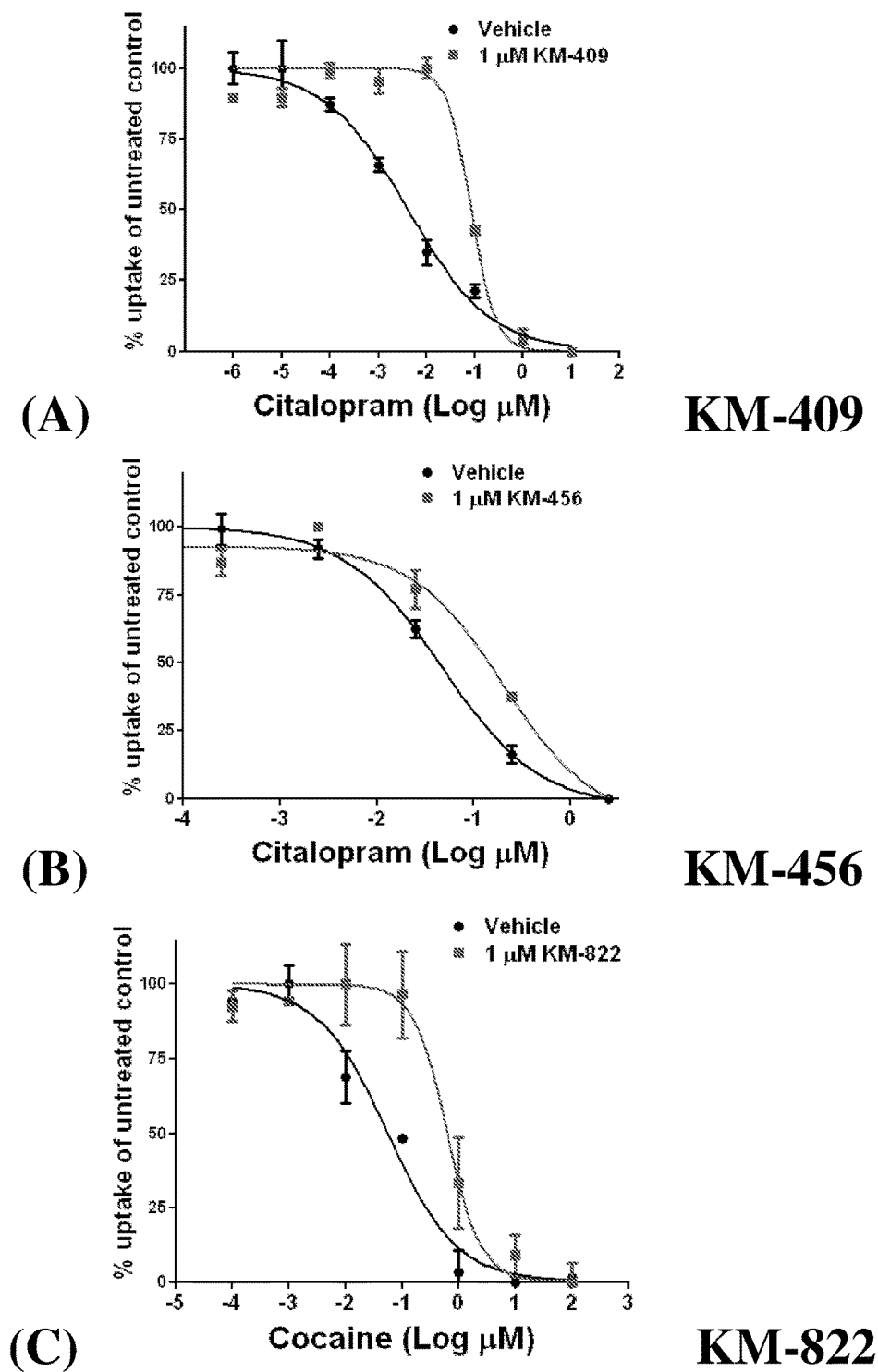
FIG. 29, comprising
Figure 30A:
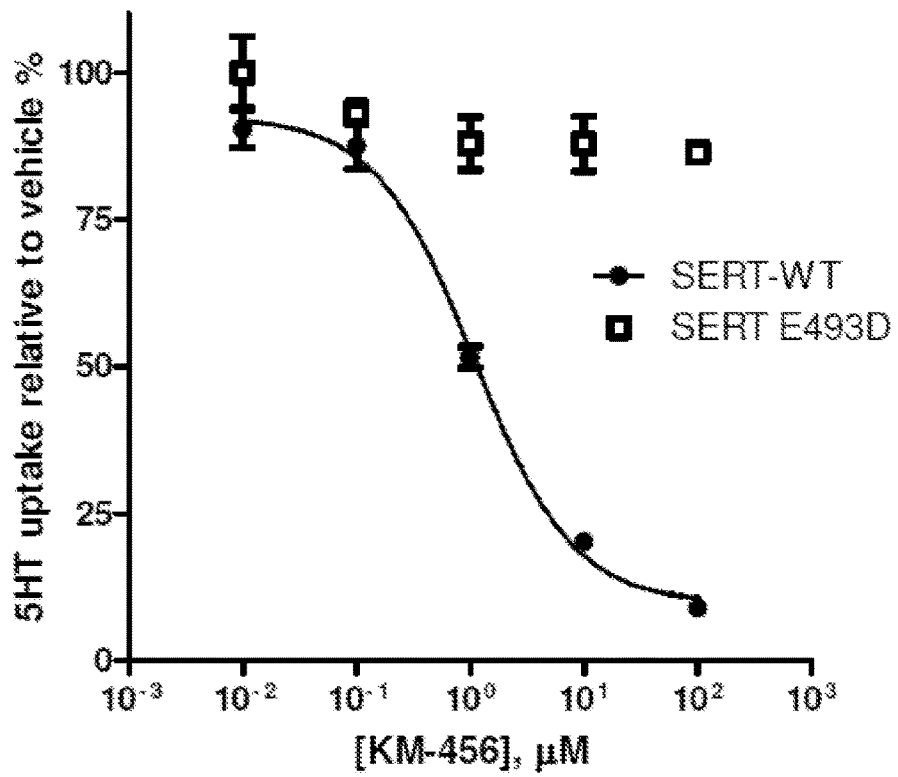
FIGS. 30A-30B, illustrates the finding that KM-456 inhibits SERT function.
Figure 30B:
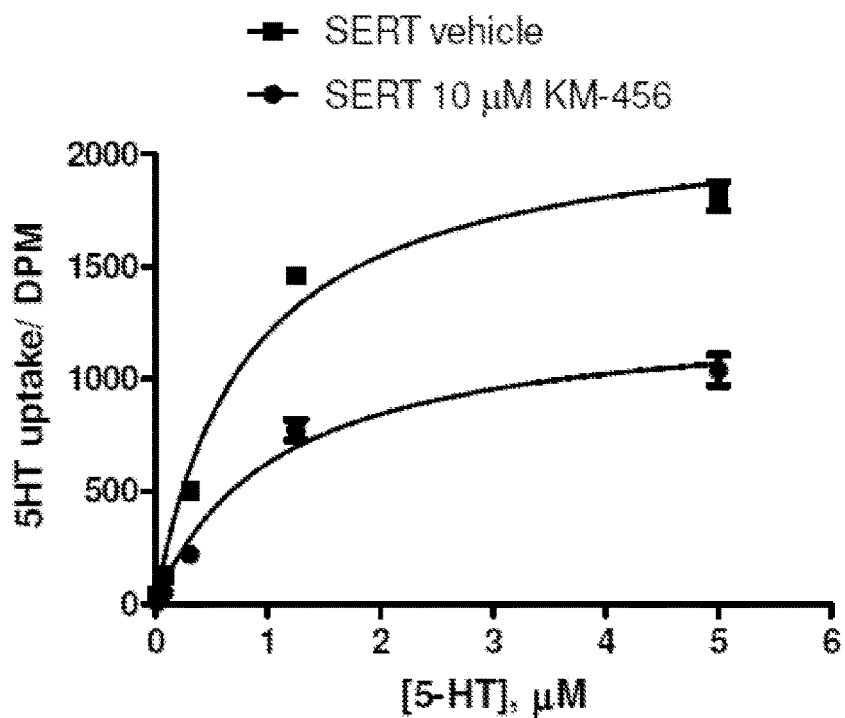

Among the molecules tested, five compounds (KM-409, KM-456, KM-571, KM-822, and KM-986) displayed modulatory effects on hDAT, hNET, and hSERT function in WT and mutant forms of the transporter. Significantly, effects of the novel compounds on transporter/inhibitory interactions were observed. KM-409 and KM-456 were shown to alter the interaction of SERT with the SSRI citalopram, decreasing its affinity for SERT, and interestingly for KM-409 the mode of interaction as the slope of the inhibition curve was dramatically altered (FIGS. 28A-28B). This result supports an allosteric mechanism of the novel compound KM-409. A strong effect of KM-822 on the interaction between DAT and cocaine was observed, decreasing the affinity of the psychostimulant (FIG. 28C). In certain embodiments, the compounds of the invention may interfere with the addictive properties of cocaine and therefore have therapeutic potential.

Additionally, subtype specific differences were also observed between the identified compounds in their effects on the MATs. KM-409 displayed activity towards NET, KM-456 was specific for SERT, and KM-822 was specific for DAT (FIG. 31). KM-571 and KM-986 displayed unique activities of enhancing transporter function. They displayed a biphasic mode of action, enhancing transporter activity at low concentrations and inhibiting transporter function at higher concentrations. Through evaluation of serotonin uptake kinetics, the stimulatory effects of KM-986 were observed only at lower nanomolar concentrations of serotonin, whereas at higher concentrations there was no significant difference—no effect of KM-986 on $V_{max}$ was observed. This suggests a complex mechanism of action of KM-986 on SERT function and points to conformation-specific and allosteric effects.

Another allosteric modulator, KM-571, displayed effects on DAT interaction with amphetamine (FIG. 12A). The affinity for amphetamine was enhanced in the presence of KM-571 and also altered the interaction fundamentally, as the Hill coefficient of the inhibition curves was different when KM-571 was present.

The effect of KM-986 on basal and MDMA-mediated efflux by hSERT was analyzed, and it was found that it potentiates MDMA-elicited efflux. Interestingly, one of the mutants (N112C) used to identify the allosteric binding pocket and that bridges residues from the allosteric site and the ligand and substrate binding sites via a hydrogen-bonded network does not show KM-986-mediated potentiation of MDMA-elicited efflux. Taken together the results with these compounds strongly support the model wherein they modulate transporter-ligand interaction.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of Formula (III):

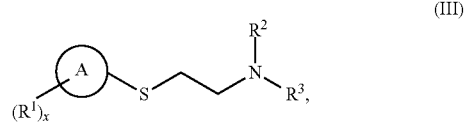

wherein in Formula (III),
ring A is triazinoindolyl optionally substituted with 1-4 $R^1$ groups;
each occurrence of $R^1$ is independently selected from the group consisting of —$C_1$-$C_6$ alkyl, —$C_1$-$C_6$ fluoroalkyl, —$C_1$-$C_6$ heteroalkyl, F, Cl, Br, and I;
$R^2$ is selected from the group consisting of H and $C_1$-$C_6$ alkyl;
$R^3$ is selected from the group consisting of —S(=O)$_2$$R^4$ and —C(=O)$R^4$;
phenyl which is optionally substituted with one or two substituents selected from the group consisting of $C_1$-$C_6$ alkyl, OH, $C_1$-$C_6$ alkoxy, halo, amino, acetamido and nitro; and
x is an integer from 0-4;
a salt or solvate thereof, and any combinations thereof.

2. The compound of claim 1, which is N-[4-({2-[(8-ethyl-5H-[1,2,4]triazino[5,6-b]indol-3-yl)sulfanyl]ethyl}sulfamoyl) phenyl]acetamide, a salt thereof, a solvate thereof, and any combinations thereof.

3. A pharmaceutically acceptable composition comprising the compound of claim 1 and a pharmaceutically acceptable carrier.

4. The compound of claim 1, wherein ring A is 8-ethyl-5H[1,2,4]triazine[5,6-b]indol3-yl.

5. The compound of claim 1, wherein each occurrence of $R^1$ is independently selected from the group consisting of —$C_1$-$C_6$ alkyl, —$C_1$-$C_6$ fluoroalkyl and —$C_1$-$C_6$ heteroalkyl.

6. The compound of claim 5, wherein each occurrence of $R^1$ is independently —$C_1$-$C_6$ alkyl.

7. The compound of claim 1, wherein $R^2$ is H.

8. The compound of claim 1, wherein $R^3$ is —S(=O)$_2$$R^4$.

9. The compound of claim 1, wherein $R^4$ is 4-acetamidophenyl.

* * * * *

UNITED STATES PATENT AND TRADEMARK OFFICE
CERTIFICATE OF CORRECTION

PATENT NO. : 9,616,065 B2  
APPLICATION NO. : 14/784536  
DATED : April 11, 2017  
INVENTOR(S) : Sandhya Kortagere et al.

It is certified that error appears in the above-identified patent and that said Letters Patent is hereby corrected as shown below:

In the Claims

In Claim 1, Column 60, Line 20, the sentence should read:
-- R4 is phenyl which is optionally substituted with one or two --

Signed and Sealed this
Twenty-fifth Day of September, 2018

Andrei Iancu
*Director of the United States Patent and Trademark Office*